(12) United States Patent
Spiegelman et al.

(10) Patent No.: US 6,872,391 B2
(45) Date of Patent: Mar. 29, 2005

(54) PGC-1, A NOVEL BROWN FAT PPAR$_\gamma$ COACTIVATOR

(75) Inventors: Bruce M. Spiegelman, Waban, MA (US); Pere Puigserver, Brookline, MA (US); Zhidan Wu, Boston, MA (US); Guillaume Adelmant, Boston, MA (US)

(73) Assignee: Dana-Farber Cancer Institute, Boston, MA (US)

( * ) Notice: Subject to any disclaimer, the term of this patent is extended or adjusted under 35 U.S.C. 154(b) by 466 days.

(21) Appl. No.: 10/256,889

(22) Filed: Sep. 27, 2002

(65) Prior Publication Data

US 2003/0073819 A1 Apr. 17, 2003

Related U.S. Application Data

(63) Continuation of application No. 09/900,236, filed on Jul. 5, 2000, which is a division of application No. 09/203,453, filed on Dec. 1, 1998, now Pat. No. 6,426,411, which is a continuation-in-part of application No. 09/086,912, filed on May 29, 1998, now Pat. No. 6,166,192.
(60) Provisional application No. 60/048,107, filed on May 30, 1997.

(51) Int. Cl.$^7$ .............................................. A61K 39/395
(52) U.S. Cl. .................... 424/130.1; 435/7.1; 435/91.1; 435/326; 435/810; 530/388.1; 530/403; 436/501; 536/23.1
(58) Field of Search ........................ 424/130.1; 435/7.1, 435/91.1, 326, 810; 530/388.1, 403; 436/501; 536/23.1

(56) References Cited

U.S. PATENT DOCUMENTS

6,028,109 A * 2/2000 Wilson ........................ 514/567

FOREIGN PATENT DOCUMENTS

WO        WO 97/10337        3/1997

OTHER PUBLICATIONS

Brun, R.P. et al. "Adipocyte Differentiation: a Transcriptional Regulatory Cascade" *Current Opinion in Cell Biology* 8:826–832 (1996).
Cavaillès, V. et al. "Nuclear Factor RIP140 Modulates Transcriptional Activation by the Estrogen Receptor" *The EMBO Journal* 14(15):3741–3751 (1995).
Chakravarti, D. et al. "Role of CBP/P300 in Nuclear Receptor Signalling" *Nature* 383:99–103 (1996).
Chen, H. et al. "Nuclear Receptor Coactibator ACTR Is a Novel Histone Acetyltransferase and Forms a Multimeric Activation Complex with P/CAF and CBP/p300" *Cell* 90:569–580 (1997).
DiRenzo, J. et al. "Peroxisome Proliferator–Activated Receptors and Retinoic Acid Receptors Differentially Control the Interactions of Retinoid X Receptor Heterodimers with Ligands, Coactivators, and Corepressors" *Molecular and Cellular Biology* 17(4):2166–2176 (1997).
Flier, J.S. and Lowell, B.B. "Obesity Research Springs a Proton Leak" *Nature Genetics* 15:223–224 (1997).
GenBank Accession No: AA107666; Feb. 4, 1997.
GenBank Accession No: AA188859; Jan. 13, 1997.
GenBank Accession No: AA242576; Mar. 7, 1997.
GenBank Accession No: AA388127; Apr. 23, 1997.
GenBank Accession No: AA388152; Apr. 23, 1997.
GenBank Accession No: AA413411; May 7, 1997.
GenBank Accession No: AA673291; Nov. 26, 1997.
GenBank Accession No: AA865326; Mar. 12, 1998.
GenBank Accession No: AI059434; Feb. 11, 1999.
GenBank Accession No: AI137178; Feb. 11, 1999.
Heery et al. (1997) "A signature motif in transcriptional co–activators mediates binding to nuclear receptors". *Nature* 387:733–736.
Himms–Hagen, J. "Role of Thermogeniesis in the Regulation of Energy Balance in Relation to Obesity" *Can. J. Physiol. Pharmacol.* 67:374–401 (1989).
Hu, E. et al. "Inhibition of Adipogenesis Through MAP Kinase–Mediated Phosphorylation of PPAR$\gamma$" *Science: Reprint Series*:274:2100–2103 (1996).
Kamei, Y. et al. "A CBP Integrator Complex Mediates Transcriptional Activation and AP–1 Inhibition by Nuclear Receptors" *Cell* 85:403–414 (1996).
Kliewer, S.A. et al. "Fatty Acids and Eicosanoids Regulate Gene Expression Through Direct Interations with Peroxisome Proliferator–activated Receptors $\alpha$ and $\gamma$" *Proc. Natl. Acad. Sci. USA* 94:4318–4323 (1997).
Oñate, S.A. et al. "Sequence and charachterization of a Coactivator for the Steroid Hormone Receptor Superfamily" *Science* 270:1354–1356 (1995).

(Continued)

Primary Examiner—Laurie Scheiner
(74) Attorney, Agent, or Firm—Lahive & Cockfield LLP; Amy E. Mandragouras, Esq.; DeAnn F. Smith, Esq.

(57) ABSTRACT

The invention provides isolated nucleic acids molecules, designated PGC-1 nucleic acid molecules, which encode proteins which can modulate various adipocyte-associated activities including, for example, thermogenesis in adipocytes, e.g., brown adipocytes, and adipogenesis. The invention also provides antisense nucleic acid molecules, recombinant expression vectors containing PGC-1 nucleic acid molecules, host cells into which the expression vectors have been introduced, and nonhuman transgenic animals in which a PGC-1 gene has been introduced or disrupted. The invention still further provides isolated PGC-1 proteins, fusion proteins, antigenic peptides and anti-PGC-1 antibodies. Diagnostic, screening, and therapeutic methods utilizing compositions of the invention are also provided.

6 Claims, 16 Drawing Sheets

OTHER PUBLICATIONS

Pillar, T.M. and Seitz, H.J. "Thyroid Hormone and Gene Expression in the Regulation of Mitochondrial Respiratory Function" *European Journal of Endocrinology* 136:231–239 (1997).

Puigserver, P. et al. "A Cold–Inducible Coactivator of Nuclear Receptors Linked to Adaptive Thermogenesis" *Cell* 92:829–839 (1998).

Sears, I.B. et al. "Differentiation–Dependent Expression of the Brown Adipocyte Uncoupling Protein Gene: Regulation by Peroxisome Proliferator–Activated Receptor γ" *Molecular and Cellular Biology* 16(7):3410–3419 (1996).

Spiegelman, B.M. and Flier, J.S. "Adipogenesis and Obesity: Rounding Out the Big Picture" *Cell* 87:377–389 (1996).

Tontonoz, P. et al. "Stimulation of Adipogenesis in Firoblasts by PPARγ2, a Lipid–Activated Transcription Factor" *Cell* 79:1147–1156 (1994).

Torchia et al. (1997) "The transcriptional co–activator p/CIP binds CBP and mediates nuclear–receptor function.". *Nature* 387:677–684.

Yuryev et al. (1996) "The C–terminal domain of the largest subunit of RNA polymerase II interacts with a novel set of serine/arginine–rich proteins.". *Proc. Natl. Acad. Sci. USA* 93:6975–6980.

Voegel, J.J. et al. "TIF2, a 160 kDa Transcriptional Mediator for the Ligand–Dependent Activation Function AF–2 of Nuclear Receptors" *The EMBO Journal* 15(14):3667–3675 (1996).

Zhu, Y. et al. "Cloning and Identification of Mouse Steroid Receptor Coactivator–1 (mSRC–1), as a Coactivator of Peroxisome Proliferator–Activated Receptor γ" *Gene Expression* 6:185–195 (1996).

Zhu, Y. et al. "Isolation and Characterization of PBP, a Protein That Interacts with Peroxisome Proliferator–Activated Receptor" *The Journal of Biological Chemistry* 272(41):25500–25506 (1997).

* cited by examiner

FIG. 1A

```
                10                      30                      50
     AATTCGGCACGAGGTTGCCTGCATGAGTGTGTGCTGTGTGTCAGAGTGGATTGGAGTTGA
                70                      90                     110
     AAAAGCTTGACTGGCGTCATTCGGGAGCTGGATGGCTTGGGACATGTGCAGCCAAGACTC
                                          M  A  W  D  M  C  S  Q  D  S
               130                     150                     170
     TGTATGGAGTGACATAGAGTGTGCTGCTCTGGTTGGTGAGGACCAGCCTCTTTGCCCAGA
      V  W  S  D  I  E  C  A  A  L  V  G  E  D  Q  P  L  C  P  D
               190                     210                     230
     TCTTCCTGAACTTGACCTTTCTGAACTTGATGTGAATGACTTGGATACAGACAGCTTTCT
      L  P  E  L  D  L  S  E  L  D  V  N  D  L  D  T  D  S  F  L
               250                     270                     290
     GGGTGGATTGAAGTGGTGTAGCGACCAATCGGAAATCATATCCAACCAGTACAACAATGA
      G  G  L  K  W  C  S  D  Q  S  E  I  I  S  N  Q  Y  N  N  E
               310                     330                     350
     GCCTGCGAACATATTTGAGAAGATAGATGAAGAGAATGAGGCAAACTTGCTAGCGGTCCT
      P  A  N  I  F  E  K  I  D  E  E  N  E  A  N  L  L  A  V  L
               370                     390                     410
     CACAGAGACACTGGACAGTCTCCCCGTGGATGAAGACGGATTGCCCTCATTTGATGCACT
      T  E  T  L  D  S  L  P  V  D  E  D  G  L  P  S  F  D  A  L
               430                     450                     470
     GACAGATGGAGCCGTGACCACTGACAACGAGGCCAGTCCTTCCTCCATGCCTGACGGCAC
      T  D  G  A  V  T  T  D  N  E  A  S  P  S  S  M  P  D  G  T
               490                     510                     530
     CCCTCCCCCTCAGGAGGCAGAAGAGCCGTCTCTACTTAAGAAGCTCTTACTGGCACCAGC
      P  P  P  Q  E  A  E  E  P  S  L  L  K  K  L  L  L  A  P  A
               550                     570                     590
     CAACACTCAGCTCAGCTACAATGAATGCAGCGGTCTTAGCACTCAGAACCATGCAGCAAA
      N  T  Q  L  S  Y  N  E  C  S  G  L  S  T  Q  N  H  A  A  N
               610                     630                     650
     CCACACCCACAGGATCAGAACAAACCCTGCCATTGTTAAGACCGAGAATTCATGGAGCAA
      H  T  H  R  I  R  T  N  P  A  I  V  K  T  E  N  S  W  S  N
               670                     690                     710
     TAAAGCAAGAGCATTTGTCAACAGCAAAAGCCACAAAGACGTCCCTGCTCAGAGCTTCT
      K  A  K  S  I  C  Q  Q  Q  K  P  Q  R  R  P  C  S  E  L  L
               730                     750                     770
     CAAGTATCTGACCACAAACGATGACCCTCCTCACACCAAACCCACAGAAAACAGGAACAG
      K  Y  L  T  T  N  D  D  P  P  H  T  K  P  T  E  N  R  N  S
               790                     810                     830
     CAGCAGAGACAAATGTGCTTCCAAAAAGAAGTCCCATACACAACCGCAGTCGCAACATGC
      S  R  D  K  C  A  S  K  K  K  S  H  T  Q  P  Q  S  Q  H  A
               850                     870                     890
     TCAAGCCAAACCAACAACTTTATCTCTTCCTCTGACCCCAGAGTCACCAAATGACCCCAA
      Q  A  K  P  T  T  L  S  L  P  T  P  E  S  P  N  D  P  K
               910                     930                     950
     GGGTTCCCCATTTGAGAACAAGACTATTGAGCGAACCTTAAGTGTGGAACTCTCTGGAAC
      G  S  P  F  E  N  K  T  I  E  R  T  L  S  V  E  L  S  G  T
               970                     990                    1010
     TGCAGGCCTAACTCCTCCCACAACTCCTCCTCATAAAGCCAACCAAGATAACCCTTTCAA
      A  G  L  T  P  P  T  T  P  P  H  K  A  N  Q  D  N  P  F  K
```

FIG. 1B

```
              1030                    1050                    1070
     GGCTTCGCCAAAGCTGAAGCCCTCTTGCAAGACCGTGGTGCCACCGCCAACCAAGAGGGC
      A  S  P  K  L  K  P  S  C  K  T  V  V  P  P  P  T  K  R  A
              1090                    1110                    1130
     CCGGTACAGTGAGTGTTCTGGTACCCAAGGCAGCCACTCCACCAAGAAAGGGCCCGAGCA
      R  Y  S  E  C  S  G  T  Q  G  S  H  S  T  K  K  G  P  E  Q
              1150                    1170                    1190
     ATCTGAGTTGTACGCACAACTCAGCAAGTCCTCAGGGCTCAGCCGAGGACACGAGGAAAG
      S  E  L  Y  A  Q  L  S  K  S  S  G  L  S  R  G  H  E  E  R
              1210                    1230                    1250
     GAAGACTAAACGGCCCAGTCTCCGGCTGTTTGGTGACCATGACTACTGTCAGTCACTCAA
      K  T  K  R  P  S  L  R  L  F  G  D  H  D  Y  C  Q  S  L  N
              1270                    1290                    1310
     TTCCAAAACGGATATACTCATTAACATATCACAGGAGCTCCAAGACTCTAGACAACTAGA
      S  K  T  D  I  L  I  N  I  S  Q  E  L  Q  D  S  R  Q  L  D
              1330                    1350                    1370
     CTTCAAAGATGCCTCCTGTGACTGGCAGGGGCACATCTGTTCTTCCACAGATTCAGGCCA
      F  K  D  A  S  C  D  W  Q  G  H  I  C  S  S  T  D  S  G  Q
              1390                    1410                    1430
     GTGCTACCTGAGAGAGACTTTGGAGGCCAGCAAGCAGGTCTCTCCTTGCAGCACCAGAAA
      C  Y  L  R  E  T  L  E  A  S  K  Q  V  S  P  C  S  T  R  K
              1450                    1470                    1490
     ACAGCTCCAAGACCAGGAAATCCGAGCGGAGCTGAACAAGCACTTCGGTCATCCCTGTCA
      Q  L  Q  D  Q  E  I  R  A  E  L  N  K  H  F  G  H  P  C  Q
              1510                    1530                    1550
     AGCTGTGTTTGACGACAAATCAGACAAGACCAGTGAACTAAGGGATGGCGACTTCAGTAA
      A  V  F  D  D  K  S  D  K  T  S  E  L  R  D  G  D  F  S  N
              1570                    1590                    1610
     TGAACAATTCTCCAAACTACCTGTGTTTATAAATTCAGGACTAGCCATGGATGGCCTATT
      E  Q  F  S  K  L  P  V  F  I  N  S  G  L  A  M  D  G  L  F
              1630                    1650                    1670
     TGATGACAGTGAAGATGAAAGTGATAAACTGAGCTACCCTTGGGATGGCACGCAGCCCTA
      D  D  S  E  D  E  S  D  K  L  S  Y  P  W  D  G  T  Q  P  Y
              1690                    1710                    1730
     TTCATTGTTCGATGTGTCGCCTTCTTGCTCTTCCTTTAACTCTCCGTGTCGAGACTCAGT
      S  L  F  D  V  S  P  S  C  S  S  F  N  S  P  C  R  D  S  V
              1750                    1770                    1790
     GTCACCACCGAAATCCTTATTTTCTCAAAGACCCCAAAGGATGCGCTCTCGTTCAAGATC
      S  P  P  K  S  L  F  S  Q  R  P  Q  R  M  R  S  R  S  R  S
              1810                    1830                    1850
     CTTTTCTCGACACAGGTCGTGTTCCCGATCACCATATTCCAGGTCAAGATCAAGGTCCCC
      F  S  R  H  R  S  C  S  R  S  P  Y  S  R  S  R  S  P
              1870                    1890                    1910
     AGGCAGTAGATCCTCTTCAAGATCCTGTTACTACTATGAATCAAGCCACTACAGACACCG
      G  S  R  S  S  S  R  S  C  Y  Y  Y  E  S  S  H  Y  R  H  R
              1930                    1950                    1970
     CACACACCGCAATTCTCCCTTGTATGTGAGATCACGTTCAAGGTCACCCTACAGCCGTAG
      T  H  R  N  S  P  L  Y  V  R  S  R  S  R  S  P  Y  S  R  R
```

FIG. 1C

```
           1990                 2010                2030
GCCCAGGTACGACAGCTATGAAGCCTATGAGCACGAAAGGCTCAAGAGGGATGAATACCG
  P  R  Y  D  S  Y  E  A  Y  E  H  E  R  L  K  R  D  E  Y  R
           2050                 2070                2090
CAAAGAGCACGAGAAGCGGGAGTCTGAAAGGGCCAAACAGAGAGAGAGGCAGAAGCAGAA
  K  E  H  E  K  R  E  S  E  R  A  K  Q  R  E  R  Q  K  Q  K
           2110                 2130                2150
AGCAATTGAAGAGCGCCGTGTGATTTACGTTGGTAAAATCAGACCTGACACAACGCGGAC
  A  I  E  E  R  R  V  I  Y  V  G  K  I  R  P  D  T  T  R  T
           2170                 2190                2210
AGAATTGAGAGACCGCTTTGAAGTTTTTGGTGAAATTGAGGAATGCACCGTAAATCTGCG
  E  L  R  D  R  F  E  V  F  G  E  I  E  E  C  T  V  N  L  R
           2230                 2250                2270
GGATGATGGAGACAGCTATGGTTTCATCACCTACCGTTACACCTGTGACGCTTTCGCTGC
  D  D  G  D  S  Y  G  F  I  T  Y  R  Y  T  C  D  A  F  A  A
           2290                 2310                2330
TCTTGAGAATGGATATACTTTACGCAGGTCGAACGAAACTGACTTCgagctgtacttttg
  L  E  N  G  Y  T  L  R  R  S  N  E  T  D  F  E  L  Y  F  C
           2350                 2370                2390
tggacggaagcaattttcaagtctaactatgcagacctagataccaactcagacgattt
  G  R  K  Q  F  F  K  S  N  Y  A  D  L  D  T  N  S  D  D  F
           2410                 2430                2450
tgaccctgcttccaccaagagcaagtatgactctctggattttgatagtttactgaagga
  D  P  A  S  T  K  S  K  Y  D  S  L  D  F  D  S  L  L  K  E
           2470                 2490                2510
agctcagagaagcttgcgcaggtaacgtgttcccaggctgaggaatgacagagagatggt
  A  Q  R  S  L  R  R
           2530                 2550                2570
caataccctcatgggacagcgtgtcctttcccaagactcttgcaagtcatacttaggaatt
           2590                 2610                2630
tctcctactttacactctctgtacaaaaataaaacaaaacaaaacaacaataacaacaac
           2650                 2670                2690
aacaacaacaataacaacaacaaccataccagaacaagaacaacggtttacatgaacaca
           2710                 2730                2750
gctgctgaagaggcaagagacagaatgataatccagtaagcacacgtttattcacgggtg
           2770                 2790                2810
tcagctttgctttccctggaggctcttggtgacagtgtgtgcgtgtgtgtgtgggt
           2830                 2850                2870
gtgcgtgtgtgtatgtgtgtgtgtacttgtttggaaagtacatatgtacacatgtgag
           2890                 2910                2930
gacttgggggcacctgaacagaacgaacaagggcgaccccttcaaatggcagcatttcca
           2950                 2970                2990
tgaagacacacttaaaacctacaacttcaaaatgttcgtattctatacaaaaggaaaata
           3010                 3030                3050
aataaatataaaaaaaaaaaaaaaaaaaactcgagagatctatgaatcgtagatactgaaa
aaccccc
```

FIG. 2A

```
  1 MAWDMCSQDS VWSDIECAAL VGEDQPLCPD LPELDLSELD VNDLDTDSFL
 51 GGLKWCSDQS EIISNQYNNE PANIFEKIDE ENEANLLAVL TETLDSLPVD
101 EDGLPSFDAL TDGAVTTDNE ASPSSMPDGT PPPQEAEEPS LLKKLLAPA
150 NTQLSYNECS GLSTQNHAAN HTHRIRTNPA IVKTENSWSN KAKSICQQQK
200 PQRRPCSLLK YLTTPEPPHT KPTENRNSSR DKCAASKKSH TQPQSQHA
250 QAKPTTLSLP LTPESPNDPK GSPFENKTIE RTLSVELSGT AGLTPPTPP
300 HKANQDNPFK KASPKLKPSC KTVVPPPTKR ARYSECSGTQ GSHSTKKGPE
350 Q SELYAQLSKS SGLKDASRQE ERKTKRPSLR LFGDHDYCQL ETLEASKQV
400 LNSKTDILINIS QLQDEIRAEL NKHFGHPCQA VFDDKSDKTS ELRDGDFSNE
    QFSKLPVFI
450 QLGLAMDGLF DDSEDESDKL SYPWDGTQPY SLFDVSPSCS SFNSPCRDSV
500 S SPPKSLFSQR PORMRSRSFS RHRSCSRSRS PYSRSRSPYS RSRSPSRRS
550 SSRSCY
600 YYESSHYRHR THRNSPLYVR SRSRSPYSRR PRYDSYEAYE HERLKRDEYR
650 KEHEKRESER AKQREKQKAI EERRVIYVGK IRPDTTRTEL RDREEVFG
700 EIECTVNLRD DGSYGFITYR YTCDAFAALE NGYTLRRSNE TDFELYFC
750 GRKQFFKSNY ADLDTNSDDF DPASTKSKYD SLDFDSLLKE AQRSLRR
797
```

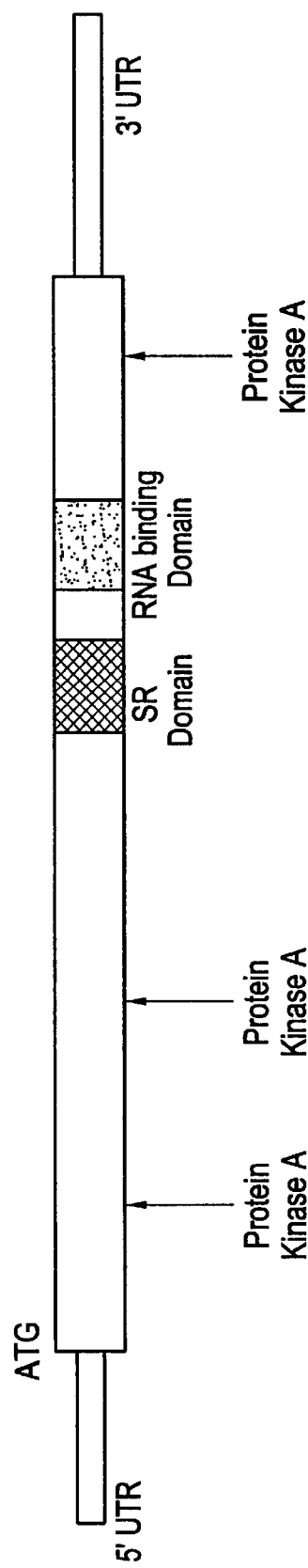

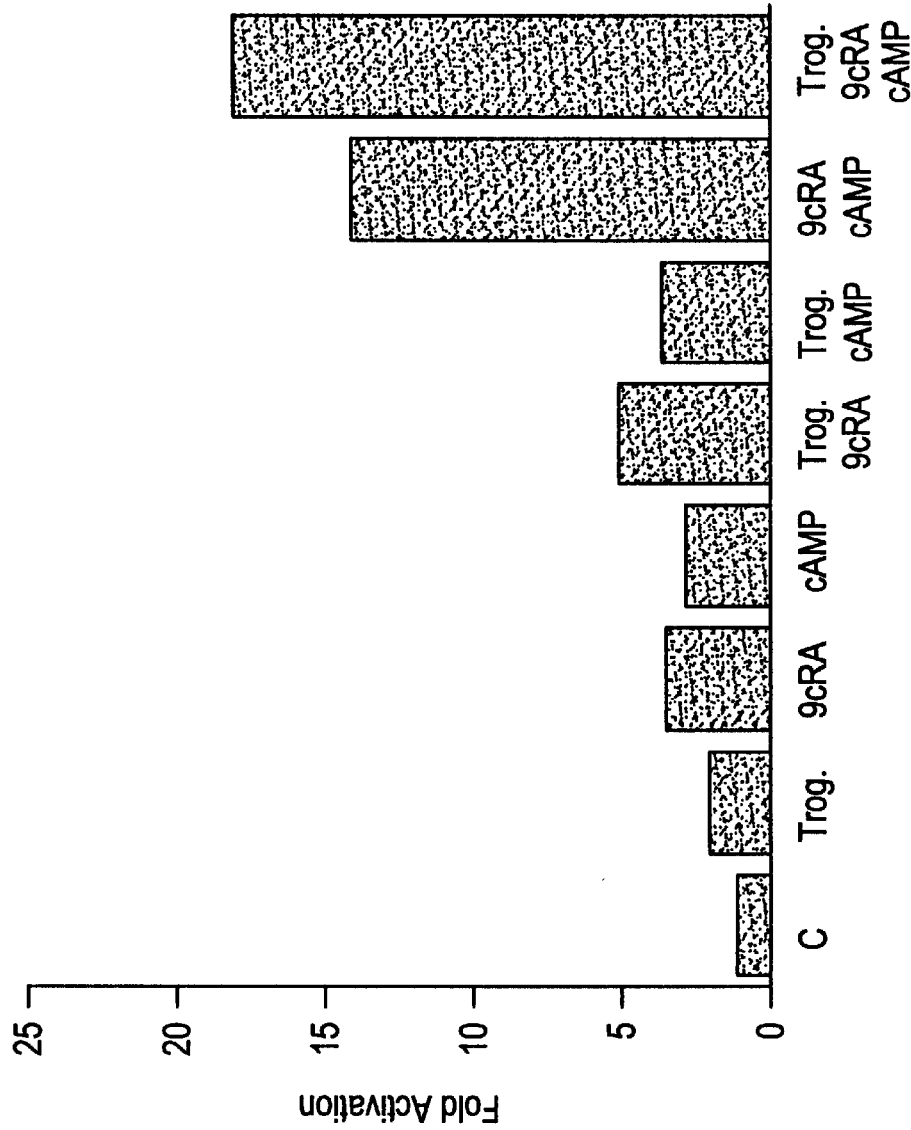

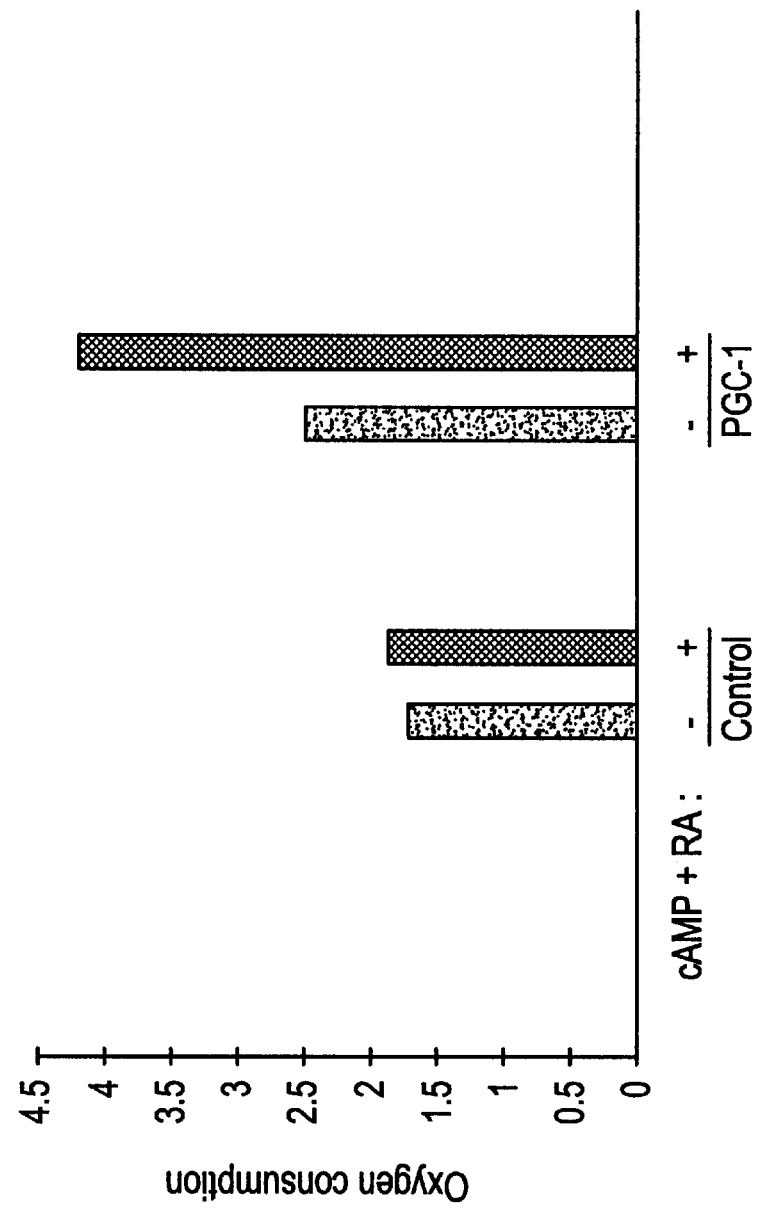

FIG. 7A human PGC-1 nucleotide sequence

```
CAGGTGGCTGGTGCCTGCATGAGTGTGTGCTCTGTGTCACTGTGTGGAGTTGAAAAGCTTGACTGGC
GTCATTCAGGAGCTGGATGGCGTGGGACATGTGCAACCAGGACTCTGAGTCTGTATGGAGTGACATCGAGTG
TGCTGCTCTGGTTGGTGAAGACCAGCCTCTTTGCCCAGATCTTCCTGAACTTGATCTTTCTGAACTAGATGT
GAACGACTTGGATACAGACAGCTTTCTGGGTGGACTCAAGTGGTGCAGTGACCAATCAGAGAATAATATCCAA
TCAGTACAACAATGAGCCTTCAAACATATTTGAGAAGATAGAAGAGAATGAGGCAAACTTGCTAGCAGT
CCTCACAGAGACACTAGACAGTCTCCCTGTGGAAGACGGATTGCCCTCATTTGATGCGCTGACAGATGG
AGAGCGTGACCACTGACAATGAGGCTAGTCCTTCCTACTGGCACCCTCCAGCTCAGCTAAGTTATAATGCAGTGG
AGAGCCGTCTCTACTTAAGAGTCAAATCACAATCACAGGATCAGAGCAAACCCTGCAATTGTTAAGACTGAGAA
TCTCAGTACCCAGAAGAACCATGCAAATCACAATCACAGGATCAGAACAAACCCTGCAATTGTTAAGACTGAGAA
TTCAGTGGAGCAATAAAGCGAAGAGTATTTGTCAACAGCACAGTCCCTGCTCGGAGCTTCT
CAAATATCTGACCACAAAGAAGTCCCACAGACCCTCCACACACAGATCGCAGAACAGCAGAGACAA
ATGCACCTCCAAAAGATCTGACCACAAAGAAGTCCCACAGACCCTCCACAACACTTACAAGCCAAACAACTTATC
TCTTCCTCTGACCCCCAGAGTCTCTGGAACTGCAGGCCCTAACTCCACCACACTCCTCATTTGAGAACAAGACTATTGAACGCAC
CTTAAGTGTGAACTCTCTGGAACTGCAGGCCCTAACTCCCAAGACTGTGGTGCCACCACATCAAAGAAGCC
TAACCCTTTTAGGGCTTCTCCAAAGCTACACAAGGCAATAACTCCACCAGGAAAGGCCGGAGCAATCCGAGTTGTA
CAGGTACAACTCAGCAAGTCCTCAGTCCTACTGGTGACACGAGGAAAGAAGAACATACTCATTAATATCACAGGA
TGCACAACTCAGCAAGTCCTCAGTCCTACTGGTGACACGAGGAAAGAAGAACGGAAATACTCATTAATATCACAGGA
GCTGTTTGGTGACCATGACTATTGCCAGTCAATTAATTCCAAAACGGAAATACTCATTAATATCACAGGA
GCTCCAAGACTCTAGACAACTAGAAAATAAAGATGTCTCCTCTGATTGGCAGGGCAGATTTGTTCTTCCAC
```

FIG. 7B

```
AGATTCAGACCAGTGCTACCTGAGAGACTTTGGAGGCAAGCAGGTCTCTCCTTGCAGCACAAGAAA
ACAGCTCCAAGACCAGGAAATCCGAGCCGAGCTGAACAAGCACTTCGGTCATCCAGTCAAGCTGTTTTGA
CGACGAAGCAGACAAGACCGGTGAACTGAGGGACAGTGATTTCAGTGAACAATTCTCCAAACTACCTAT
GTTTATAAATTCAGGACTAGCCATGGATGGCCTGTTTGATGACAGCGAAGATAAAAGTGATAAACTGAGCTA
CCCTTGGGATGCCACGCAATCCTATTCATTGTTCAATGTGTCTCCTTCTGTTCTTCTTTTAACTCTCCATG
TAGAGATTCTGTGTCACCAGGTCGTGTTCCCAAATCCTTATTTCTCAAAGACCCCAAAGGATGCGCTCTCGTTCAAGGTC
CTTTTCTCGACACAGTCGTGTTCCCGATCACCACCAAGGTCAAGGATCAAGCACCGAAATTCTCCCTGTA
CTCTTCAAGATCACGTTCAAGATCGCCCTACAGCCGTCGGCCAGGTATGACAGCCTACGAGGAATATCAGCACGA
TGTGAGATCACGTTCAAGATCGCCCTACAGCCGTCGGCCAGGTATGACAGCCTACGAGGAGCAAAGGGAGAG
GAGGCTGAAGAGGGAAGGCAATTCAGAGAGCGCCGTGTGATTTATGTGAAATTGAGGAGTGCACAGTAAATCTGCGGGATGATGGACAGGAC
GCAGAGGCAGAACGTTGCATTCGTTGAGAGTTTTGGTGAAATTGAGAGTGCACAGTAAATCTGCGGGATGATGGAGA
AGAACTGAGGGACCGTTTCATTACCTACCGTTATACCGTTTTGAGCGTACTTTTGACGCAAGTAATTTTCAAGTCTAACTATGCAGA
CAGCTATGGTTTCATTACCTACCGTTATACCGTTTTGAGCGTACTTTTGACGCAAGTAATTTTCAAGTCTAACTATGCAGA
CAGGTCAAACGAAACTCAGATGACTTTGACCCTGCTTCCACCAGGTAACATGTTCCCTAGCTGAGGATGACAGAGGATGGCG
CCTAGATTCAAACTCAAAGAAGCTTCAGATGACTTTGACCCTGCTTCCACCAGGTAACATGTTCCCTAGCTGAGGATGACAGAGGATGGCG
TTTACTGAAAGAAGCTCAGAGCGCTCCCTAAAGACTATTGCGCAGTAACATGTTCCCTAGCTGAGGATGACAGAGGATGGCG
AATACCTCATGGGACAGCGCGTCCTCCCTAAAGACTATTGCGCAGTAACATGTTCCCTAGCAGTCATACTTAGGAATTTCTCCTACTTTA
CACTCTCTGTACAAAACAAAACAAAACAAGAGAGCAAGACAGAATATCCAGTAAGCACATGTTTATTCATGGTG
TTACATGAACAGCTGCTGAAGAGCTCTCTGGAGTCTTGGTGTGCATGGAGTGTGCGTGTGTGCATGTATTATTCATGGTG
TCAGCTTTGCTTTGTGTCTTGGTGTTGGTTTAGGGAAGTATGTGGGGTACATGTGAGGACTGAAAACCTAAAACACTTAAAAAAAAAAAA
GTGTGTGTGTGTGTCTTGGTGTTGGTTTAGGGAAGTATGTGGGGTACATGTGAGGACTGAAAACCTAAAACACTTAAAAAAAAAAAA
AATGCGCAAGGGCAAACCATTTCAAAATGCCAGTTCCATGAAGACACACTTAAAACCTAGAACTTCAAAA
TGTTCGTATTCTATTCAAAAGGAAAAATATATATATATATATATATAAATTAAAAAAAAAAAA
```

FIG. 8

Amino-Acid sequence of hPGC-1:

MAWDMCNQDSESVWSDIECAALVGEDQPLCPDLPELDLSELDVNDLDTDSFLGGLKWCSD
QSEIISNQYNNEPSNIFEKIDEENEANLLAVLTETLDSLPVDEDGLPSFDALTDGDVTTD
NEASPSSMPDGTPPPQEAEEPSLLKKLLLAPANTQLSYNECSGLSTQNHANHNHRIRTNP
AIVKTENSWSNKAKSICQQKPQRRPCSELLKYLTTNDDPPHTKPTENRNSSRDKCTSKK
KSHTQSQHLQAKPTTLSLPLTPESPNDPKGSPFENKTIERTLSVELSGTAGLTPPTTP
PHKANQDNPFRASPKLKSSCKTVVPPSKKPRYSESSGTQGNNSTKKGPEQSELYAQLSK
SSVLTGGHEERKTKRPSLRLFGDHDYCQSINSKTEILINISQELQDSRQLENKDVSSDWQ
GQICSSTDSDQCYLRETLEASKQVSPCSTRKQLQDQEIRAELNKHFGHPSQAVFDDEADK
TGELRDSDFSNEQFSKLPMFINSGLAMDGLFDDSEDKSDKLSYPWDGTQSYSLFNVSPSC
SSFNSPCRDSVSPPKSLFSQRPQRMRSRSRSFSRHRSCSRSPYSRSRSRSPGSRSSSRSC
YYYESSHYRHRTHRNSPLYVRSRSRSPYSRRPRYDSYEEYQHERLKREEYRREYEKRESE
RAKQRERQRQKAIEERRVIYVGKIRPDTTRTELRDRFEVFGEIEECTVNLRDDGDSYGFI
TYRYTCDAFAALENGYTLRRSNETDFELYFCGRKQFFKSNYADLDSNSDDFDPASTKSKY
DSLDFDSLLKEAQRSLRR

FIG. 9A

Comparison hPGC-1/mPGC-1: Alignment performed with the BLAST software from the NCBI.
94% Identities

```
hPGC-1:   1  MAWDMCNQDSESVWSDIECAALVGEDQPLCPDLPELDLSELDVNDLDTDSFLGGLKWCSD  60
             MAWDMC +QDS   VWSDIECAALVGEDQPLCPDLPELDLSELDVNDLDTDSFLGGLKWCSD
mPGC-1:   1  MAWDMCSQDS--VWSDIECAALVGEDQPLCPDLPELDLSELDVNDLDTDSFLGGLKWCSD  58 hPGC-1:  61  QSEIISNQYNNEPSNIFEKIDEENEANLLAVLTETLDSLPVDEDGLPSFDALTDGDVTTD  120
             QSEIISNQYNNEP+NIFEKIDEENEANLLAVLTETLDSLPVDEDGLPSFDALTDG VTTD
mPGC-1:  59  QSEIISNQYNNEPANIFEKIDEENEANLLAVLTETLDSLPVDEDGLPSFDALTDGAVTTD  118 hPGC-1: 121  NEASPSSMPDGTPPPQEAEEPSLLKKLLLAPANTQLSYNECSGLSTQNHA-NHNHRIRTN  179
             NEASPSSMPDGTPPPQEAEEPSLLKKLLLAPANTQLSYNECSGLSTQNHA  NH HRIRTN
mPGC-1: 119  NEASPSSMPDGTPPPQEAEEPSLLKKLLLAPANTQLSYNECSGLSTQNHAANHTHRIRTN  178 hPGC-1: 180  PAIVKTENSWSNKAKSICQQQKPQRRPCSELLKYLTTNDDPPHTKPTENRNSSRDKCTSK  239
             PAIVKTENSWSNKAKSICQQQKPQRRPCSELLKYLTTNDDPPHTKPTENRNSSRDKC SK
mPGC-1: 179  PAIVKTENSWSNKAKSICQQQKPQRRPCSELLKYLTTNDDPPHTKPTENRNSSRDKCASK  238 hPGC-1: 240  KKSHTQSQSQHLQAKPTTLSLPLTPESPNDPKGSPFENKTIERTLSVELSGTAGLTPPTT  299
             KKSHTQ QSQH QAKPTTLSLPLTPESPNDPKGSPFENKTIERTLSVELSGTAGLTPPTT
mPGC-1: 239  KKSHTQPQSQHAQAKPTTLSLPLTPESPNDPKGSPFENKTIERTLSVELSGTAGLTPPTT  298
```

FIG. 9B

```
hPGC-1:  300  PPHKANQDNPFRASPKLKSSCKTVVPPPSKKPRYSESSGTQGNNSTKKGPEQSELYAQLS  359
              PPHKANQDNPF+ASPKLK  SCKTVVPP+K+ RYSE SGTQG++STKKGPEQSELYAQLS
mPGC-1:  299  PPHKANQDNPFKASPKLKPSCKTVVPPTKRARYSECSGTQGSHSTKKGPEQSELYAQLS  358 hPGC-1:  360  KSSVLTGGHEERKTKRPSLRLFGDHDYCQSINSKTEILINISQELQDSRQLENKDVSSDW  419
              KSS L+ GHEERKTKRPSLRLFGDHDYCQS+NSKT+ILINISQELQDSRQL+ KD S DW
mPGC-1:  359  KSSGLSRGHEERKTKRPSLRLFGDHDYCQSLNSKTDILINISQELQDSRQLDFKDASCDW  418 hPGC-1:  420  QGQICSSTDSDQCYLRETLEASKQVSPCSTRKQLQDQEIRAELNKHFGHPSQAVFDDEAD  479
              QG ICSSTDS QCYLRETLEASKQVSPCSTRKQLQDQEIRAELNKHFGHP QAVFDD++D
mPGC-1:  419  QGHICSSTDSGQCYLRETLEASKQVSPCSTRKQLQDQEIRAELNKHFGHPCQAVFDDKSD  478 hPGC-1:  480  KTGELRDSDFSNEQFSKLPMFINSGLAMDGLFDDSEDKSDKLSYPWDGTQSYSLFNVSPS  539
              KT ELRD DFSNEQFSKLP+FINSGLAMDGLFDDSED+SDKLSYPWDGTQ YSLF+VSPS
mPGC-1:  479  KTSELRDGDFSNEQFSKLPVFINSGLAMDGLFDDSEDESDKLSYPWDGTQPYSLFDVSPS  538 hPGC-1:  540  CSSFNSPCRDSVSPPKSLFSQRPQRMRSRSRSFSRHRSCSRSPYSRSRSRSPGSRSSSSRS  599
              CSSFNSPCRDSVSPPKSLFSQRPQRMRSRSRSFSRHRSCSRSPYSRSRSRSPGSRSSSSRS
mPGC-1:  539  CSSFNSPCRDSVSPPKSLFSQRPQRMRSRSRSFSRHRSCSRSPYSRSRSRSPGSRSSSSRS  598
```

FIG. 9C

```
hPGC-1:  600  CYYYESSHYRHRTHRNSPLYVRSRSPYSRRPRYDSYEEYQHERLKREEYRREYEKRES  659
              CYYYESSHYRHRTHRNSPLYVRSRSPYSRRPRYDSYE  Y+HERLKR+EYR+E+EKRES
mPGC-1:  599  CYYYESSHYRHRTHRNSPLYVRSRSPYSRRPRYDSYEAYEHERLKRDEYRKEHEKRES  658 hPGC-1:  660  ERAKQRERQRQKAIEERRVIYVGKIRPDTTRTELRDRFEVFGEIEECTVNLRDDGDSYGF  719
              ERAKQRERQ+QKAIEERRVIYVGKIRPDTTRTELRDRFEVFGEIEECTVNLRDDGDSYGF
mPGC-1:  659  ERAKQRERQKQKAIEERRVIYVGKIRPDTTRTELRDRFEVFGEIEECTVNLRDDGDSYGF  718 hPGC-1:  720  ITYRYTCDAFAALENGYTLRRSNETDFELYFCGRKQFFKSNYADLDSNSDDFDPASTKSK  779
              ITYRYTCDAFAALENGYTLRRSNETDFELYFCGRKQFFKSNYADLD+NSDDFDPASTKSK
mPGC-1:  719  ITYRYTCDAFAALENGYTLRRSNETDFELYFCGRKQFFKSNYADLDTNSDDFDPASTKSK  778 hPGC-1:  780  YDSLDFDSLLKEAQRSLRR  798
              YDSLDFDSLLKEAQRSLRR
mPGC-1:  779  YDSLDFDSLLKEAQRSLRR  797
```

PGC-1, A NOVEL BROWN FAT PPARγ COACTIVATOR

RELATED APPLICATIONS

This application is a continuation application of U.S. Application Ser. No. 09/900,236, filed on Jul. 5, 2001, which is a divisional application of U.S. Application Ser. No. 09/203,453, filed on Dec. 1, 1998, now U.S. Pat. No. 6,426,411 allowed, which is a continuation-in-part of U.S. application Ser. No. 09/086,912, filed on May 29, 1998, now U.S. Pat. No. 6,166,192, which claims the benefit of U.S. Provisional Application Ser. No. 60/048,107, filed on May 30, 1997, the contents of all of which are incorporated herein by reference.

GOVERNMENT SUPPORT

Work described herein was supported under grant 5R37DK31405 awarded by the National Institutes of Health. The U.S. government therefore may have certain rights in this invention.

BACKGROUND OF THE INVENTION

Vertebrates possess two distinct types of adipose tissue: white adipose tissue (WAT) and brown adipose tissue (BAT). WAT stores and releases fat according to the nutritional needs of the animal. BAT burns fat, releasing the energy as heat (i.e., nonshivering heat). The unique thermogenic properties of BAT reflect the activities of specialized mitochondria that contain the brown adipocyte-specific gene product uncoupling protein (UCP). Sears, I. B. et al. (1996) Mol. Cell. Biol. 16(7):3410–3419. UCP is a mitochondrial proton carrier that uncouples respiration from oxidative phosphorylation by collapsing the proton gradient established from fatty acid oxidation without concomitant ATP synthesis (Nicholls, D. and Locke, R. (1984) Physiol. Rev. 64:1–64).

UCP expression is tightly regulated, primarily by sympathetic nervous systems, in response to physiological signals, such as cold exposure and excess caloric intake (Girardier, L. and Seydoux, J. (1986) "Neural Control of Brown Adipose Tissue" In P. Trayhurn and D. Nichols (eds.) Brown Adipose Tissue (Arnold, London, 1986) pp. 122–151. Norepinephrine released from the local neurons interacts with β-adrenergic receptors on the brown adipocyte cell membrane, causing an increase in intracellular cyclic AMP (cAMP) levels (Sears, I. B. et al. (1996) Mol. Cell. Biol. 16(7):3410–3419). An increased level of transcription of the UCP gene is a critical component in the cascade of events leading to elevated BAT thermogenesis in response to increased cAMP (Kopecky, J. et al. (1990) J. Biol. Chem. 265:22204–22209; Rehnmark, S. M. et al. (1990) J. Biol. Chem. 265:16464–16471; Ricquier, D. F. et al. (1986) J. Biol. Chem. 261:13905–13910). BAT thermogenesis is used both (1) to maintain homeothermy by increasing thermogenesis in response to lower temperatures and (2) to maintain energy balance by increasing energy expenditure in response to increases in caloric intake (Sears, I. B. et al. (1996) Mol. Cell. Biol. 16(7):3410–3419). Nearly all experimental rodent models of obesity are accompanied by diminished or defective BAT function, usually as the first symptom in the progression of obesity (Himms-Hagen, J. (1989) Prog. Lipid Res. 28:67–115; Himms-Hagen, J. (1990) FASEB J. 4:2890–2898). In addition, ablation of BAT in transgenic mice by targeted expression of a toxin gene results in obesity (Lowell, B. et al. (1993) Nature 366:740–742). Thus, the growth and differentiation of brown adipocytes are key determinants in an animal's ability to maintain energy balance and prevent obesity (Sears, I. B. et al. (1996) Mol. Cell. Biol. 16(7):34100–3419).

Recently, several transcription factors have been identified which promote adipogenesis. These transcription factors include CCAAT/enhancer binding protein (C/EBP) α, β, and δ and peroxisome proliferator activated receptor (PPAR)γ. See Spiegelman, B. M. and Flier, J. S. (1996) Cell 87:377–389 for a review. C/EBP family members such as C/EBPα, β, and δ play important roles in the regulation of adipocyte-specific gene expression. For example, C/EBPα can transactivate the promoters of several genes expressed in the mature adipocyte (Herrera, R. et al. (1989) Mol. Cell. Biol. 9:5331–5339; Miller, S. G. et al. (1996) PNAS 93:5507–551; Christy, R. J. et al. (1989) Genes Dev. 3:1323–1335; Umek, R. M. et al. (1991) Science 251:288–291; Kaestner, K. H. et al. (1990) PNAS 87:251–255; Delabrousse, F. C. et al. (1996) PNAS 93:4096–4101; Hwang, C. S. et al. (1996) PNAS 93:873–877). Overexpression of C/EBP α can induce adipocyte differentiation in fibroblasts (Freytag, S. O. et al. (1994) Genes Dev. 8:1654–1663) whereas expression of antisense C/EBPα inhibits terminal differentiation of preadipocytes (Lin, F. T and Lane, M. D. (1992) Genes Dev. 6:533–544). The physiological importance of C/EBPα was further demonstrated by the generation of transgenic, C/EBPα-knockout mice. Although adipocytes are still present in these animals, they accumulate much less lipid and exhibit decreased adipocyte-specific gene expression (Wang, N. et al. (1995) Science 269:1108–1112). C/EBPα was found to have a synergistic relationship with another transcription factor, PPARγ, in promoting adipocyte differentiation (See Brun, R. P. et al. (1996) Curr. Opin. Cell Biol. 8:826–832 for a review). PPARγ is a nuclear hormone receptor which exists in two isoforms (γ1 and γ2) formed by alternative splicing (Zhu, Y. et al. (1995) PNAS 92:7921–7925 ) and which appears to function as both a direct regulator of many fat-specific genes and also as a "master" regulator that can trigger the entire program of adipogenesis (Spiegelman, B. M. and Flier, J. S. (1996) Cell 87:377–389). PPARγ forms a heterodimer with RXRα and has been shown to bind directly to well characterized fat-specific enhancers from the adipocyte P2 (aP2: Tontonoz, P. (1994) Genes Dev. 8:1224–1234) and phosphoenolpyruvate carboxykinase (PEPCK) genes (Tontonoz, P. (1994) Mol. Cell. Biol. 15:351–357).

Although the UCP gene promoter includes binding sites for C/EBP (Yubero, P. et al. (1994) Biochem. Biophys. Res. Commun. 198:653–659) and a PPARγ-responsive element (Sears, I. B. et al. (1996) Mol. Cell. Biol. 16(7):3410–3419), C/EBP and PPARγ do not seem to be sufficient to induce UCP expression (Sears, I. B. et al. (1996) Mol. Cell. Biol. 16(7):3410–3419). It would be highly desirable, therefore, to identify a possible additional factor which acts in combination with either C/EBP or PPARγ to activate UCP expression and thus to promote BAT thermogenesis.

SUMMARY OF THE INVENTION

This invention is based, at least in part, on the discovery of nucleic acid molecules which encode a family of novel molecules which can act in combination with PPARγ as a coactivator of UCP expression in BAT. These molecules are referred to herein as PPARγ Coactivator 1 ("PGC-1") proteins. Nucleic acid molecules encoding PGC-1 proteins are referred to herein as PGC-1 nucleic acid molecules. The PGC-1 molecules of the invention are capable of, for example, modulating adipogenesis, e.g., brown adipogenesis, and thermogenesis of a PGC-1 expressing tissue, e.g., BAT or muscle. Other functions of a PGC-1 family member of the invention are described throughout the present application.

Accordingly, one aspect of the invention pertains to isolated nucleic acid molecules (e.g., cDNAs) comprising a nucleotide sequence encoding a PGC-1 protein or portions thereof (e.g., biologically active or antigenic portions), as well as nucleic acid fragments suitable as primers or hybridization probes for the detection of PGC-1-encoding nucleic acid (e.g., mRNA). In particularly preferred embodiments, the isolated nucleic acid molecule comprises the nucleotide sequence of SEQ ID NO:1, SEQ ID NO:4 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence of SEQ ID NO:1, SEQ ID NO:4, or the coding region or a complement of either of these nucleotide sequences.

In other particularly preferred embodiments, the isolated nucleic acid molecule of the invention comprises a nucleotide sequence which hybridizes to or is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO:1, SEQ ID NO:4 or a portion (e.g., 400, 450, 500, or more nucleotides) of this nucleotide sequence.

In yet another preferred embodiment, the nucleic acid molecule includes a nucleotide sequence encoding a protein having the amino acid sequence of SEQ ID NO: 2, SEQ ID NO:5. In yet another preferred embodiment, the nucleic acid molecule is at least 487 nucleotides in length. In another preferred emnbodiment, the nucleic acid molecule comprises a fragment of at least 487 nucleotides of the nucleotide sequence of SEQ ID NO:1, SEQ ID NO:4 or a complement thereof. In a further preferred embodiment, the nucleic acid molecule is at least 487 nucleotides in length and encodes a protein having an PGC-1 activity (as described herein).

Another embodiment of the invention features nucleic acid molecules, preferably PGC-1 nucleic acid molecules, which specifically detect PGC-1 nucleic acid molecules relative to nucleic acid molecules encoding non-PGC-1 proteins. For example, in one embodiment, such a nucleic acid molecule is at least 350, 400, 450, or 487 nucleotides in length and hybridizes under stringent conditions to a nucleic acid molecule comprising the nucleotide sequence shown in SEQ ID NO:1, SEQ ID NO:4, or a complement thereof. In a particularly preferred embodiment, the nucleic acid molecule comprises a fragment of at least 487 nucleotides of the nucleotide sequence of SEQ ID NO:1, SEQ ID NO:4, or a complement thereof. In preferred embodiments, the nucleic acid molecules are at least 15 (e.g., contiguous) nucleotides in length and hybridize under stringent conditions to nucleotides 10214, 316, 515–532, 895–1279, 1427–1456, 2325–2387 of SEQ ID NO:1. In other preferred embodiments, the nucleic acid molecules include nucleotides 1–28, 50–232, 518–535, 895–1219, 2325–2386, 2975–3023 of SEQ ID NO:4.

In other preferred embodiments, the isolated nucleic acid molecule encodes the amino acid sequence of SEQ ID NO:2, SEQ ID NO:5 or an amino acid sequence which is at least about 50%, preferably at least about 60%, more preferably at least about 70%, yet more preferably at least about 80%, still more preferably at least about 90%, and most preferably 95% or more homologous to the amino acid sequence of SEQ ID NO:2, SEQ ID NO:5. The preferred PGC-1 proteins of the present invention also preferably possess at least one of the PGC-1 biological activities described herein.

In another embodiment, the isolated nucleic acid molecule encodes a protein or portion thereof wherein the protein or portion thereof includes an amino acid sequence which is sufficiently homologous to an amino acid sequence of SEQ ID NO:2, SEQ ID NO:5, e.g., sufficiently homologous to an amino acid sequence of SEQ ID NO:2, SEQ ID NO:5 such that the protein or portion thereof maintains a PGC-1 activity. Preferably, the protein or portion thereof encoded by the nucleic acid molecule maintains one or more of the following biological activities: 1) it can interact with (e.g., bind to) PPARγ; 2) it can modulate PPARγ activity; 3) it can modulate UCP expression; 4) it can modulate thermogenesis in adipocvtes, e.g., thermogenesis in brown adipocytes, or muscle; 5) it can modulate oxygen consumption in adipocytes or muscle; 6) it can modulate adipogenesis, e.g., differentiation of white adipocytes into brown adipocytes; 7) it can modulate insulin sensitivity of cells, e.g., insulin sensitivity of muscle cells, liver cells, adipocytes; 8) it can interact with (e.g., bind to) nuclear hormone receptors, e.g., the thyroid hormone receptor, the estrogen receptor, the retinoic acid receptor; 9) it can modulate the activity of nuclear hormone receptors; and 10) it can interact with (e.g., bind to) the transcription factor C/EBPα. In one embodiment, the protein encoded by the nucleic acid molecule is at least about 50%, preferably at least about 60%, more preferably at least about 70%, yet more preferably at least about 80%, still more preferably at least about 90%, and most preferably at least about 95% or more homologous to the amino acid sequence of SEQ ID NO:2, SEQ ID NO:5 (e.g., the entire amino acid sequence of SEQ ID NO:2, SEQ ID NO:5).

In yet another embodiment, the isolated nucleic acid molecule is derived from a human and encodes a portion of a protein which includes one or more of the following domains or motifs: a tyrosine phosphorylation site, a cAMP phosphorylation site, a serine-arginine (SR) rich domain, an RNA binding motif, and an LXXLL (SEQ ID NO:3) motif which mediates interaction with a nuclear receptor. In another preferred embodiment, the isolated nucleic acid molecule is derived from a human and encodes a protein (e.g., a PGC-1 fusion protein) which includes one or more of the domains/motifs described herein and which has one or more of the following biological activities: 1) it can interact with (e.g., bind to) PPARγ; 2) it can modulate PPARγ activity; 3) it can modulate UCP expression; 4) it can modulate thermogenesis in adipocytes, e.g., thermogenesis in brown adipocytes, or muscle; 5) it can modulate oxygen consumption in adipocytes or muscle; 6) it can modulate adipogenesis, e.g., differentiation of white adipocytes into brown adipocytes; 7) it can modulate insulin sensitivity of cells, e.g., insulin sensitivity of muscle cells, liver cells, adipocytes; 8) it can interact with (e.g., bind to) nuclear hormone receptors, e.g., the thyroid hormone receptor, the estrogen receptor, the retinoic acid receptor; 9) it can modulate the activity of nuclear hormone receptors; and 10) it can interact with (e.g., bind to) the transcription factor C/EBPα.

In another embodiment, the isolated nucleic acid molecule is at least 15 nucleotides in length and hybridizes under stringent conditions to a nucleic acid molecule comprising the nucleotide sequence of SEQ ID NO:1, SEQ ID NO:4 or to a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO:1, SEQ ID NO:4. Preferably, the isolated nucleic acid molecule corresponds to a naturally-occurring nucleic acid molecule. More preferably, the isolated nucleic acid encodes naturally-occurring human PGC-1 or a biologically active portion thereof. Moreover, given the disclosure herein of a PGC-1-encoding cDNA sequence (e.g., SEQ ID NO:1, SEQ ID NO:4), antisense nucleic acid molecules (i.e., molecules which are complementary to the coding strand of the PGC-1 cDNA sequence) are also provided by the invention.

Another aspect of the invention pertains to vectors, e.g., recombinant expression vectors, containing the nucleic acid molecules of the invention and host cells into which such vectors have been introduced. In one embodiment, such a host cell is used to produce PGC-1 protein by culturing the host cell in a suitable medium. If desired, the PGC-1 protein can be then isolated from the medium or the host cell.

Yet another aspect of the invention pertains to transgenic nonhuman animals in which a PGC-1 gene has been introduced or altered. In one embodiment, the genome of the nonhuman animal has been altered by introduction of a nucleic acid molecule of the invention encoding PGC-1 as a transgene. In another embodiment, an endogenous PGC-1 gene within the genome of the nonhuman animal has been altered, e.g., functionally disrupted, by homologous recombination.

Still another aspect of the invention pertains to an isolated PGC-1 protein or a portion, e.g., a biologically active portion, thereof. In a preferred embodiment, the isolated PGC-1 protein or portion thereof can modulate thermogenesis in BAT. In another preferred embodiment, the isolated PGC-1 protein or portion thereof is sufficiently homologous to an amino acid sequence of SEQ ID NO:2, SEQ ID NO:5 such that the protein or portion thereof maintains one or more of the following biological activities: 1) it can interact with (e.g., bind to) PPARγ; 2) it can modulate PPARγ activity; 3) it can modulate UCP expression; 4) it can modulate thermogenesis in adipocytes, e.g., thermogenesis in brown adipocytes, or muscle; 5) it can modulate oxygen consumption in adipocytes or muscle; 6) it can modulate adipogenesis, e.g., differentiation of white adipocytes into brown adipocytes; 7) it can modulate insulin sensitivity of cells, e.g., insulin sensitivity of muscle cells, liver cells, adipocytes; 8) it can interact with (e.g., bind to) nuclear hormone receptors, e.g., the thyroid hormone receptor, the estrogen receptor, the retinoic acid receptor; 9) it can modulate the activity of nuclear hormone receptors; and 10) it can interact with (e.g., bind to) the transcription factor C/EBPα.

In one embodiment, the biologically active portion of the PGC-1 protein includes a domain or motif, preferably a domain or motif which has a PGC-1 biological activity. The domain or motif can be a tyrosine phosphorylation site, a cAMP phosphorylation site, a serine-arginine (SR) rich domain, an RNA binding motif, and an LXXLL (SEQ ID NO:3) motif which mediates interaction with a nuclear receptor, or a combination of one or more of these domains or motifs. Preferably, the biologically active portion of the PGC-1 protein which includes one or more of these domains or motifs has one of the following biological activities: 1) it can interact with (e.g., bind to) PPARγ; 2) it can modulate PPARγ activity; 3) it can modulate UCP expression; 4) it can modulate thermogenesis in adipocytes, e.g., thermogenesis in brown adipocytes, or muscle; 5) it can modulate oxygen consumption in adipocytes or muscle; 6) it can modulate adipogenesis, e.g., differentiation of white adipocytes into brown adipocytes; 7) it can modulate insulin sensitivity of cells, e.g., insulin sensitivity of muscle cells, liver cells, adipocytes; 8) it can interact with (e.g., bind to) nuclear hormone receptors, e.g., the thyroid hormone receptor, the estrogen receptor, the retinoic acid receptor; 9) it can modulate the activity of nuclear hormone receptors; and 10) it can interact with (e.g., bind to) the transcription factor C/EBPα.

The invention also provides an isolated preparation of a PGC-1 protein. In preferred embodiments, the PGC-1 protein comprises the amino acid sequence of SEQ ID NO:2, SEQ ID NO:5 or an amino acid sequence which is at least about 50%, preferably at least about 60%, more preferably at least about 70%, yet more preferably at least about 80%, still more preferably at least about 90%, and most preferably at least about 95% or more homologous to the amino acid sequence of SEQ ID NO:2, SEQ ID NO:5, e.g., the entire amino acid sequence of SEQ ID NO:2, SEQ ID NO:5. In other embodiments, the isolated PGC-1 protein comprises an amino acid sequence which is at least about 50%, preferably at least about 60%, more preferably at least about 70%, yet more preferably at least about 80%, still more preferably at least about 90%, and most preferably at least about 95% or more homologous to the amino acid sequence of SEQ ID NO:2, SEQ ID NO:5 and has one or more of the PGC-1 biological activities described herein. Alternatively, the isolated PGC-1 protein can comprise an amino acid sequence which is encoded by a nucleotide sequence which hybridizes, e.g., hybridizes under stringent conditions, or is at least about 50%, preferably at least about 60%, more preferably at least about 70%, yet more preferably at least about 80%, still more preferably at least about 90%, and most preferably at least about 95% or more homologous to the nucleotide sequence of SEQ ID NO:1, SEQ ID NO:4. It is also preferred that the preferred forms of PGC-1 also have one or more of the PGC-1 biological activities described herein.

The PGC-1 protein (or polypeptide) or a biologically active portion thereof can be operatively linked to a non-PGC-1 polypeptide to form a fusion protein. In addition, the PGC-1 protein or a biologically active portion thereof can be incorporated into a pharmaceutical composition comprising the protein and a pharmaceutically acceptable carrier.

The PGC-1 protein of the invention, or portions or fragments thereof, can be used to prepare anti-PGC-1 antibodies. Accordingly, the invention also provides an antigenic peptide of PGC-1 which comprises at least 8 amino acid residues of the amino acid sequence shown in SEQ ID NO:2, SEQ ID NO:5 (or an amino acid sequence which is at least about 50% homologous to the amino acid sequence of SEQ ID NO:2, SEQ ID NO:5) and encompasses an epitope of PGC-1 such that an antibody raised against the peptide forms a specific immune complex with PGC-1. Preferably, the antigenic peptide comprises at least 10 amino acid residues, more preferably at least 15 amino acid residues, even more preferably at least 20 amino acid residues, and most preferably at least 30 amino acid residues. The invention further provides an antibody that specifically binds PGC-1. In one embodiment, the antibody is monoclonal. In another embodiment, the antibody is coupled to a detectable substance. In yet another embodiment, the antibody is incorporated into a pharmaceutical composition comprising the antibody and a pharmaceutically acceptable carrier.

Another aspect of the invention pertains to methods for modulating a cell associated activity, e.g., proliferation, differentiation, survival, thermogenesis, oxygen consump tion. Such methods include contacting the cell with an agent which modulates PGC-1 protein activity or PGC-1 nucleic acid expression such that a cell associated activity is altered relative to a cell associated activity (e.g., the same cell associated activity) of the cell in the absence of the agent. In a preferred embodiment, the cell associated activity is thermogenesis and the cell is a brown adipocyte. The agent which modulates PGC-1 activity can be an agent which stimulates PGC-1 protein activity or PGC-1 nucleic acid expression. Examples of agents which stimulate PGC-1 protein activity or PGC-1 nucleic acid expression include small molecules, active PGC-1 proteins, and nucleic acids encoding PGC-1 that have been introduced into the cell. Examples of agents which inhibit PGC-1 activity or expression include small molecules, antisense PGC-1 nucleic acid molecules, and antibodies that specifically bind to PGC-1. In a preferred embodiment, the cell is present within a subject and the agent is administered to the subject.

The present invention also pertains to methods for treating subjects having various disorders. For example, the invention pertains to methods for treating a subject having a disorder characterized by aberrant PGC-1 protein activity or nucleic acid expression such as a weight disorder, e.g., obesity, anorexia, cachexia, or a disorder associated with insufficient insulin activity, e.g., diabetes. These methods include administering to the subject a PGC-1 modulator (e.g., a small molecule) such that treatment of the subject occurs.

In one embodiment, the invention pertains to methods for treating a subject having a weight disorder, e.g., obesity, or a disorder associated with insufficient insulin activity, e.g., diabetes, comprising administering to the subject a PGC-1 activator, e.g., a PGC-1 protein or portion thereof or a compound or an agent thereby increasing the expression or activity of PGC-1 such that treatment of the disease occurs. Weight disorders, e.g., obesity, and disorders associated with insufficient insulin activity can also be treated according to the invention by administering to the subject having the disorder a PGC-1 activator, e.g., a nucleic acid encoding a PGC-1 protein or portion thereof such that treatment occurs.

The invention also pertains to methods for detecting genetic lesions in a PGC-1 gene, thereby determining if a subject with the lesioned gene is at risk for (or is predisposed to have) a disorder characterized by aberrant or abnormal PGC-1 nucleic acid expression or PGC-1 protein activity, e.g., a weight disorder or a disorder associated with insufficient insulin activity. In preferred embodiments, the methods include detecting, in a sample of cells from the subject, the presence or absence of a genetic lesion characterized by an alteration affecting the integrity of a gene encoding a PGC-1 protein, or the misexpression of the PGC-1 gene.

Another aspect of the invention pertains to methods for detecting the presence of PGC-1 in a biological sample. In a preferred embodiment, the methods involve contacting a biological sample (e.g., a cardiomyocyte, hepatocyte, neuronal cell, a brown adipocyte or a muscle sample) with a compound or an agent capable of detecting PGC-1 protein or PGC-1 mRNA such that the presence of PGC-1 is detected in the biological sample. The compound or agent can be, for example, a labeled or labelable nucleic acid probe capable of hybridizing to PGC-1 mRNA or a labeled or labelable antibody capable of binding to PGC-1 protein. The invention further provides methods for diagnosis of a subject with, for example, a weight disorder or a disorder associated with insufficient insulin activity, based on detection of PGC-1 protein or mRNA. In one embodiment, the method involves contacting a cell or tissue sample (e.g., a brown adipocyte sample) from the subject with an agent capable of detecting PGC-1 protein or mRNA, determining the amount of PGC-1 protein or mRNA expressed in the cell or tissue sample, comparing the amount of PGC-1 protein or mRNA expressed in the cell or tissue sample to a control sample and forming a diagnosis based on the amount of PGC-1 protein or mRNA expressed in the cell or tissue sample as compared to the control sample. Preferably, the cell sample is a brown adipocyte sample. Kits for detecting PGC-1 in a biological sample are also within the scope of the invention.

Still another aspect of the invention pertains to methods, e.g., screening assays, for identifying a compound for treating a disorder characterized by aberrant PGC-1 nucleic acid expression or protein activity, e.g., a weight disorder or a disorder associated with insufficient insulin activity. These methods typically include assaying the ability of the compound or agent to modulate the expression of the PGC-1 gene or the activity of the PGC-1 protein thereby identifying a compound for treating a disorder characterized by aberrant PGC-1 nucleic acid expression or protein activity. In a preferred embodiment, the method involves contacting a biological sample, e.g., a cell or tissue sample, e.g., a brown adipocyte sample, obtained from a subject having the disorder with the compound or agent, determining the amount of PGC-1 protein expressed and/or measuring the activity of the PGC-1 protein in the biological sample, comparing the amount of PGC-1 protein expressed in the biological sample and/or the measurable PGC-1 biological activity in the cell to that of a control sample. An alteration in the amount of PGC-1 nucleic acid expression or PGC-1 protein activity in the cell exposed to the compound or agent in comparison to the control is indicative of a modulation of PGC-1 nucleic acid expression and/or PGC-1 protein activity.

The invention also pertains to methods for identifying a compound or agent which interacts with (e.g., binds to) a PGC-1 protein. These methods include the steps of contacting the PGC-1 protein with the compound or agent under conditions which allow binding of the compound to the PGC-1 protein to form a complex and detecting the formation of a complex of the PGC-1 protein and the compound in which the ability of the compound to bind to the PGC-1 protein is indicated by the presence of the compound in the complex.

The invention further pertains to methods for identifying a compound or agent which modulates, e.g., stimulates or inhibits, the interaction of the PGC-1 protein with a target molecule, e.g., PPARγ, C/EBPα, a nuclear hormone receptor, e.g., the thyroid hormone receptor, the estrogen receptor, the retinoic acid receptor. In these methods, the PGC-1 protein is contacted, in the presence of the compound or agent, with the target molecule under conditions which allow binding of the target molecule to the PGC-1 protein to form a complex. An alteration, e.g., an increase or decrease, in complex formation between the PGC-1 protein and the target molecule as compared to the amount of complex formed in the absence of the compound or agent is indicative of the ability of the compound or agent to modulate the interaction of the PGC-1 protein with a target molecule.

BRIEF DESCRIPTION OF THE DRAWING

FIGS. 1A–1C depict the mouse PGC-1 nucleotide (SEQ ID NO:1) and amino acid (SEQ ID NO:2) sequence.

FIGS. 2A–2B depict an analysis of the mouse PGC-1 sequence. The following domains are underlined in FIG. 2A: SR domains (amino acids 565–598 and 617–631), an RNA-binding domain (amino acid 677–709), three consensus sites for phosphorylating protein kinase A (amino acids 238–241, 373–376 and 655–668), and an LXXLL (SEQ ID NO:3) motif (amino acids 142–146).

FIG. 2B is a schematic representation of the structure of mouse PGC-1. Arrows indicate putative protein kinase A phosphorylation sites having the consensus sequence (R, K)2x(ST). The gray box indicates the SR rich region domain and black box indicates the RNA-binding domain.

FIGS. 3A–3B are bar graphs depicting the effect of mouse PGC-1 in stimulating the transactivation of the UCP-1 promoter by PPARγ and the thyroid hormone receptor (TR). FIG. 3A depicts the increased transcription activation of the CAT reporter gene under the control of the UCP-1 promoter with respect to the indicated ligands/hormones in RAT1 IR cells. FIG. 3B is a graph depicting the increased transcription activation of a reporter CAT gene under the control of UAS sequences (five copies) using mouse PGC-1 linked to GAL4 DBD.

FIG. 6 is a bar graph depicting the effect in oxygen consumption of chronic treatment of PGC-1 infected and control cells with cAMP and Retinoic Acid (RA).

FIGS. 7A–7B depict the human PGC-1 nucleotide (SEQ ID NO:4) sequence.

FIG. 8 depicts the human PGC-1 amino acid (SEQ ID NO:5) sequence.

FIGS. 9A–9C depict an alignment between the human PGC-1 amino acid sequence (SEQ ID NO:5) and the mouse PGC-1 amino acid sequence (SEQ ID NO:2). This alignment was performed with BLAST software found at the National Center for Biotechnology Information (NCBI) web site (Altschul, S. F. et al. (1990) *J. Mol. Biol.* 215:403–410; Madden, T. L. et al. (1996) *Methods Enzymol.* 266:131–141) and it was determined that human PGC-1 has a 94% identity to mouse PGC-1.

DETAILED DESCRIPTION OF THE INVENTION

Figure 3B:
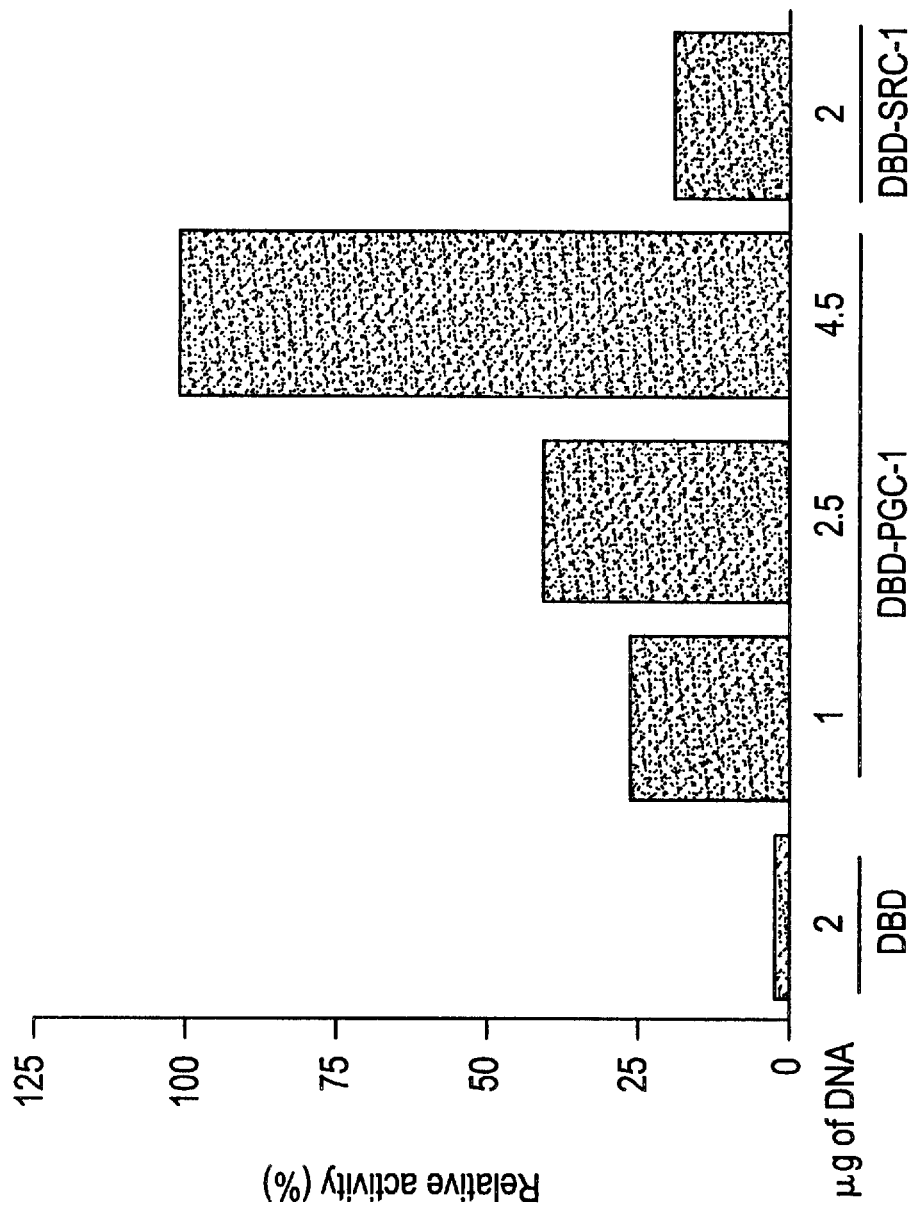

The present invention is based on the discovery of novel molecules, referred to herein as PGC-1 nucleic acid and protein molecules, which comprise a family of molecules having certain conserved structural and functional features, and which play a role in or function in adipocyte associated activities. The term "family" when referring to the protein and nucleic acid molecules of the invention is intended to mean two or more proteins or nucleic acid molecules having a common structural domain and having sufficient amino acid or nucleotide sequence homology as defined herein. Such family members can be naturally occurring and can be from either the same or different species. For example, a family can contain a first protein of human origin, as well as other, distinct proteins of human origin or alternatively, can contain homologues of non-human origin. Members of a family may also have common functional characteristics.

In one embodiment, a PGC-1 molecule can modulate adipogenesis, e.g., adipogenesis of brown adipocytes and muscle cells. In another embodiment, a PGC-1 molecule can modulate thermogenesis in brown adipocytes. For example, a PGC-1 molecule of the invention can increase thermogenesis in adipocytes of an individual, thereby promoting weight loss in the individual. Thus, a PGC-1 molecule of the invention can be used to treat obesity. Additionally, the increase in thermogenic activity caused by a PGC-1 molecule can also increase insulin sensitivity of the adipocytes as well as of muscle cells and liver cells. Thus, a PGC-1 molecule of the invention can also be used to treat disorders characterized by insufficient insulin activity such as diabetes. Alternatively, inhibition of the activity of a PGC-1 molecule of the invention can decrease thermogenesis in adipocytes of an individual, thereby inhibiting weight loss in the individual. Thus, the modulators of PGC-1 molecules of the invention can be used to treat undesirable weight loss, e.g., cachexia, anorexia. Moreover, a PGC-1 molecule of the invention can also be used as targets to screen molecules, e.g., small molecules, which can modulate PGC-1 activity. PGC-1 molecule modulators can also be used to treat weight disorders, e.g., cachexia, anorexia, obesity, or disorders characterized by insufficient insulin activity.

Mouse PGC-1 nucleic acid molecules were identified from mouse brown adipocytes based on their ability, as determined using a yeast two hybrid assay (described in Example I) to bind to PPARγ. As described above, PPARγ is a nuclear hormone receptor which functions as both a direct regulator of many fat-specific genes and also as a "master" regulator that can trigger the entire program of adipogenesis. Moreover, as the UCP gene promoter includes a PPARγ-responsive element, a modulator of PPARγ can modulate adipogenesis and UCP expression. UCP expression can result in thermogenesis.

The nucleotide sequence of the mouse and human PGC-1 cDNA and the predicted amino acid sequence of the mouse and human PGC-1 proteins are shown in FIGS. 1A, 1B, 1C, 2A, 7A, 7B, and 8, and in SEQ ID NOs:1, 2, 4, and 5, respectively. Using all or a portion of the mouse nucleotide sequence (e.g., a 5' portion of SEQ ID NO:1, e.g., nucleotides 1–50 of SEQ ID NO:1) to probe a cDNA library from a human cell line such as a human muscle, heart, kidney, or brain cell line, the human PGC-1 nucleotide sequence was obtained using routine experimentation as described in Example II. The mouse PGC-1 gene, which is approximately 3066 nucleotides in length, encodes a full length protein having a molecular weight of approximately 120 kD and which is approximately 797 amino acid residues in length. The human PGC-1 gene, which is approximately 3023 nucleotides in length, encodes a full length protein having a molecular weight of approximately 120 kD and which is approximately 798 amino acid residues in length. PGC-1 family member proteins include several domains/motifs. These domains/motifs include: two putative tyrosine phosphorylation sites (amino acid residues 204–212 and 378–385 of SEQ ID NO:2, and amino acid residues 205–213 and 379–386 of SEQ ID NO:5), three putative cAMP phosphorylation sites (amino acid residues 238–241, 373–376, and 655–658 of SEQ ID NO:2, and 239–242, 374–377, and 656–658 of SEQ ID NO:5), a serine-arginine (SR) rich domain (amino acid residues 562–600 of SEQ ID NO:2, and 563–601 of SEQ ID NO:5), an RNA binding motif (amino acid residues 656–709 of SEQ ID NO:2, and 657–710 of SEQ ID NO:5), and an LXXLL motif (amino acids 142–146 of SEQ ID NO:2, 143–147 of SEQ ID NO:5; SEQ ID NO:3) which mediates interaction with a nuclear receptor. As used herein, a tyrosine phosphorylation site is an amino acid sequence which includes at least one tyrosine residue which can be phosphorylated by a tyrosine protein kinase. Typically, a tyrosine phosphorylation site is characterized by a lysine or an arginine about seven residues to the N-terminal side of the phosphorylated tyrosine. An acidic residue (asparagine or glutamine) is often found at either three or four residues to the N-terminal side of the tyrosine (Patschinsky, T. et al. (1982) Proc. Natl. Acad. Sci. USA 79:973–977); Hunter, T. (1982) J. Biol. Chem. 257:4843–4848; Cooper, J. A. et al. (1984) J. Biol. Chem. 259:7835–7841). As used herein, a cAMP phosphorylation site is an amino acid sequence which includes a serine or threonine residue which can be phosphorylated by a cAMP-dependent protein kinase. Typically, the cAMP phosphorylation site is characterized by at least two consecutive basic residues to the N-terminal side of the serine or threonine (Fremisco, J. R. et al. (1980) J. Biol. Chem. 255:4240–4245; Glass, D. B. and Smith, S. B. (1983) J. Biol. Chem. 258:14797–14803; Glass, D. B. et al. (1986) J. Biol. Chem. 261:2987–2993). As used herein, a serine-arginine rich domain is an amino acid sequence which is rich in serine and arginine residues. Typically, SR rich domains are domains which interact with the CTD domain of RNA polymerase II or are involved in splicing functions. As used herein, an RNA binding motif is an amino acid sequence which can bind an RNA molecule or a single stranded DNA molecule. RNA binding motifs are described in Lodish, H., Darnell, J., and Baltimore, D. Molecular Cell Biology, 3rd ed (W. H. Freeman and Company, New York, N.Y., 1995). As used herein, an LXXLL (SEQ ID NO:3) refers to a motif wherein X can be any amino acid and which mediates an interaction between an nuclear receptor and a coactivator (Heery et al. (1997) Nature 397:733–736; Torchia et al. (1997) Nature 387:677–684).

The PGC-1 protein is expressed in muscle, heart, kidney, brain and brown adipose tissue but not in white adipose tissue. In tissue from cold acclimated animals, PGC-1 expression was highly induced in brown adipose tissue. Moreover, in tissue from cold acclimated animals, PGC-1 expression was brown adipose tissue specific. PGC-1 expression in tissues from cold acclimated animals parallels expression of UCP, the brown adipose tissue marker responsible for the thermogenic activity of this tissue.

The PGC-1 protein or a biologically active portion or fragment of the invention can have one or more of the following activities: 1) it can interact with (e.g., bind to) PPARγ; 2) it can modulate PPARγ activity; 3) it can modulate UCP expression; 4) it can modulate thermogenesis in adipocytes, e.g., thermogenesis in brown adipocytes, or muscle; 5) it can modulate oxygen consumption in adipocytes or muscle; 6) it can modulate adipogenesis, e.g., differentiation of white adipocytes into brown adipocytes; 7) it can modulate insulin sensitivity of cells, e.g., insulin sensitivity of muscle cells, liver cells, adipocytes; 8) it can interact with (e.g., bind to) nuclear hormone receptors, e.g., the thyroid hormone receptor, the estrogen receptor, the retinoic acid receptor; 9) it can modulate the activity of nuclear hormone receptors; and 10) it can interact with (e.g., bind to) the transcription factor C/EBPα.

Various aspects of the invention are described in further detail in the following subsections:

I. Isolated Nucleic Acid Molecules

One aspect of the invention pertains to isolated nucleic acid molecules that encode PGC-1 or biologically active portions thereof, as well as nucleic acid fragments sufficient for use as hybridization probes to identify PGC-1-encoding nucleic acid (e.g., PGC-1 mRNA). As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated PGC-1 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a brown adipocyte). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having the nucleotide sequence of SEQ ID NO:1, SEQ ID NO:4 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO:1, SEQ ID NO:4 or a portion thereof (e.g., 400, 450, 500, or more nucleotides), can be isolated using standard molecular biology techniques and the sequence information provided herein. For example, a human PGC-1 cDNA can be isolated from a human heart, kidney,. or brain cell line (from Stratagene, LaJolla, Calif., or Clontech, Palo Alto, Calif.) using all or portion of SEQ ID NO:1, SEQ ID NO:4 as a hybridization probe and standard hybridization techniques (e.g., as described in Sambrook, J., Fritsh, E. F., and Maniatis, T. Molecular Cloning: A Laboratory Manual. 2nd, ed, Cold Spring Harbor Laboratory, Cold Spring Harbor Laboratory Press, Cold Spring Harbor, N.Y., 1989). Moreover, a nucleic acid molecule encompassing all or a portion of SEQ ID NO:1, SEQ ID NO:4 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO:1, SEQ ID NO:4 can be isolated by the polymerase chain reaction using oligonucleotide primers designed based upon the sequence of SEQ ID NO:1, SEQ ID NO:4 or the homologous nucleotide sequence. For example, mRNA can be isolated from heart cells, kidney cells, brain cells, or brown adipocytes (e.g., by the guanidinium-thiocyanate extraction procedure of Chirgwin et al. (1979) Biochemistry 18: 5294–5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO:1, SEQ ID NO:4 or to the homologous nucleotide sequence. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a PGC-1 nucleotide sequence can be prepared by standard synthetic techniques, e.g., using an automated DNA synthesizer.

In a preferred embodiment, an isolated nucleic acid molecule of the invention comprises the nucleotide sequence shown in SEQ ID NO:1, SEQ ID NO:4 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO:1, SEQ ID NO:4. The sequence of SEQ ID NO:1 corresponds to the mouse PGC-1 cDNA. This cDNA comprises sequences encoding the PGC-1 protein (i.e., "the coding region", from nucleotides 92 to 2482), as well as 5' untranslated sequences (nucleotides 1 to 91) and 3' untranslated sequences (nucleotides 2483 to 3066). Alternatively, the nucleic acid molecule can comprise only the coding region of SEQ ID NO:1 (e.g., nucleotides 92 to 2482) or the homologous nucleotide sequence. The sequence of SEQ ID NO:4 corresponds to the human PGC-1 cDNA. This cDNA comprises sequences encoding the PGC-1 protein (i.e., "the coding region", from nucleotides 89 to 2482), as well as 5' untranslated sequences (nucleotides 1 to 88) and 3' untranslated sequences (nucleotides 2513 to 3023). Alternatively, the nucleic acid molecule can comprise only the coding region of SEQ ID NO:4 (e.g., nucleotides 89 to 2482) or the homologous nucleotide sequence.

In another preferred embodiment, an isolated nucleic acid molecule of the invention comprises a nucleic acid molecule which is a complement of the nucleotide sequence shown in SEQ ID NO:1, SEQ ID NO:4 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO:1, SEQ ID NO:4. A nucleic acid molecule which is complementary to the nucleotide sequence shown in SEQ ID NO:1, SEQ ID NO:4 or to a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO:1, SEQ ID NO:4 is one which is sufficiently complementary to the nucleotide sequence shown in SEQ ID NO:1, SEQ ID NO:4 or to the homologous sequence such that it can hybridize to the nucleotide sequence shown in SEQ ID NO:1, SEQ ID NO:4 or to the homologous sequence, thereby forming a stable duplex.

In still another preferred embodiment, an isolated nucleic acid molecule of the invention comprises a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO:1, SEQ ID NO:4 or a portion of this nucleotide sequence. In an additional preferred embodiment, an isolated nucleic acid molecule of the invention comprises a nucleotide sequence which hybridizes, e.g., hybridizes under stringent conditions, to the nucleotide sequence shown in SEQ ID NO:1, SEQ ID NO:4 or to a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO:1, SEQ ID NO:4.

Moreover, the nucleic acid molecule of the invention can comprise only a portion of the coding region of SEQ ID NO:1, SEQ ID NO:4 or the coding region of a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO:1, SEQ ID NO:4, for example a fragment which can be used as a probe or primer or a fragment encoding a biologically active portion of PGC-1. The nucleotide sequence determined from the cloning of the PGC-1 gene from a mouse allows for the generation of probes and primers designed for use in identifying and/or cloning other PGC-1 family members, as well as PGC-1 homologues in other cell types, e.g. from other tissues, as well as PGC-1 homologues from other mammals such as humans. The probe/primer typically comprises substantially purified oligonucleotide. The oligonucleotide typically comprises a region of nucleotide sequence that hybridizes under stringent conditions to at least about 12, preferably at least about 25, more preferably about 40, 50 or 75 consecutive nucleotides of SEQ ID NO:1, SEQ ID NO:4 sense, an anti-sense sequence of SEQ ID NO:1, SEQ ID NO:4, or naturally occurring mutants thereof. Primers based on the nucleotide sequence in SEQ ID NO:1, SEQ ID NO:4 can be used in PCR reactions to clone PGC-1 homologues.

In an exemplary embodiment, a nucleic acid molecule of the present invention comprises a nucleotide sequence which is about 100, preferably 100–200, preferably 200–300, more preferably 300–400, and even more preferably 400–487 nucleotides in length and hybridizes under stringent hybridization conditions to a nucleic acid molecule of SEQ ID NO:1, SEQ ID NO:4.

Probes based on the PGC-1 nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a diagnostic test kit for identifying cells or tissue which misexpress a PGC-1 protein, such as by measuring a level of a PGC-1-encoding nucleic acid in a sample of cells from a subject e.g., detecting PGC-1 mRNA levels or determining whether a genomic PGC-1 gene has been mutated or deleted.

In one embodiment, the nucleic acid molecule of the invention encodes a protein or portion thereof which includes an amino acid sequence which is sufficiently homologous to an amino acid sequence of SEQ ID NO:2, SEQ ID NO:5 such that the protein or portion thereof maintains one or more of the following biological activities: 1) it can interact with (e.g., bind to) PPARγ; 2) it can modulate PPARγ activity; 3) it can modulate UCP expression; 4) it can modulate thermogenesis in adipocytes, e.g., thermogenesis in brown adipocytes, or muscle; 5) it can modulate oxygen consumption in adipocytes or muscle; 6) it can modulate adipogenesis, e.g., differentiation of white adipocytes into brown adipocytes; 7) it can modulate insulin sensitivity of cells, e.g., insulin sensitivity of muscle cells, liver cells, adipocytes; 8) it can interact with (e.g., bind to) nuclear hormone receptors, e.g., the thyroid hormone receptor, the estrogen receptor, the retinoic acid receptor; 9) it can modulate the activity of nuclear hormone receptors; and 10) it can interact with (e.g., bind to) the transcription factor C/EBPα.

As used herein, the language "sufficiently homologous" refers to proteins or portions thereof which have amino acid sequences which include a minimum number of identical or equivalent (e.g., an amino acid residue which has a similar side chain as an amino acid residue in SEQ ID NO:2, SEQ ID NO:5) amino acid residues to an amino acid sequence of SEQ ID NO:2, SEQ ID NO:5 such that the protein or portion thereof maintains one or more of the following biological activities: 1) it can interact with (e.g., bind to) PPARγ; 2) it can modulate PPARγ activity; 3) it can modulate UCP expression; 4) it can modulate thermogenesis in adipocytes, e.g., thermogenesis in brown adipocytes, or muscle; 5) it can modulate oxygen consumption in adipocytes or muscle; 6) it can modulate adipogenesis, e.g., differentiation of white adipocytes into brown adipocytes; 7) it can modulate insulin sensitivity of cells, e.g., insulin sensitivity of muscle cells, liver cells, adipocytes; 8) it can interact with (e.g., bind to) nuclear hormone receptors, e.g., the thyroid hormone receptor, the estrogen receptor, the retinoic acid receptor; 9) it can modulate the activity of nuclear hormone receptors; and 10) it can interact with (e.g., bind to) the transcription factor C/EBPα. In another embodiment, the protein is at least about 50%, preferably at least about 60%, more preferably at least about 70%, yet more preferably at least about 80%, still more preferably at least about 90%, and most preferably at least about 95% or more homologous to the entire amino acid sequence of SEQ ID NO:2, SEQ ID NO:5.

Portions of proteins encoded by the PGC-1 nucleic acid molecule of the invention are preferably biologically active portions of the PGC-1 protein. As used herein, the term "biologically active portion of PGC-1" is intended to include a portion, e.g., a domain/motif, of PGC-1 that has one or more of the following activities: 1) it can interact with (e.g., bind to) PPARγ; 2) it can modulate PPARγ activity; 3) it can modulate UCP expression; 4) it can modulate thermgenesis in adipocytes, e.g., thermogenesis in brown adipocytes, or muscle; 5) it can modulate oxygen consumption in adipocytes or muscle; 6) it can modulate adipogenesis, e.g., differentiation of white adipocytes into brown adipocytes; 7) it can modulate insulin sensitivity of cells, e.g., insulin sensitivity of muscle cells, liver cells, adipocytes; 8) it can interact with (e.g., bind to) nuclear hormone receptors, e.g., the thyroid hormone receptor, the estrogen receptor, the retinoic acid receptor; 9) it can modulate the activity of nuclear hormone receptors; and 10) it can interact with (e.g., bind to) the transcription factor C/EBPα.

Standard binding assays, e.g., immunoprecipitations and yeast two-hybrid assays as described herein, can be performed to determine the ability of a PGC-1 protein or a biologically active portion thereof to interact with (e.g., bind to) PPARγ, C/EBPα, and nuclear hormone receptors. If a PGC-1 family member is found to interact with PPARγ, C/EBPα, and/or nuclear hormone receptors, then they are also likely to be modulators of the activity of PPARγ, C/EBPPα, and nuclear hormone receptors.

To determine whether a PGC-1 family member of the present invention modulates UCP expression, in vitro transcriptional assays can be performed. To perform such an assay, the full length promoter and enhancer of UCP can be linked to a reporter gene such as chloramphenicol acetyl-transferase (CAT) and introduced into host cells. The same host cells can then be transfected with PPARγ/RXRα and nucleic acid encoding the PGC-1 molecule. The effect of the PGC-1 molecule can be measured by testing CAT activity and comparing it to CAT activity in cells which do not contain nucleic acid encoding the PGC-1 molecule. An increase or decrease in CAT activity indicates a modulation of UCP expression and since UCP expression is known to be a critical component in the cascade of events leading to elevated thermogenesis, this assay can also measure the ability of the PGC-1 molecule to modulate thermogenesis in adipocytes.

The above described assay for testing the ability of a PGC-1 molecule to modulate UCP expression can also be used to test the ability of the PGC-1 molecule to modulate adipogenesis, e.g., differentiation of white adipose tissue to brown adipose tissue, as UCP expression is specific to brown adipose tissue. If a PGC-1 molecule can modulate UCP expression is can most likely modulate the differentiation of white adipose tissue to brown adipose tissue. Alternatively, the ability of a PGC-1 molecule to modulate the differentiation of white adipose tissue to brown adipose tissue can be measured by introducing a PGC-1 molecule into a cell, e.g., a white adipocyte, and measuring the number of mitochondria in the cell as compared to the number of mitochondria in a control cell which does not contain the PGC-1 molecule. As brown adipocytes are known to contain substantially greater numbers of mitochondria than white adipocytes, an increase or decrease in the number of mitochondria (or in a mitochondrial marker such as cytochrome c oxidase) in the test cell as compared to the control cell indicates that the PGC-1 molecule can modulate differentiation of white adipose tissue to brown adipose tissue.

The ability of a PGC-1 molecule to modulate insulin sensitivity of a cell can be determined by performing an assay in which cells, e.g., muscle cells, liver cells, or adipocytes, are transformed to express the PGC-1 protein, incubated with radioactively labeled glucose ($^{14}C$ glucose), and treated with insulin. An increase or decrease in glucose in the cells containing PGC-1 as compared to the control cells indicates that the PGC-1 can modulate insulin sensitivity of the cells. Alternatively, the cells containing PGC-1 can be incubated with a radioactively labeled phosphate source (e.g., [$^{32}P$]ATP) and treated with insulin. Phosphorylation of proteins in the insulin pathway, e.g., insulin receptor, can then be measured. An increase or decrease in phosphorylation of a protein in the insulin pathway in cells containing PGC-1 as compared to the control cells indicates that the PGC-1-can modulate insulin sensitivity of the cells.

In one embodiment, the biologically active portion of PGC-1 comprises a domain or motif. Examples of such domains/motifs include a tyrosine phosphorylation site, a cAMP phosphorylation site, a serine-arginine (SR) rich domain, an RNA binding motif, and an LXXLL (SEQ ID NO:3) motif which mediates interaction with a nuclear receptor. In a preferred embodiment, the biologically active portion of the protein which includes the domain or motif can modulate differentiation of white adipocytes to brown adipocytes and/or thermogenesis in brown adipocytes. These domains are described in detail herein. Additional nucleic acid fragments encoding biologically active portions of PGC-1 can be prepared by isolating a portion of SEQ ID NO:1, SEQ ID NO:4 or a homologous nucleotide sequence, expressing the encoded portion of PGC-1 protein or peptide (e.g., by recombinant expression in vitro) and assessing the activity of the encoded portion of PGC-1 protein or peptide.

The invention further encompasses nucleic acid molecules that differ from the nucleotide sequence shown in SEQ ID NO:1, SEQ ID NO:4 (and portions thereof) due to degeneracy of the genetic code and thus encode the same PGC-1 protein as that encoded by the nucleotide sequence shown in SEQ ID NO:1, SEQ ID NO:4. In another embodiment, an isolated nucleic acid molecule of the invention has a nucleotide sequence encoding a protein having an amino acid sequence shown in SEQ ID NO:2, SEQ ID NO:5 or a protein having an amino acid sequence which is at least about 50%, preferably at least about 60%, more preferably at least about 70%, yet more preferably at least about 80%, still more preferably at least about 90%, and most preferably at least about 95% or more homologous to the amino acid sequence of SEQ ID NO:2, SEQ ID NO:5.

In addition to the mouse and human PGC-1 nucleotide sequences shown in SEQ ID NO:1 and SEQ ID NO:4, it will be appreciated by those skilled in the art that DNA sequence polymorphisms that lead to changes in the amino acid sequences of PGC-1 may exist within a population (e.g., a mammalian population, e.g., a human population). Such genetic polymorphism in the PGC-1 gene may exist among individuals within a population due to natural allelic variation. As used herein, the terms "gene" and "recombinant gene" refer to nucleic acid molecules comprising an open reading frame encoding a PGC-1 protein, preferably a mammalian, e.g., human, PGC-1 protein. Such natural allelic variations can typically result in 1–5% variance in the nucleotide sequence of the PGC-1 gene. Any and all such nucleotide variations and resulting amino acid polymorphisms in PGC-1 that are the result of natural allelic variation and that do not alter the functional activity of PGC-1 are intended to be within the scope of the invention. Moreover, nucleic acid molecules encoding PGC-1 proteins from other species, and thus which have a nucleotide sequence which differs from the mouse sequence of SEQ ID NO:1, SEQ ID NO:4, are intended to be within the scope of the invention. Nucleic acid molecules corresponding to natural allelic variants and human homologues of the mouse PGC-1 cDNA of the invention can be isolated based on their homology to the mouse PGC-1 nucleic acid disclosed herein using the mouse cDNA, or a portion thereof, as a hybridization probe according to standard hybridization techniques under stringent hybridization conditions (see Example II).

Moreover, nucleic acid molecules encoding other PGC-1 family members and thus which have a nucleotide sequence which differs from the PGC-1 sequences of SEQ ID NO:1 or SEQ ID NO:4 are intended to be within the scope of the invention. For example, a PGC-2 cDNA can be identified based on the nucleotide sequence of human PGC-1 or mouse PGC-1. Moreover, nucleic acid molecules encoding PGC-1 proteins from different species, and thus which have a nucleotide sequence which differs from the PGC-1 sequences of SEQ ID NO:1 or SEQ ID NO:4 are intended to be within the scope of the invention. For example, rat PGC-1 cDNA can be identified based on the nucleotide sequence of a human PGC-1.

Accordingly, in another embodiment, an isolated nucleic acid molecule of the invention is at least 15 nucleotides in length and hybridizes under stringent conditions to the nucleic acid molecule comprising the nucleotide sequence of SEQ ID NO:1, SEQ ID NO:4 or a nucleotide sequence which is about 60%, preferably at least about 70%, more preferably at least about 80%, still more preferably at least about 90%, and most preferably at least about 95% or more homologous to the nucleotide sequence of SEQ ID NO:1, SEQ ID NO:4. In other embodiments, the nucleic acid is at least 30, 50, 100, 250 or 500 nucleotides in length. As used herein, the term "hybridizes under stringent conditions" is intended to describe conditions for hybridization and washing under which nucleotide sequences at least 60% homologous to each other typically remain hibridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. A preferred, non-limiting example of stringent hybridization conditions are hybridization in 6X sodium chloride/sodium citrate (SSC) at about 45° C., followed by one or more washes in 0.2 X SSC, 0.1% SDS at 50–65° C. Preferably, an isolated nucleic acid molecule of the invention that hybridizes under stringent conditions to the sequence of SEQ ID NO:1, SEQ ID NO:4 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural human PGC-1.

In addition to naturally-occurring allelic variants of the PGC-1 sequence that may exist in the population, the skilled artisan will further appreciate that changes can be introduced by mutation into the nucleotide sequence of SEQ ID NO:1, SEQ ID NO:4, thereby leading to changes in the amino acid sequence of the encoded PGC-1 protein, without altering the functional ability of the PGC-1 protein. For example, nucleotide substitutions leading to amino acid substitutions at "non-essential" amino acid residues can be made in the sequence of SEQ ID NO:1, SEQ ID NO:4. A "non-essential" amino acid residue is a residue that can be altered from the wild-type sequence of PGC-1 (e.g., the sequence of SEQ ID NO:2, SEQ ID NO:5) without altering the activity of PGC-1, whereas an "essential" amino acid residue is required for PGC-1 activity. For example, amino acid residues involved in the interaction of PGC-1 to PPARγ are most likely essential residues of PGC-1. Other amino acid residues, however, (e.g., those that are not conserved or only semi-conserved between mouse and human) may not be essential for activity and thus are likely to be amenable to alteration without altering PGC-1 activity.

Accordingly, another aspect of the invention pertains to nucleic acid molecules encoding PGC-1 proteins that contain changes in amino acid residues that are not essential for PGC-1 activity. Such PGC-1 proteins differ in amino acid sequence from SEQ ID NO:2, SEQ ID NO:5 yet retain at least one of the PGC-1 activities described herein. In one embodiment, the isolated nucleic acid molecule comprises a nucleotide sequence encoding a protein, wherein the protein comprises an amino acid sequence at least about 60% homologous to the amino acid sequence of SEQ ID NO:2, SEQ ID NO:5 and is capable of modulating differentiation of white adipocytes to brown adipocytes and/or thermogenesis of brown adipocytes. Preferably, the protein encoded by the nucleic acid molecule is at least about 70% homologous, preferably at least about 80–85% homologous, still more preferably at least about 90%, and most preferably at least about 95% homologous to the amino acid sequence of SEQ ID NO:2, SEQ ID NO:5.

"Sequence identity or homology", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then die molecules are homologous or sequence identical at that position. The percent of homology or sequence identity between two sequences is a function of the number of matching or homologous identical positions shared by the two sequences divided by the number of positions compared x 100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from, from deletions or insertions in one of the sequences are counted as mismatches.

The comparison of sequences and determination of percent homology between two sequences can be accomplished using a mathematical algorithm. Preferably, the alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11–17 (1989) which has been incorporated into the ALIGN program (version 2.0) (available at http://vega.igh.cnrs.fr/bin/align-guess.cgi), using a PAM120 weight residue table, a gap length penalty of 12 and a gap penalty of 4.

An isolated nucleic acid molecule encoding a PGC-1 protein homologous to the protein of SEQ ID NO:2, SEQ ID NO:5 can be created by introducing one or more nucleotide substitutions, additions or deletions into the nucleotide sequence of SEQ ID NO:1, SEQ ID NO:4 or a homologous nucleotide sequence such that one or more amino acid substitutions, additions or deletions are introduced into the encoded protein. Mutations can be introduced into SEQ ID NO:1, SEQ ID NO:4 or the homologous nucleotide sequence by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in PGC-1 is preferably replaced with another amino acid residue from the same side chain family. Alternatively, in another embodiment, mutations can be introduced randomly along all or part of a PGC-1 coding sequence, such as by saturation mutagenesis, and the resultant mutants can be screened for a PGC-1 activity described herein to identify mutants that retain PGC-1 activity. Following mutagenesis of SEQ ID NO:1, SEQ ID NO:4, the encoded protein can be expressed recombinantly (e.g., as described in Example IV) and the activity of the protein can be determined using, for example, assays described herein.

In addition to the nucleic acid molecules encoding PGC-1 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire PGC-1 coding strand, or to only a portion thereof. In one embodiment, an antisense nucleic acid molecule is antisense to a "coding region" of the coding strand of a nucleotide sequence encoding PGC-1. The term "coding region" refers to the region of the nucleotide sequence comprising codons which are translated into amino acid residues (e.g., the entire coding region of SEQ ID NO:1 comprises nucleotides 92 to 2482, the entire coding region of SEQ ID NO:4 comprises nucleotides 89 to 2482). In another embodiment, the antisense nucleic acid molecule is antisense to a "noncoding region" of the coding strand of a nucleotide sequence encoding PGC-1. The term "noncoding region" refers to 5' and 3' sequences which flank the coding region that are not translated into amino acids (i.e., also referred to as 5' and 3' untranslated regions).

Given the coding strand sequences encoding PGC-1 disclosed herein (e.g., SEQ ID NO:1, SEQ ID NO:4), antisense nucleic acids of the invention can be designed according to the rules of Watson and Crick base pairing. The antisense nucleic acid molecule can be complementary to the entire coding region of PGC-1 mRNA, but more preferably is an oligonucleotide which is antisense to only a portion of the coding or noncoding region of PGC-1 mRNA. For example, the antisense oligonucleotide can be complementary to the region surrounding the translation start site of PGC-1 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a PGC-1 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of an antisense nucleic acid molecule of the invention includes direct injection at a tissue site. Alternatively, an antisense nucleic acid molecule can be modified to target selected cells and then administered systemically. For example, for systemic administration, an antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids. Res. 15:6625–6641). The antisense nucleic acid molecule can also comprise a 2'-o-methylribonucleotide (Inoue et al. (1987) Nucleic Acids Res. 15:6131–6148) or a chimeric RNA-DNA analogue (Inoue et al. (1987) FEBS Lett. 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach (1988) Nature 334:585–591)) can be used to catalytically cleave PGC-1 mRNA transcripts to thereby inhibit translation of PGC-1 mRNA. A ribozyme having specificity for a PGC-1-encoding nucleic acid can be designed based upon the nucleotide sequence of a PGC-1 cDNA disclosed herein (e.g., SEQ ID NO:1, SEQ ID NO:4). For example, a derivative of a Tetrahymena L-19 IVS RNA can be constructed in which the nucleotide sequence of the active site is complementary to the nucleotide sequence to be cleaved in a PGC-1-encoding mRNA. See, e.g., Cech et al. U.S. Pat. No. 4,987,071 and Cech et al. U.S. Pat. No. 5,116,742. Alternatively, PGC-1 mRNA can be used to select a catalytic RNA having a specific ribonuclease activity from a pool of RNA molecules. See, e.g., Bartel, D. and Szostak, J. W. (1993) Science 261:1411–1418.

Alternatively, PGC-1 gene expression can be inhibited by targeting nucleotide sequences complementary to the regulatory region of the PGC-1 (e.g., the PGC-1 promoter and/or enhancers) to form triple helical structures that prevent transcription of the PGC-1 gene in target cells. See generally, Helene, C. (1991) Anticancer Drug Des. 6(6):569–84; Helene, C. et al. (1992) Ann. N. Y Acad Sci. 660:27–36; and Maher, L. J. (1992) Bioassays 14(12):807–15.

II. Recombinant Expression Vectors and Host Cells

Another aspect of the invention pertains to vectors, preferably expression vectors, containing a nucleic acid encoding PGC-1 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Meth-* ods in *Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., PGC-1 proteins, mutant forms of PGC-1, fusion proteins, etc.).

The recombinant expression vectors of the invention can be designed for expression of PGC-1 in prokaryotic or eukaryotic cells. For example, PGC-1 can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:3140), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the PGC-1 is cloned into a pGEX expression vector to create a vector encoding a fusion protein comprising, from the N-terminus to the C-terminus, GST-thrombin cleavage site-PGC-1. The fusion protein can be purified by affinity chromatography using glutathione-agarose resin. Recombinant PGC-1 unfused to GST can be recovered by cleavage of the fusion protein with thrombin.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies en host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

In another embodiment, the PGC-1 expression vector is a yeast expression vector. Examples of vectors for expression in yeast *S. cerivisae* include pYepSecl (Baldari, et al., (1987) *EMBO J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed, Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banedji et al. (1983) *Cell* 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to PGC-1 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, Reviews—Trends in Genetics, Vol. 1(1) 1986.

Another aspect of the invention pertains to host cells into which a recombinant expression vector of the invention has been introduced. The terms "host cell" and "recombinant host cell" are used interchangeably herein, it is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, PGC-1 protein can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (Molecular Cloning: A Laboratory Manual 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding PGC-1 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) PGC-1 protein. Accordingly, the invention further provides methods for producing PGC-1 protein using the host cells of the invention. In one embodiment, the method comprises culturing the host cell of invention (into which a recombinant expression vector encoding PGC-1 has been introduced) in a suitable medium until PGC-1 is produced. In another embodiment, the method further comprises isolating PGC-1 from the medium or the host cell.

The host cells of the invention can also be used to produce nonhuman transgenic animals. The nonhuman transgenic animals can be used in screening assays designed to identify agents or compounds, e.g., drugs, pharmaceuticals, etc., which are capable of ameliorating detrimental symptoms of selected disorders such as weight disorders or disorders associated with insufficient insulin activity. For example, in one embodiment, a host cell of the invention is a fertilized oocyte or an embryonic stem cell into which PGC-1-coding sequences have been introduced. Such host cells can then be used to create non-human transgenic animals in which exogenous PGC-1 sequences have been introduced into their genome or homologous recombinant animals in which endogenous PGC-1 sequences have been altered. Such animals are useful for studying the function and/or activity of PGC-1 and for identifying and/or evaluating modulators of PGC-1 activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous PGC-1 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing PGC-1-encoding nucleic acid into the male pronuclei of a fertilized oocyte, e.g., by microinjection, retroviral infection, and allowing the oocyte to develop in a pseudopregnant female foster animal. The human PGC-1 cDNA sequence can be introduced as a transgene into the genome of a nonhuman animal. Alternatively, a nonhuman homologue of the human PGC-1 gene (SEQ ID NO:4), such as a mouse PGC-1 gene (SEQ ID NO:1), can used as a transgene. Intronic sequences and polyadenylation signals can also be included in the transgene to increase the efficiency of expression of the transgene. A tissue-specific regulatory sequence(s) can be operably linked to the PGC-1 transgene to direct expression of PGC-1 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the PGC-1 transgene in its genome and/or expression of PGC-1 mRNA in tissues or cells of the animals. A transgenic founder animal can then be used to breed additional animals carrying the transgene. Moreover, transgenic animals carrying a transgene encoding PGC-1 can further be bred to other transgenic animals carrying other transgenes.

To create a homologous recombinant animal, a vector is prepared which contains at least a portion of a PGC-1 gene into which a deletion, addition or substitution has been introduced to thereby alter, e.g., functionally disrupt, the PGC-1 gene. The PGC-1 gene can be a human gene (e.g., from a human genomic clone isolated from a human genomic library screened with the cDNA of SEQ ID NO:1), but more preferably, is a nonhuman homologue of a human PGC-1 gene. For example, a mouse PGC-1 gene can be used to construct a homologous recombination vector suitable for altering an endogenous PGC-1 gene in the mouse genome. In a preferred embodiment, the vector is designed such that, upon homologous recombination, the endogenous PGC-1 gene is functionally disrupted (i.e., no longer encodes a functional protein; also referred to as a "knock out" vector). Alternatively, the vector can be designed such that, upon homologous recombination, the endogenous PGC-1 gene is mutated or otherwise altered but still encodes functional protein (e.g., the upstream regulatory region can be altered to thereby alter the expression of the endogenous PGC-1 protein). In the homologous recombination vector, the altered portion of the PGC-1 gene is flanked at its 5' and 3' ends by additional nucleic acid of the PGC-1 gene to allow for homologous recombination to occur between the exogenous PGC-1 gene carried by the vector and an endogenous PGC-1 gene in an embryonic stem cell. The additional flanking PGC-1 nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced PGC-1 gene has homologously recombined with the endogenous PGC-1 gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Bems et al.

In another embodiment, transgenic nonhuman animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal from which the cell, e.g., the somatic cell, is isolated.

III. Isolated PGC-1 Proteins and Anti-PGC-1 Antibodies

Another aspect of the invention pertains to isolated PGC-1 proteins, and biologically active portions thereof, as well as peptide fragments suitable for use as immunogens to raise anti-PGC-1 antibodies. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of PGC-1 protein in which the protein is separated from cellular components of the cells in which it is naturally or recombinantly produced. In one embodiment, the language "substantially free of cellular material" includes preparations of PGC-1 protein having less than about 30% (by dry weight) of non-PGC-1 protein (also referred to herein as a "contaminating protein"), more preferably less than about 20% of non-PGC-1 protein, still more preferably less than about 10% of non-PGC-1 protein, and most preferably less than about 5% non-PGC-1 protein. When the PGC-1 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of PGC-1 protein in which the protein is separated from chemical precursors or other chemicals which are involved in the synthesis of the protein. In one embodiment, the language "substantially free of chemical precursors or other chemicals" includes preparations of PGC-1 protein having less than about 30% (by dry weight) of chemical precursors or non-PGC-1 chemicals, more preferably less than about 20% chemical precursors or non-PGC-1 chemicals, still more preferably less than about 10% chemical precursors or non-PGC-1 chemicals, and most preferably less than about 5% chemical precursors or non-PGC-1 chemicals. In preferred embodiments, isolated proteins or biologically active portions thereof lack contaminating proteins from the same animal from which the PGC-1 protein is derived. Typically, such proteins are produced by recombinant expression of, for example, a human PGC-1 protein in a nonhuman cell.

An isolated PGC-1 protein or a portion thereof of the invention has one or more of the following biological activities: 1) it can interact with (e.g., bind to) PPARγ; 2) it can modulate PPARγ activity; 3) it can modulate UCP expression; 4) it can modulate thermogenesis in adipocytes, e.g., thermogenesis in brown adipocytes, or muscle; 5) it can modulate oxygen consumption in adipocytes or muscle; 6) it can modulate adipogenesis, e.g., differentiation of white adipocytes into brown adipocytes; 7) it can modulate insulin sensitivity of cells, e.g., insulin sensitivity of muscle cells, liver cells, adipocytes; 8) it can interact with (e.g., bind to) nuclear hormone receptors, e.g., the thyroid hormone receptor, the estrogen receptor, the retinoic acid receptor; 9) it can modulate the activity of nuclear hormone receptors; and 10) it can interact with (e.g., bind to) the transcription factor C/EBPα. In a preferred embodiment, the PGC-1 protein can modulate differentiation of white adipocytes to brown adipocytes and/or thermogenesis in brown adipocytes or muscle cells.

In preferred embodiments, the protein or portion thereof comprises an amino acid sequence which is sufficiently homologous to an amino acid sequence of SEQ ID NO:2, SEQ ID NO:5 such that the protein or portion thereof maintains the ability to modulate differentiation of adipocytes and/or thermogenesis in brown adipocytes. The portion of the protein is preferably a biologically active portion as described herein. In another preferred embodiment, the PGC-1 protein (i.e., amino acid residues 1–797 and amino acid residues1–798) has an amino acid sequence shown in SEQ ID NO:2, SEQ ID NO:5, respectively, or an amino acid sequence which is at least about 50%, preferably at least about 60%, more preferably at least about 70%, yet more preferably at least about 80%, still more preferably at least about 90%, and most preferably at least about 95% or more homologous to the amino acid sequence shown in SEQ ID NO:2, SEQ ID NO:5. In yet another preferred embodiment, the PGC-1 protein has an amino acid sequence which is encoded by a nucleotide sequence which hybridizes, e.g., hybridizes under stringent conditions, to the nucleotide sequence of SEQ ID NO:1, SEQ ID NO:4 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO: I, SEQ ID NO:4. The preferred PGC-1 proteins of the present invention also preferably possess at least one of the PGC-1 biological activities described herein. For example, a preferred PGC-1 protein of the present invention includes an amino acid sequence encoded by a nucleotide sequence which hybridizes, e.g., hybridizes under stringent conditions, to the nucleotide sequence of SEQ ID NO:1, SEQ ID NO:4 and which can modulate differentiation of white adipocytes to brown adipocytes and/or thermogenesis of brown adipocytes.

In other embodiments, the PGC-1 protein is substantially homologous to the amino acid sequence of SEQ ID NO:2, SEQ ID NO:5 and retains the functional activity of the protein of SEQ ID NO:2, SEQ ID NO:5 yet differs in amino acid sequence due to natural allelic variation or mutagenesis, as described in detail in subsection I above. Accordingly, in another embodiment, the PGC-1 protein is a protein which comprises an amino acid sequence which is at least about 50%, preferably at least about 60%, more preferably at least about 70%, yet more preferably at least about 80%, still more preferably at least about 90%, and most preferably at least about 95% or more homologous to the amino acid sequence of SEQ ID NO:2, SEQ ID NO:5.

Biologically active portions of the PGC-1 protein include peptides comprising amino acid sequences derived from the amino acid sequence of the PGC-1 protein, e.g., the amino acid sequence shown in SEQ ID NO:2, SEQ ID NO:5 or the amino acid sequence of a protein homologous to the PGC-1 protein, which include less amino acids than the full length PGC-1 protein or the full length protein which is homologous to the PGC-1 protein, and exhibit at least one activity of the PGC-1 protein. Typically, biologically active portions (peptides, e.g., peptides which are, for example, 5, 10, 15, 20, 30, 35, 36, 37, 38, 39, 40, 50, 100 or more amino acids in length) comprise a domain or motif, e.g., a tyrosine phosphorylation site, a cAMP phosphorylation site, a serine-arginine (SR) rich domain, and/or an RNA binding motif, with at least one activity of the PGC-1 protein. In a preferred embodiment, the biologically active portion of the protein which includes one or more the domains/motifs described herein can modulate differentiation of adipocytes and/or thermogenesis in brown adipocytes. Moreover, other biologically active portions, in which other regions of the protein are deleted, can be prepared by recombinant techniques and evaluated for one or more of the activities described herein. Preferably, the biologically active portions of the PGC-1 protein include one or more selected domains/ motifs or portions thereof having biological activity.

PGC-1 proteins are preferably produced by recombinant DNA techniques. For example, a nucleic acid molecule encoding the protein is cloned into an expression vector (as described above), the expression vector is introduced into a host cell (as described above) and the PGC-1 protein is expressed in the host cell. The PGC-1 protein can then be isolated from the cells by an appropriate purification scheme using standard protein purification techniques. Alternative to recombinant expression, a PGC-1 protein, polypeptide, or peptide can be synthesized chemically using standard peptide synthesis techniques. Moreover, native PGC-1 protein can be isolated from cells (e.g., brown adipocytes), for example using an anti-PGC-1 antibody (described further below).

The invention also provides PGC-1 chimeric or fusion proteins. As used herein, a PGC-1 "chimeric protein" or "fusion protein" comprises a PGC-1 polypeptide operatively linked to a non-PGC-1 polypeptide. A "PGC-1polypeptide" refers to a polypeptide having an amino acid sequence corresponding to PGC-1, whereas a "non-PGC-1 polypeptide" refers to a polypeptide having an amino acid sequence corresponding to a protein which is not substantially homologous to the PGC-1 protein, e.g., a protein which is different from the PGC-1 protein and which is derived from the same or a different organism. Within the fusion protein, the term "operatively linked" is intended to indicate that the PGC-1 polypeptide and the non-PGC-1 polypeptide are fused in-frame to each other. The non-PGC-1 polypeptide can be fused to the N-terminus or C-terminus of the PGC-1 polypeptide. For example, in one embodiment the fusion protein is a GST-PGC-1 fusion protein in which the PGC-1 sequences are fused to the C-terminus of the GST sequences (see Example IV). Such fusion proteins can facilitate the purification of recombinant PGC-1. In another embodiment, the fusion protein is a PGC-1 protein containing a heterologous signal sequence at its N-terminus. In certain host cells (e.g., mammalian host cells), expression and/or secretion of PGC-1 can be increased through use of a heterologous signal sequence.

Preferably, a PGC-1 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology,* eds. Ausubel et al. John Wiley & Sons: 1992). Moreover, many expression vectors are commercially available that already encode a fusion moiety (e.g., a GST polypeptide). A PGC-1-encoding nucleic acid can be cloned into such an expression vector such that the fusion moiety is linked in-frame to the PGC-1 protein.

The present invention also pertains to homologues of the PGC-1 proteins which function as either a PGC-1 agonist (mimetic) or a PGC-1 antagonist. In a preferred embodiment, the PGC-1 agonists and antagonists stimulate or inhibit, respectively, a subset of the biological activities of the naturally occurring form of the PGC-1 protein. Thus, specific biological effects can be elicited by treatment with a homologue of limited function. In one embodiment, treatment of a subject with a homologue having a subset of the biological activities of the naturally occurring form of the protein has fewer side effects in a subject relative to treatment with the naturally occurring form of the PGC-1 protein.

Homologues of the PGC-1 protein can be generated by mutagenesis, e.g., discrete point mutation or truncation of the PGC-1 protein. As used herein, the term "homologue" refers to a variant form of the PGC-1 protein which acts as an agonist or antagonist of the activity of the PGC-1 protein. An agonist of the PGC-1 protein can retain substantially the same, or a subset, of the biological activities of the PGC-1 protein. An antagonist of the PGC-1 protein can inhibit one or more of the activities of the naturally occurring form of the PGC-1 protein, by, for example, competitively binding to a downstream or upstream member of the PGC-1 cascade which includes the PGC-1 protein. Thus, the mammalian PGC-1 protein and homologues thereof of the present invention can be, for example, either positive or negative regulators of adipocyte differentiation and/or thermogenesis in brown adipocytes.

In an alternative embodiment, homologues of the PGC-1 protein can be identified by screening combinatorial libraries of mutants, e.g., truncation mutants, of the PGC-1 protein for PGC-1 protein agonist or antagonist activity. In one embodiment, a variegated library of PGC-1 variants is generated by combinatorial mutagenesis at the nucleic acid level and is encoded by a variegated gene library. A variegated library of PGC-1 variants can be produced by, for example, enzymatically ligating a mixture of synthetic oligonucleotides into gene sequences such that a degenerate set of potential PGC-1 sequences is expressible as individual polypeptides, or alternatively, as a set of larger fusion proteins (e.g., for phage display) containing the set of PGC-1 sequences therein. There are a variety of methods which can be used to produce libraries of potential PGC-1 homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential PGC-1 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res* 1 1:477.

In addition, libraries of fragments of the PGC-1 protein coding can be used to generate a variegated population of PGC-1 fragments for screening and subsequent selection of homologues of a PGC-1 protein. In one embodiment, a library of coding sequence fragments can be generated by treating a double stranded PCR fragment of a PGC-1 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the PGC-1 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PGC-1 homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify PGC-1 homologues (Arkin and Youvan (1992) *Proc. Natl. Acad. Sci. USA* 89:7811–7815; Delagrave et al. (1993) *Protein Eng.* 6(3):327–331).

An isolated PGC-1 protein, or a portion or fragment thereof, can be used as an immunogen to generate antibodies that bind PGC-1 using standard techniques for polyclonal and monoclonal antibody preparation. The full-length PGC-1 protein can be used or, alternatively, the invention provides antigenic peptide fragments of PGC-1 for use as immunogens. The antigenic peptide of PGC-1 comprises at least 8 amino acid residues of the amino acid sequence shown in SEQ ID NO:2, SEQ ID NO:5 or a homologous amino acid sequence as described herein and encompasses an epitope of PGC-1 such that an antibody raised against the peptide forms a specific immune complex with PGC-1. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of PGC-1 that are located on the surface of the protein, e.g., hydrophilic regions.

A PGC-1 immunogen typically is used to prepare antibodies by immunizing a suitable subject, (e.g., rabbit, goat, mouse or other mammal) with the immunogen. An appropriate immunogenic preparation can contain, for example, recombinantly expressed PGC-1 protein or a chemically synthesized PGC-1 peptide. The preparation can further include an adjuvant, such as Freund's complete or incomplete adjuvant, or similar immunostimulatory agent. Immunization of a suitable subject with an immunogenic PGC-1 preparation induces a polyclonal anti-PGC-1 antibody response.

Accordingly, another aspect of the invention pertains to anti-PGC-1 antibodies. The term "antibody" as used herein refers to immunoglobulin molecules and immunologically active portions of immunoglobulin molecules, i.e., molecules that contain an antigen binding site which specifically binds (immunoreacts with) an antigen, such as PGC-1. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind PGC-1. The term "monoclonal antibody" or "monoclonal antibody composition", as used herein, refers to a population of antibody molecules that contain only one species of an antigen binding site capable of immunoreacting with a particular epitope of PGC-1. A monoclonal antibody composition thus typically displays a single binding affinity for a particular PGC-1 protein with which it immunoreacts.

Polyclonal anti-PGC-1 antibodies can be prepared as described above by immunizing a suitable subject with a PGC-1 immunogen. The anti-PGC-1 antibody titer in the immunized subject can be monitored over time by standard techniques, such as with an enzyme linked immunosorbent assay (ELISA) using immobilized PGC-1. If desired, the antibody molecules directed against PGC-1 can be isolated from the mammal (e.g., from the blood) and further purified by well known techniques, such as protein A chromatography to obtain the IgG fraction. At an appropriate time after immunization, e.g., when the anti-PGC-1 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem* 255:4980–83; Yeh et al. (1976) *PNAS* 76:2927–31; and Yeh et al. (1982) *Int. J Cancer* 29:269–75), the more recent human B cell hybridoma technique (Kozbor et al. (1983) *Immunol Today* 4:72), the EBV-hybridoma technique (Cole et al. (1985), Monoclonal Antibodies and Cancer Therapy, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses,* Plenum Publishing Corp., New York, N.Y. (1980); E. A. Lerner (1981) *Yale J. Biol. Med,* 54:387402; M. L. Gefter et al. (1977) *Somatic Cell Genet.* 3:231–36). Briefly, an immortal cell line (typically a myeloma) is fused to lymphocytes (typically splenocytes) from a mammal immunized with a PGC-1 immunogen as described above, and the culture supernatants of the resulting hybridoma cells are screened to identify a hybridoma producing a monoclonal antibody that binds PGC-1.

Any of the many well known protocols used for fusing lymphocytes and immortalized cell lines can be applied for the purpose of generating an anti-PGC-I monoclonal antibody (see, e.g., G. Galfre et al. (1977) *Nature* 266:55052; Gefter et al. *Somatic Cell Genet.,* cited supra; Lerner, *Yale J. Biol. Med.,* cited supra; Kenneth, *Monoclonal Antibodies,* cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4–1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind PGC-1, e.g., using a standard ELISA assay.

Alternative to preparing monoclonal antibody-secreting hybridomas, a monoclonal anti-PGC-1 antibody can be identified and isolated by screening a recombinant combinatorial immunoglobulin library (e.g., an antibody phage display library) with PGC-1 to thereby isolate immunoglobulin library members that bind PGC-1. Kits for generating and screening phage display libraries are commercially available (e.g., the Pharmacia *Recombinant Phage Antibody System, Catalog No.* 27–9400–01; and the Stratagene Sur-JZAP™ Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1369–1372; Hay-et al. (1992) *Hum. Antibod. Hybridomas* 3:81–85; Huse et al. (1989) *Science* 246:1275–1281; Griffiths et al. (1993) *EMBO J J.* 12:725–734; Hawkins et al. (1992) *J. Mol. Biol.* 226:889–896; Clackson et al. (1991) *Nature* 352:624–628; Gram et al. (1992) *Proc. Natl. Acad. Sci. USA* 89:3576–3580; Garrard et al. (1991) *Bio/Technology* 9:1373–1377; Hoogenboom et al. (1991) *Nucleic Acids Res.* 19:4133–4137; Barbas et al. (1991) *Proc. Natl. Acad. Sci. USA* 88:7978–7982; and McCafferty et al. *Nature* (1990)

Additionally, recombinant anti-PGC-1 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA*

84:214–218; Nishimura et al. (1987) *Cancer Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225, 539; Jones et al. (1986) *Nature* 321:552–525; Verhoeyen et al. (1988) *Science* 239:1534; and Beidler et al. (1988) *J. Immunol.* 141:4053–4060.

An anti-PGC-1 antibody (e.g., monoclonal antibody) can be used to isolate PGC-1 by standard techniques, such as affinity chromatography or immunoprecipitation. An anti-PGC-1 antibody can facilitate the purification of natural PGC-1 from cells and of recombinantly produced PGC-1 expressed in host cells. Moreover, an anti-PGC-1 antibody can be used to detect PGC-1 protein (e.g., in a cellular lysate or cell supernatant) in order to evaluate the abundance and pattern of expression of the PGC-1 protein. Anti-PGC-1 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

IV. Pharmaceutical Compositions

The PGC-1 nucleic acid molecules, PGC-1 proteins, PGC-1 modulators, and anti-PGC-1 antibodies (also referred to herein as "active compounds") of the invention can be incorporated into pharmaceutical compositions suitable for administration to a subject, e.g., a human. Such compositions typically comprise the nucleic acid molecule, protein, modulator, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediamirietetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a. PGC-1 protein or anti-PGC-1 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, polypeptides, polypeptide homologues, modulators, and antibodies described herein can be used in one or more of the following methods: 1) drug screening assays; 2) diagnostic assays; and 3) methods of treatment. A PGC-1 protein of the invention has one or more of the activities described herein and can thus be used to, for example, modulate adipocyte differentiation, thermogenesis in brown adipocytes, and insulin sensitivity in various cells, e.g., muscle cells, liver cells, and adipocytes. The isolated nucleic acid molecules of the invention can be used to express PGC-1 protein (e.g., via a recombinant expression vector in a host cell in gene therapy applications), to detect PGC-1 mRNA (e.g., in a biological sample) or a genetic lesion in a PGC-1 gene, and to modulate PGC-1 activity, as described further below. In addition, the PGC-1 proteins can be used to screen drugs or compounds which modulate PGC-1 protein activity as well as to treat disorders characterized by insufficient production of PGC-1 protein or production of PGC-1 protein forms which have decreased activity compared to wild type PGC-1. Moreover, the anti-PGC-1 antibodies of the invention can be used to detect and isolate PGC-1 protein and modulate PGC-1 protein activity.

a. Drug Screening Assays:

The invention provides methods for identifying compounds or agents which can be used to treat disorders characterized by (or associated with) aberrant or abnormal PGC-1 nucleic acid expression and/or PGC-1 polypeptide activity. These methods are also referred to herein as drug screening assays and typically include the step of screening a candidate/test compound or agent for the ability to interact with (e.g., bind to) a PGC-1 protein, to modulate the interaction of a PGC-1 protein and a target molecule, and/or to modulate PGC-1 nucleic acid expression and/or PGC-1 protein activity. Candidate/test compounds or agents which have one or more of these abilities can be used as drugs to treat disorders characterized by aberrant or abnormal PGC-1 nucleic acid expression and/or PGC-1 protein activity. Candidate/test compounds include, for example, 1) peptides such as soluble peptides, including Ig-tailed fusion peptides and members of random peptide libraries (see, e.g., Lam, K. S. et al. (1991) *Nature* 354:82–84; Houghten, R. et al. (1991) *Nature* 354:84–86) and combinatorial chemistry-derived molecular libraries made of D-and/or L-configuration amino acids; 2) phosphopeptides (e.g., members of random and partially degenerate, directed phosphopeptide libraries, see, e.g., Songyang, Z. et al. (1993) *Cell* 72:767–778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

In one embodiment, the invention provides assays for screening candidate/test compounds which interact with (e.g., bind to) PGC-1 protein. Typically, the assays are cell-free assays which include the steps of combining a PGC-1 protein or a biologically active portion thereof, and a candidate/test compound, e.g., under conditions which allow for interaction of (e.g., binding of) the candidate/test compound to the PGC-1 protein or portion thereof to form a complex, and detecting the formation of a complex, in which the ability of the candidate compound to interact with (e.g., bind to) the PGC-1 polypeptide or fragment thereof is indicated by the presence of the candidate compound in the complex. Formation of complexes between the PGC-1 protein and the candidate compound can be quantitated, for example, using standard immunoassays.

In another embodiment, the invention provides screening assays to identify candidate/test compounds which modulate (e.g., stimulate or inhibit) the interaction (and most likely PGC-1 activity as well) between a PGC-1 protein and a molecule (target molecule) with which the PGC-1 protein normally interacts. Examples of such target molecules include proteins in the same signaling path as the PGC-1 protein, e.g., proteins which may function upstream (including both stimulators and inhibitors of activity) or downstream of the PGC-1 protein in a pathway involving regulation of body weight, e.g., PPARγ, C/EBPα, nuclear hormone receptors such as the thyroid hormone receptor, the estrogen receptor, and the retinoic acid receptor, or in a pathway involving insulin sensitivity, e.g., PPARγ. Typically, the assays are cell-free assays which include the steps of combining a PGC-1 protein or a biologically active portion thereof, a PGC-1 target molecule and a candidate/test compound, e.g., under conditions wherein but for the presence of the candidate compound, the PGC-1 protein or biologically active portion thereof interacts with (e.g., binds to) the target molecule, and detecting the formation of a complex which includes the PGC-1 protein and the target molecule or detecting the interaction/reaction of the PGC-1 protein and the target molecule. Detection of complex formation can include direct quantitation of the complex by, for example, measuring inductive effects of the PGC-1 protein. A statistically significant change, such as a decrease, in the interaction of the PGC-1 and target molecule (e.g., in the formation of a complex between the PGC-1 and the target molecule) in the presence of a candidate compound (relative to what is detected in the absence of the candidate compound) is indicative of a modulation (e.g., stimulation or inhibition) of the interaction between the PGC-1 protein and the target molecule. Modulation of the formation of complexes between the PGC-1 protein and the target molecule can be quantitated using, for example, an immunoassay.

To perform the above drug screening assays, it is desirable to immobilize either PGC-1 or its target molecule to facilitate separation of complexes from uncomplexed forms of one or both of the proteins, as well as to accommodate automation of the assay. Interaction (e.g., binding of) of PGC-1 to a target molecule, in the presence and absence of a candidate compound, can be accomplished in any vessel suitable for containing the reactants. Examples of such vessels include microtitre plates, test tubes, and microcentrifuge tubes. In one embodiment, a fusion polypeptide can be provided which adds a domain that allows the polypeptide to be bound to a matrix. For example, glutathione-S-transferase/PGC-1 fusion polypeptides can be adsorbed onto glutathione sepharose beads (Sigma Chemical, St. Louis, Mo.) or glutathione derivatized microtitre plates, which are then combined with the cell lysates (e.g. $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of PGC-1-binding polypeptide found in the bead fraction quantitated from the gel using standard electrophoretic techniques.

Other techniques for immobilizing polypeptides on matrices can also be used in the drug screening assays of the invention. For example, either PGC-1 or its target molecule can be immobilized utilizing conjugation of biotin and streptavidin. Biotinylated PGC-1 molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with PGC-1 but which do not interfere with binding of the polypeptide to its target molecule can be derivatized to the wells of the plate, and PGC-1 trapped in the wells by antibody conjugation. As described above, preparations of a PGC-1-binding polypeptide and a candidate compound are incubated in the PGC-1-presenting wells of the plate, and the amount of complex trapped in the well can be quantitated. Methods for detecting such complexes, in addition to those described above for the GST-immobilized complexes, include immunodetection of complexes using antibodies reactive with the PGC-1 target molecule, or which are reactive with PGC-1 polypeptide and compete with the target molecule; as well as enzyme-linked assays which rely on detecting an enzymatic activity associated with the target molecule.

In yet another embodiment, the invention provides a method for identifying a compound (e.g., a screening assay) capable of use in the treatment of a disorder characterized by (or associated with) aberrant or abnormal PGC-1 nucleic acid expression or PGC-1 polypeptide activity. This method typically includes the step of assaying the ability of the compound or agent to modulate the expression of the PGC-1 nucleic acid or the activity of the PGC-1 protein thereby identifying a compound for treating a disorder characterized by aberrant or abnormal PGC-1 nucleic acid expression or PGC-1 polypeptide activity. Disorders characterized by aberrant or abnormal PGC-1 nucleic acid expression or PGC-1 protein activity are described herein. Methods for assaying the ability of the compound or agent to modulate the expression of the PGC-1 nucleic acid or activity of the PGC-1 protein are typically cell-based assays. For example, cells which are sensitive to ligands which transduce signals via a pathway involving PGC-1 can be induced to overexpress a PGC-1 protein in the presence and absence of a candidate compound. Candidate compounds which produce a statistically significant change in PGC-1-dependent responses (either stimulation or inhibition) can be identified. In one embodiment, expression of the PGC-1 nucleic acid or activity of a PGC-1 protein is modulated in cells and the effects of candidate compounds on the readout of interest (such as rate of cell proliferation or differentiation) are measured. For example, the expression of genes which are up- or down-regulated in response to a PGC-1 protein-dependent signal cascade can be assayed. In preferred embodiments, the regulatory regions of such genes, e.g., the 5' flanking promoter and enhancer regions, are operably linked to a detectable marker (such as luciferase) which encodes a gene product that can be readily detected. Phosphorylation of PGC-1 or PGC-1 target molecules can also be measured, for example, by immunoblotting.

Alternatively, modulators of PGC-1 nucleic acid expression (e.g., compounds which can be used to treat a disorder characterized by aberrant or abnormal PGC-1 nucleic acid expression or PGC-1 protein activity) can be identified in a method wherein a cell is contacted with a candidate compound and the expression of PGC-1 mRNA or protein in the cell is determined. The level of expression of PGC-1 mRNA or protein in the presence of the candidate compound is compared to the level of expression of PGC-1 mRNA or protein in the absence of the candidate compound. The candidate compound can then be identified as a modulator of PGC-1 nucleic acid expression based on this comparison and be used to treat a disorder characterized by aberrant PGC-1 nucleic acid expression. For example, when expression of PGC-1 mRNA or polypeptide is greater (statistically significantly greater) in the presence of the candidate compound than in its absence, the candidate compound is identified as a stimulator of PGC-1 nucleic acid expression. Alternatively, when PGC-1 nucleic acid expression is less (statistically significantly less) in the presence of the candidate compound than in its absence, the candidate compound is identified as an inhibitor of PGC-1 nucleic acid expression. The level of PGC-1 nucleic acid expression in the cells can be determined by methods described herein for detecting PGC-1 mRNA or protein.

In yet another aspect of the invention, the PGC-1 proteins can be used as "bait proteins" in a two-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO 94/10300), to identify other proteins, which bind to or interact with PGC-1 ("PGC-1-binding proteins" or "PGC-1-bp") and modulate PGC-1 protein activity. Such PGC-1-binding proteins are also likely to be involved in the propagation of signals by the PGC-1 proteins as, for example, upstream or downstream elements of the PGC-1 pathway.

The two-hybrid system is based on the modular nature of most transcription factors, which consist of separable DNA-binding and activation domains. Bartel, P. et al. "Using the Two-Hybrid System to Detect Protein-Protein Interactions" in Cellular Interactions in Development: A Practical Approach, Hartley, D. A. ed. (Oxford University Press, Oxford, 1993) pp. 153–179. Briefly, the assay utilizes two different DNA constructs. In one construct, the gene that codes for PGC-1 is fused to a gene encoding the DNA binding domain of a known transcription factor (e.g., GAL-4). In the other construct, a DNA sequence, from a library of DNA sequences, that encodes an unidentified polypeptide ("prey" or "sample") is fused to a gene that codes for the activation domain of the known transcription factor. If the "bait" and the "prey" proteins are able to interact, in vivo, forming a PGC-1-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the polypeptide which interacts with PGC-1.

Modulators of PGC-1 protein activity and/or PGC-1 nucleic acid expression identified according to these drug screening assays can be used to treat, for example, weight disorders, e.g. obesity, and disorders associated with insufficient insulin activity, e.g., diabetes. These methods of treatment include the steps of administering the modulators of PGC-1 protein activity and/or nucleic acid expression, e.g., in a pharmaceutical composition as described in subsection IV above, to a subject in need of such treatment, e.g., a subject with a disorder described herein.

b. Diagnostic Assays:

The invention further provides a method for detecting the presence of PGC-1 in a biological sample. The method involves contacting the biological sample with a compound or an agent capable of detecting PGC-1 polypeptide or mRNA such that the presence of PGC-1 is detected in the biological sample. A preferred agent for detecting PGC-1 mRNA is a labeled or labelable nucleic acid probe capable of hybridizing to PGC-1 mRNA. The nucleic acid probe can be, for example, the full-length PGC-1 cDNA of SEQ ID NO:1, or a portion thereof, such as an oligonucleotide of at least 15, 30, 50, 100, 250 or 500 nucleotides in length and sufficient to specifically hybridize under stringent conditions to PGC-1 mRNA. A preferred agent for detecting PGC-1 protein is a labeled or labelable antibody capable of binding to PGC-1 protein. Antibodies can be polyclonal, or more preferably, monoclonal. An intact antibody, or a fragment thereof (e.g., Fab or F(ab')$_2$) can be used. The term "labeled or labelable", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect PGC-1 mRNA or protein in a biological sample in vitro as well as in vivo. For example, in vitro techniques for detection of PGC-1 mRNA include Northern hybridizations and in situ hybridizations. In vitro techniques for detection of PGC-1 protein include enzyme linked immunosorbent assays (ELISAs), Western blots, immunoprecipitations and immunofluorescence. Alternatively, PGC-1 protein can be detected in vivo in a subject by introducing into the subject a labeled anti-PGC-1 antibody. For example, the antibody can be labeled with a radioactive marker whose presence and location in a subject can be detected by standard imaging techniques.

The invention also encompasses kits for detecting the presence of PGC-1 in a biological sample. For example, the kit can comprise a labeled or labelable compound or agent capable of detecting PGC-1 protein or mRNA in a biological sample; means for determining the amount of PGC-1 in the sample; and means for comparing the amount of PGC-1 in the sample with a standard. The compound or agent can be packaged in a suitable container. The kit can further comprise instructions for using the kit to detect PGC-1 mRNA or protein.

The methods of the invention can also be used to detect genetic lesions in a PGC-1 gene, thereby determining if a subject with the lesioned gene is at risk for a disorder characterized by aberrant or abnormal PGC-1 nucleic acid expression or PGC-1 protein activity as defined herein. In preferred embodiments, the methods include detecting, in a sample of cells from the subject, the presence or absence of a genetic lesion characterized by at least one of an alteration affecting the integrity of a gene encoding a PGC-1 protein, or the misexpression of the PGC-1 gene. For example, such genetic lesions can be detected by ascertaining the existence of at least one of 1) a deletion of one or more nucleotides from a PGC-1 gene; 2) an addition of one or more nucleotides to a PGC-1 gene; 3) a substitution of one or more nucleotides of a PGC-1 gene, 4) a chromosomal rearrangement of a PGC-1 gene; 5) an alteration in the level of a messenger RNA transcript of a PGC-1 gene, 6) aberrant modification of a PGC-1 gene, such as of the methylation pattern of the genomic DNA, 7) the presence of a non-wild type splicing pattern of a messenger RNA transcript of a PGC-1 gene, 8) a non-wild type level of a PGC-1-protein, 9) allelic loss of a PGC-1 gene, and 10) inappropriate post-translational modification of a PGC-1-protein. As described herein, there are a large number of assay techniques known in the art which can be used for detecting lesions in a PGC-1 gene.

In certain embodiments, detection of the lesion involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1994) PNAS 91:360–364), the latter of which can be particularly useful for detecting point mutations in the PGC-1-gene (see Abravaya et al. (1995) Nucleic Acids Res. 23:675–682). This method can include the steps of collecting a sample or cells from a patient, isolating nucleic acid (e.g., genomic, mRNA or both) from the cells of the sample, contacting the nucleic acid sample with one or more primers which specifically hybridize to a PGC-1 gene under conditions such that hybridization and amplification of the PGC-1-gene (if present) occurs, and detecting the presence or absence of an amplification product, or detecting the size of the amplification product and comparing the length to a control sample.

In an alternative embodiment, mutations in a PGC-1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the PGC-1 gene and detect mutations by comparing the sequence of the sample PGC-1 with the corresponding wild-type (control) sequence. Examples of sequencing reactions include those based on techniques developed by Maxim and Gilbert ((1977) PNAS 74:560) or Sanger ((1977) PNAS 74:5463). A variety of automated sequencing procedures can be utilized when performing the diagnostic assays ((1995) Biotechniques 19:448), including sequencing by mass spectrometry (see, e.g., PCT International Publication No. WO 94/16101; Cohen et al. (1996) Adv. Chromatogr. 36:127–162; and Griffin et al. (1993) Appl. Biochem. Biotechnol. 38:147–159).

Other methods for detecting mutations in the PGC-1 gene include methods in which protection from cleavage agents is used to detect mismatched bases in RNA/RNA or RNA/DNA duplexes (Myers et al. (1985) Science 230:1242); Cotton et al. (1988) PNAS 85:4397; Saleeba et al. (1992) Meth. Enzymol. 217:286–295), electrophoretic mobility of mutant and wild type nucleic acid is compared (Orita et al. (1989) PNAS 86:2766; Cotton (1993) Mutat Res 285:125–144; and Hayashi (1992) Genet Anal Tech Appl 9:73–79), and movement of mutant or wild-type fragments in polyacrylamide gels containing a gradient of denaturant is assayed using denaturing gradient gel electrophoresis (Myers et al (1985) Nature 313:495). Examples of other techniques for detecting point mutations include, selective oligonucleotide hybridization, selective amplification, and selective primer extension.

c. Methods of Treatment

Another aspect of the invention pertains to methods for treating a subject, e.g., a human, having a disease or disorder characterized by (or associated with) aberrant or abnormal PGC-1 nucleic acid expression and/or PGC-1 protein activity. These methods include the step of administering a PGC-1 modulator to the subject such that treatment occurs. The language "aberrant or abnormal PGC-1 expression" refers to expression of a non-wild-type PGC-1 protein or a non-wild-type level of expression of a PGC-1 protein. Aberrant or abnormal PGC-1 protein activity refers to a non-wild-type PGC-1 protein activity or a non-wild-type level of PGC-1 protein activity. As the PGC-1 protein is involved in, for example, a pathway involving adipocyte differentiation, thermogenesis in brown adipocytes, and insulin sensitivity, aberrant or abnormal PGC-1 protein activity or nucleic acid expression interferes with the normal weight control and metabolic functions. Non-limiting examples of disorders or diseases characterized by or associated with abnormal or aberrant PGC-1 protein activity or nucleic acid expression include weight disorders, e.g., obesity, cachexia, anorexia, and disorders associated with insufficient insulin activity, e.g., diabetes. Disorders associated with body weight are disorders associated with abnormal body weight or abnormal control of body weight. As used herein, the language "diseases associated with or characterized by insufficient insulin activity" include disorders or diseases in which there is an abnormal utilization of glucose due to abnormal insulin function. Abnormal insulin function includes any abnormality or impairment in insulin production, e.g., expression and/or transport through cellular organelles, such as insulin deficiency resulting from, for example, loss of β cells as in IDDM (Type I diabetes), secretion, such as impairment of insulin secretory responses as in NIDDM (Type 11 diabetes), the form of the insulin molecule itself, e.g., primary, secondary or tertiary structure, effects of insulin on target cells, e.g., insulin-resistance in bodily tissues, e.g., peripheral tissues, and responses of target cells to insulin. See Braunwald, E. et al. eds. Harrison's Principles of Internal Medicine, Eleventh Edition (McGraw-Hill Book Company, New York, 1987) pp. 1778–1797; Robbins, S. L. et al. Pathologic Basis of Disease, 3rd Edition (W. B. Saunders Company, Philadelphia, 1984) p. 972 for further descriptions of abnormal insulin activity in IDDM and NIDDM and other forms of diabetes. The terms "treating" or "treatment", as used herein, refer to reduction or alleviation of at least one adverse effect or symptom of a disorder or disease, e.g., a disorder or disease characterized by or associated with abnormal or aberrant PGC-1 protein activity or PGC-1 nucleic acid expression.

As used herein, a PGC-1 modulator is a molecule which can modulate PGC-1 nucleic acid expression and/or PGC-1 protein activity. For example, a PGC-1 modulator can modulate, e.g., upregulate (activate) or downregulate (suppress), PGC-1 nucleic acid expression. In another example, a PGC-1 modulator can modulate (e.g., stimulate or inhibit) PGC-1 protein activity. If it is desirable to treat a disorder or disease characterized by (or associated with) aberrant or abnormal (non-wild-type) PGC-1 nucleic acid expression and/or PGC-1 protein activity by inhibiting PGC-1 nucleic acid expression, a PGC-1 modulator can be an antisense molecule, e.g., a ribozyme, as described herein. Examples of antisense molecules which can be used to inhibit PGC-1 nucleic acid expression include antisense molecules which are complementary to a portion of the 5' untranslated region of SEQ ID NO:1, SEQ ID NO:4 which also includes the start codon and antisense molecules which are complementary to a portion of the 3' untranslated region of SEQ ID NO:1, SEQ ID NO:4. A PGC-1 modulator which inhibits PGC-1 nucleic acid expression can also be a small molecule or other drug, e.g., a small molecule or drug identified using the screening assays described herein, which inhibits PGC-1 nucleic acid expression. If it is desirable to treat a disease or disorder characterized by (or associated with) aberrant or abnormal (non-wild-type) PGC-1 nucleic acid expression and/or PGC-1 protein activity by stimulating PGC-1 nucleic acid expression, a PGC-1 modulator can be, for example, a nucleic acid molecule encoding PGC-1 (e.g., a nucleic acid molecule comprising a nucleotide sequence homologous to the nucleotide sequence of SEQ ID NO:1, SEQ ID NO:4) or a small molecule or other drug, e.g., a small molecule (peptide) or drug identified using the screening assays described herein, which stimulates PGC-1 nucleic acid expression.

Alternatively, if it is desirable to treat a disease or disorder characterized by (or associated with) aberrant or abnormal (non-wild-type) PGC-1 nucleic acid expression and/or PGC-1 protein activity by inhibiting PGC-1 protein activity, a PGC-1 modulator can be an anti-PGC-1 antibody or a small molecule or other drug, e.g., a small molecule or drug identified using the screening assays described herein, which inhibits PGC-1 protein activity. If it is desirable to treat a disease or disorder characterized by (or associated with) aberrant or abnormal (non-wild-type) PGC-1 nucleic acid expression and/or PGC-1 protein activity by stimulating PGC-1 protein activity, a PGC-1 modulator can be an active PGC-1 protein or portion thereof (e.g., a PGC-1 protein or portion thereof having an amino acid sequence which is homologous to the amino acid sequence of SEQ ID NO:2, SEQ ID NO:5 or a portion thereof) or a small molecule or other drug, e.g., a small molecule or drug identified using the screening assays described herein, which stimulates PGC-1 protein activity.

In addition, a subject having a weight disorder, e.g., obesity, can be treated according to the present invention by administering to the subject a PGC-1 protein or portion thereof or a nucleic acid encoding a PGC-1 protein or portion thereof such that treatment occurs. Similarly, a subject having a disorder associated with insufficient insulin activity can be treated according to the present invention by administering to the subject a PGC-1 protein or portion thereof or a nucleic acid encoding a PGC-1 protein or portion thereof such that treatment occurs.

Other aspects of the invention pertain to methods for modulating a cell associated activity. These methods include contacting the cell with an agent (or a composition which includes an effective amount of an agent) which modulates PGC-1 protein activity or PGC-1 nucleic acid expression such that a cell associated activity is altered relative to a cell associated activity of the cell in the absence of the agent. As used herein, "a cell associated activity" refers to a normal or abnormal activity or function of a cell. Examples of cell associated activities include proliferation, migration, differentiation, production or secretion of molecules, such as proteins, cell survival, and thermogenesis. In a preferred embodiment, the cell associated activity is thermogenesis and the cell is a brown adipocyte. The term "altered" as used herein refers to a change, e.g., an increase or decrease, of a cell associated activity. In one embodiment, the agent stimulates PGC-1 protein activity or PGC-1 nucleic acid expression. Examples of such stimulatory agents include an active PGC-1 protein, a nucleic acid molecule encoding PGC-1 that has been introduced into the cell, and a modulatory agent which stimulates PGC-1 protein activity or PGC-1 nucleic acid expression and which is identified using the drug screening assays described herein. In another embodiment, the agent inhibits PGC-1 protein activity or PGC-1 nucleic acid expression. Examples of such inhibitory agents include an antisense PGC-1 nucleic acid molecule, an anti-PGC-1 antibody, and a modulatory agent which inhibits PGC-1 protein activity or PGC-1 nucleic acid expression and which is identified using the drug screening assays described herein. These modulatory methods can be performed in vitro (e.g., by culturing the cell with the agent) or, alternatively, in vivo (e.g., by administering the agent to a subject). In a preferred embodiment, the modulatory methods are performed in vivo, i.e., the cell is present within a subject, e.g., a mammal, e.g., a human, and the subject has a disorder or disease characterized by or associated with abnormal or aberrant PGC-1 protein activity or PGC-1 nucleic acid expression.

A nucleic acid molecule, a protein, a PGC-1 modulator, a compound etc. used in the methods of treatment can be incorporated into an appropriate pharmaceutical composition described herein and administered to the subject through a route which allows the molecule, protein, modulator, or compound etc. to perform its intended function. Examples of routes of administration are also described herein under subsection IV.

This invention is further illustrated by the following examples which should not be construed as limiting. The contents of all references, patent applications, patents, and published patent applications cited throughout this application are hereby incorporated by reference.

EXAMPLES

Example I

Identification and Characterization of Mouse PGC-1

The mouse HIB 1B cell line (Ross, R. et al. (1992) *Proc. Natl. Acad. Sci. USA* 89:7561–7565), a brown adipocyte cell line which expresses UCP, was differentiated and treated with isoproterenol to induce UCP expression. A cDNA library from the mouse HIB 1B cell line was screened in a yeast two hybrid system using PPARγ as bait and Clontech (Palo Alto, Calif.) reagents. Briefly, amino acids 183–505 of the murine PPARγ were cloned in-frame into the GAL4 DNA-binding domain plasmid pAS2. A HIB 1B cDNA expression library was constructed in the GAL4 activation domain plasmid pACT II. The yeast two-hybrid system protocol was performed as described in the CLONTECH Matchmaker two-hybrid system protocol. pAS-PPARγ was transformed into Y190 yeast cells by the lithium acetate method and maintained by selection in leucine-plates. A pACT-HIB 1B cDNA library was transformed into Y190-PPARγ yeast cells, and positive clones were assayed for β-galactosidase activity in a filter assay as described in the CLONTECH protocol. pAS1 lamin cDNA was used to obtain full-length PGC-1, the positive yeast cDNA clone was used as probe to screen an oligo dT λZAP cDNA library from HIB 1B cells.

A screen of $1 \times 10^6$ primary transformants using cDNAs prepared from HIB 1B brown fat cells yielded about 130 clones. The cDNA inserts of positive phage clones were excised into pBluescript and both strands were sequenced by standard methods. These were then analyzed for preferential expression in brown versus white fat with RNA blots. One of the clones obtained using this yeast two hybrid system was a partial PGC-1 clone which comprised nucleotides 610 to 3066 of SEQ ID NO:1. The full length clone was obtained by using a partial PGC-1 clone comprising nucleotides 650 to 3066 of SEQ ID NO:1, to screen a λZAP-HIB 1B library.

PGC-1 was then subcloned from a PBS plasmid to a PSV sport (GIBCO BRL, Gaithersburg, Md.) and in vitro translated using the TnT Promega kit (Promega, Madison, Wis.). Two bands were observed in the in vitro translated PSV sport PGC-1 which corresponded to the molecular weights of about 120 kD and 70 kD. These bands most likely represent different isoforms of PGC-1 . The 120 kD form most likely represents the protein of SEQ ID NO:2.

The nucleotide sequence of murine PGC-1 (shown in FIGS. 1A, 1B, and 1C and SEQ ID NO:1) includes 3066 nucleotides which encode a protein containing 797 amino acid residues with a predicted molecular mass of 92 kDa (FIG. 2A). The murine PGC-1 protein sequence (shown in FIGS. 1A, 1B, 1C, and 2A and SEQ ID NO:2) has several domains/motifs including Databank searches indicate that murine PGC-1 represents, a novel protein with no close homologs in any databases except expressed sequence tag (EST) databases. It does, however, contain recognizable peptide motifs including: a putative RNA-binding motif (amino acids 677–709) and two so-called SR domains, regions that are rich in serine and arginine residues (amino acids 565–598 and 617–631). Proteins containing paired RNA-binding motifs and SR domains have been shown to interact with the C-terminal domain (CTD) of RNA polymerase II (Yuryev et al. (1996) *Proc. Natl. Acad. Sci. USA* 93:6975–6980). Except for these two regions, however, PGC-1 shares no other sequence similarity with other proteins that contain these domains. In addition to these domains, PGC-1 also contains three consensus sites for phosphorylation by protein kinase A. However, no significant homology was discovered between PGC-1 and any known coactivator of nuclear receptors. PGC-1 does, however, contain one LXXLL motif (amino acids 142–146), recently identified as an element that can mediate nuclear receptor-coactivator interactions (Heery et al. (1997) *Nature* 397:733–736; Torchia et al. (1997) *Nature* 387:677–684).

From these experiments, it is clear that PGC-1 is a new factor that interacts with the adipogenic transcription factor PPARγ. Moreover, as it is known that ligands of PPARγ can induce the specific brown adipose tissue marker UCP, PPARγ is believed to play an important role in brown adipose tissue differentiation. Thus, PGC-1 modulation of PPARγ activity plays a role in brown adipose tissue differentiation, e.g., it can promote cells to differentiate into brown adipose cells rather than white adipose cells.

Example II

Identification of Human PGC-1

Northern blot analysis of human poly A RNA screened with a mouse full length cDNA probe (e.g., a probe having the sequence shown in SEQ ID NO:1) revealed high levels of expression of PGC-1 in human muscle, heart, brain, kidney and pancreas, with the highest levels of expression detected in human muscle and heart. Accordingly, a human muscle library, e.g., an human skeletal muscle oligo dT primed library (Clontech catalog #HL5023t, lot # 7110299), was screened using a full length mouse PGC-1 probe comprising the nucleotide sequence of SEQ ID NO:1 or a portion thereof (e.g., nucleotides from the 5' region of SEQ ID NO:1, e.g., nucleotides 1–50 of SEQ ID NO:1) (e.g., as described in Sambrook, J., Fritsh, E. F., and Maniatis, T. *Molecular Cloning: A Laboratory Manual. 2nd, ed, Cold Spring Harbor Laboratory,* Cold Spring Harbor Laboratory Press, Cold Spring Harbor, N.Y., 1989). Several overlapping clones were isolated and sequenced. After several rounds of screening, the longest clone isolated (clone #1[1]) contained a fragment with homology starting at amino acid 507 of the mouse sequence in SEQ ID NO:1.

Using a "5' race strategy" the full length cDNA sequence was obtained. A human PGC-1 cDNA clone was obtained with the Marathon RACE protocol and reagents available commercially through Clontech Laboratories, Inc. RACE, or rapid amplification of cDNA ends, is useful to isolate a PCR fragment comprising the native 3' or 5' end of a cDNA open reading frame, and involves use of one or more gene-specific sense (for 3' RACE) or antisense (for 5' RACE) oligonucleotide primers. The RACE protocol used is generally as described in Siebert et al. (1995), 23 *Nucl. Acids Res.* 1087–1088, and in the Clontech, Inc. *User Manual for Marathon-Ready cDNA* (1996), the teachings of which are incorporated herein by reference. The RACE reagents included the Advantage KlenTaq Polymerase mix, 10X PCR reaction buffer, 50X dNTP mix and Tricine-EDTA buffer commercially available from Clontech, Inc. The protocol is practiced with 0.5 mL PCR reaction tubes and a thermal cycling device such as the DNA Thermal Cycler 480 available from Perkin-Elmer Corporation.

A PGC-1 specific primer (ATCTTCGCTGTCATCAAACAGGCCATC (SEQ ID NO:6)), 27 bp (base-pairs) in length, was prepared for use in a 5'-RACE protocol to amplify a PCR product comprising the 5' end of human PGC-1 open reading frame in a Human Skeletal Muscle Marathon-Ready cDNA preparation (Clontech catalog # 7413-1, lot # 8030061). Thermal cycling was carried out according to the manufacturer's recommended Program 1 (a 94° C. hot start followed by 5 cycles at 94° C. to 72° C., then 5 cycles at 94° C. to 70° C., then 20–25 cycles at 94° C. to 68° C.). Confirmation that additional human PGC-1 gene sequence has been obtained can be produced by routine Southern blot analysis or by subcloning and sequencing. This fragment contained a sequence with homology extending to the most 5' sequence of mouse PGC-1 (SEQ ID NO:1). Both clone # 1[1] and the 5' RACE product were then sequenced on both strands and the full length human cDNA sequence (SEQ ID NO:4) was constituted.

The nucleotide sequence of human PGC-1 (shown in FIGS. 7A and 7B and SEQ ID NO:4) includes 3023 nucleotides which encode a protein containing 798 amino acid residues with a predicted molecular mass of 92 kDa. The human PGC-1 protein sequence (shown in FIG. 8 and SEQ ID NO:5) has several domains/motifs including Databank searches indicate that human PGC-1 represents a novel protein with no close homologs in any databases except expressed sequence tag (EST) databases.

An alignment between human PGC-1 (SEQ ID NO:5) and mouse PGC-1 (SEQ ID NO:2) amino acid sequences was performed using the BLAST software found at the National Center for Biotechnology Information (NCBI) web site (URL: http://www.ncbi.nlm.nih.gov, Altschul, S. F. et al. (1990) *J. Mol Biol* 215:403–410; Madden, T. L. et al. (1996) *Meth Enzymol* 266:131–141) and it was determined that human PGC-1 has a 94% identity to mouse PGC-1.

Example III

Tissue Distribution of Mouse PGC-1 and Cold Inducation of PGC-1 in Brown Adipose Tissue A Northern analysis of mRNA from lung, muscle, liver, heart, kidney, white adipose tissue (WAT), brown adipose tissue (BAT), brain, testis, and spleen tissue from 4 week old mice acclimated at 24° C. using a probe comprising nucleotides 150 to 3066 of SEQ ID NO:1 was performed. Briefly, total RNA was isolated from cultured cells and tissues of mouse by guanidine isothiocyanate extraction. RNA samples were processed as previously described (Tontonoz et al. (1994) *Genes Dev.* 8:1224–1234). Three bands appeared on the Northern blots that were larger than the 28S (5000–6000 bp) marker. These bands most likely represent different isoforms of PGC-1. PGC-1 mRNA was detected predominantly in brain, heart, kidney, and BAT. In addition, a minor species of approximately 8 kb is also observed in all of these tissues. In contrast, no PGC-1 mRNA expression is observed from white fat, lung, skeletal muscle, liver, testes, or spleen.

Exposure to cold is a classical inducer of adaptive thermogenesis, especially in brown fat and skeletal muscle (Himms-Hagen (1989) *Can. J Physiol. Pharmacol.* 67:394–401). A second Northern analysis of mRNA from WAT, BAT, and liver tissue from 4 week old mice acclimated at 4° C. from 3 to 12 hours using the same probe as in the first Northern analysis was performed. From this Northern analysis, it was apparent that PGC-1 was highly induced (about 30-to 50-fold) during cold exposure especially in BAT and that PGC-1 expression was BAT specific with no expression in WAT. Although PGC-1 mRNA expression is not detectable in skeletal muscle from mice kept at ambient temperature, exposure of mice to cold for 12 hr induces expression of the PGC-1 gene in this tissue. Heart and kidney, which express PGC-1 mRNA at room temperature, do not elevate this expression upon cold exposure. PGC-1 induction during cold exposure parallels that of UCP, a brown fat specific marker responsible for the thermogenic activity of BAT.

These experiments show that although PGC-1 is -expressed in several tissues, including BAT, from animals acclimated to 24° C., it is not expressed in WAT. The animal studies described herein were carried out as follows. Four-week-old male C57BL/6J mice were used. Animals were fed ad libitum and 10 animals were grouped per cage. A control group was kept at 24° C., while experimental groups were kept at 4° C. for 3 or 12 hrs. Animals were sacrificed, tissues were dissected and collected immediately.

WAT and BAT share the same genetic and biochemical machinery for adipogenesis except that BAT develops a thermogenic function upon terminal differentiation. Thus, PGC-1 plays a role in the thermogenic function of BAT. This function was confirmed when the second Northern analysis revealed that in tissues from animals acclimated at 4° C., PGC-1 was expressed essentially only in BAT. PGC-1, therefore, plays a role in the equilibrium between energy storage and expenditure.

Northern blot mRNA analysis of PGC-1 and genes of mitochondrial function in different mouse tissues (kidney, heart, BAT and WAT) after cold exposure revealed that cold-induced expression of PGC-1 in the brown fat of these mice correlated with the induced expression of other key mitochondrial proteins including ATP-synthetase (β subunit) and cytochrome c-oxidase subunits (COX II and COX IP). Although chronic cold exposure has been reported to lead to elevated activities for these mitochondrial proteins in skeletal muscle (Bourhim et al. (1990) *Am. J Physiol.* 258:R1291–R1298), no induction of mRNA for ATP-synthetase, COX II or COX IV was seen in muscle with the relatively brief exposure to cold. To conduct these experiments, animal were maintained at 4° C. for 3 or 12 hours, sacrificed and tissues (kidney, heart, WAT and BAT) were dissected for the preparation of RNA. Ten mice were pooled for each sample. Probes used for hybridization were PGC-1, UCP-1, ATP synthetase (β subunit), cytochrome c-oxidase II (COX-II), and cytochrome c-oxidase IV (COX-IV).

Cold is sensed in the central nervous system and results in increased sympathetic output to peripheral tissues, including muscle and brown fat Himms-Hagen (1989) *Can. J. Physiol. Pharmacol.* 67:394–401). Cold exposure can be mimicked, in terms of brown adipocyte precursor cell growth and the induction of UCP-1, by exposure of cultured brown fat cells to β-adrenergic agonists (Rehnmark et al. (1990) *J. Biol. Chem.* 25:16464–16471). To determine if PGC-1 gene expression is also sensitive to β-adrenergic agonists, HIB IB brown fat cells were treated with isoproterenol (1 μM), a nonsubtype selective β agonist, for 10 hr. Total cellular RNA was isolated and analyzed using PGC-1 and UCP-1 cDNA probes.

Treatment of HIB 1B brown fat cells with these agents resulted in a sharp increase in both PGC-1 mRNA and UCP-1 mRNA. Briefly, HIB 1B brown fat preadipocytes were differentiated as described herein. After 6 days, cells were approximately 80% differentiated. Exposure of brown fat cells to 9-cis retinoic acid has previously been shown to potentiate the effects of β agonists to induce UCP-1 expression (Puigserver et al. (1996) *Biochem. J.* 317:827–833). Addition of this retinoid (which activates both RXR and RAR) and isoproterenol to the HIB 1B cells resulted in a small, further increase in both PGC-1 and UCP-I expression. These results indicate that β-adrenergic agonists may play an important role in mediating the effects of cold on the induction of both UCP-1 and PGC-1.

Example IV

Recombinant Expression of PGC-1 and Binding of PGC-1 to other Transcription Factors and Nuclear Hormone Receptors GST-PGC-1 fusion proteins were generated by first subcloning a portion of the PGC-1 nucleotide sequence (nucleotides 610 to 3066 of SEQ ID NO:1) into a pGEX vector (Pharmacia Biotech Inc., Piscataway, N.J.). Briefly, PGC-1 (EcoRI-Xhol fragment from pBluescript) was cloned into the SmaI site of pGEX 5X3. The PPARγ deletions were generated by performing PCR using specific oligonucleotides and there were cloned in-frame in pGEX 5X2. These fusion proteins were expressed, and purified from *E. coli* on beads containing approximately 1 μg of protein (either GST, or alone, or fused to PGC-1), 30 μl was resuspended i the binding buffer (20 mM HEPES [pH 7.7], 75 mM KCl, 0.1 mM EDTA, 2.5 mM MgCl2, 0.05% NP40,2 mM DTT, 10% glycerol).

After expressing the fusion protein in COS cells, in vitro binding assays as described in Takeshita, A. et al. ((1996) *Endocrinology* 137:3594–3597) were performed to study the interaction of PGC-1 with PPARγ, other PPAR isoforms such as PPARα and PPARδ, other transcription factors such as C/EBPα and RXRα, and other nuclear hormone receptors such as the thyroid hormone receptor, the estrogen receptor, and the retinoic acid receptor. The assays were carried out as follows. Control GST protein alone or PGC-1 (aa 36–797) fused to GST were immobilized on glutathione agarose beads and incubated with different in vitro-translated ([$^{35}$S] methionine-labeled nuclear receptors and appropriate ligands or vehicle. The fusion proteins were mixed with 5 μl of different nuclear receptors made in an in vitro reticulocyte translation reaction using [$^{35}$S] methionine (Promega TNT reticulocyte lysate system kit). Specific nuclear receptor ligands or vehicle (5 µl) was added. Binding was performed for 60 min. at room temperature. The beads were then washed four times with the binding buffer with or without ligands and resuspended in SDS-PAGE sample buffer. After electrophoresis, fixation, and enhancement, the radiolabeled proteins were visualized by autoradiography.

These assays show that PGC-1 interacted with PPARγ. This interaction was not ligand-dependent, in that addition of BRL49653 (a thiazolidinedione ligand for PPARγ) at 10 µM does not significantly alter this binding. A similar lack of ligand dependence for this interaction was seen when bacterially expressed PPARγ was immobilized on beads and used with reticulocyte-translated PGC-1. These assays also showed that PGC-1 interacts with: a) PPARα and shows a slight ligand dependency using leukotriene-4 (1 µM); b) PPARδ and shows a slight ligand dependency using carboprostacyclin (1 µM); c) the thyroid hormone receptor with a slight ligand dependency using thyroid hormone (1 µM); d) the estrogen receptor with a slight ligand dependency using estradiol (1 µM); and 3) the retinoic acid receptor with a strong ligand dependency using all-trans retinoic acid (1 µM). The TRβ also binds specifically to PGC-1, though in this case ligand ($T_3$) addition causes a 2-to 3-fold increase in binding. A strong ligand-dependent binding is seen between PGC-1 and the retinoic acid (RA) receptor, and between PGC-1 and the estrogen receptor (ERα). In contrast, little or no binding is seen between PGC-1 and the retinoid-X receptor (RXRα), with or without ligand addition. These data indicate that PGC-1 interacts specifically with PPARγ and several other nuclear receptors in vitro. There is a broad range of dependence on ligand for these interactions, from no ligand dependence (PPARγ) to a strong dependence on ligand addition (RARα).

The interaction between PPARγ and PGC-1 can also be seen in mammalian cells. Even in the absence of added ligand, an association is observed between these two proteins in immunoprecipitation assays. Vectors expressing HA-tagged PGC-1 and PPARγ were transfected into COS cells. In brief, full-length PGC-1 with an HA-tagged N terminus was generated by PCR and closed into SmaI of pSV-SPORT. Ligands pioglitazone (5 µM), 9-cis RA (1 µM), and 8-Br-cAMP (1 nm) were added 3 hrs. before cells were harvested. Cell extracts and immunoprecipitation from transfected cells were performed as in Lassar et al. ((1991) Cell 66:305–315). Rabbit anti-murine PPARγ (Hu et al. (1996) Science 274:2100–2103) was used as a 1:500 dilution for immunoprecipitation. An anti-HA mouse dilution for Western blot that was developed using ECL (Amersham). When cells are treated with pioglitazone (a PPARγ ligand), a very modest increase in association is observed.

To address whether PGC-1 does indeed reside in the cell nucleus, a fusion protein between PGC-1 and green fluorescent protein (GFP) was constructed. GFP fused to the full-length PGC-1 was generated by closing this (Clontech). Cellular localization was visualized 24 hrs. after transfection using a Nikon Diaphora 200 microscope. When GFP-PGC-1 is expressed in COS cells, it is observed entirely in the cell nucleus.

These results show that PGC-1 binds not only to PPARγ but also to other nuclear hormone receptors, and thus this molecule can be used to modulate the function of these additional nuclear hormone receptors. PGC-1 can be used as a target for screening molecules which modulate the function of these nuclear hormone receptors. Moreover, the fact that PGC-1 interacts with the thyroid hormone receptor and the retinoic acid receptor is important in brown adipocyte function as both of these receptors can transcriptionally regulate UCP expression.

Example V

PGC-1 Acts as a Coactivator with PPARγ/PXRα and TR to induce Expression of a Gene Under The Control of UCP Regulartory Elements To assess the transcription activity of PGC-1, an in vitro transcriptional assay was performed. The UCP-1 promoter has been shown to have binding sites for both PPARγ and the TR (Cassard-Doulcier et al. (1994) J. Biol. Chem. 269:24335–24342; Sears et al. (1996) Mol. Cell. Biol. 16:3410–3419). In this assay, the full length promoter and enhancer of UCP was linked to the CAT reporter gene. RAT IR (a rat fibroblast cell line transformed to express the human insulin receptor) cells were transiently transfected with PSV-sport alone (control), PPARγ/RXRα, PGC-1, and PPARγ/RXRα/PGC-1 using the calcium phosphate method. Results from CAT assays were controlled for transfection efficiency by cotransfection of a β-galactosidase reporter gene under the control of the CMV promoter. In each case, the cells were treated with either dimethyl sulfoxide or a combination of 9-cis retinoic acid, 8-Br-cAMP, and the synthetic PPARγ ligand pioglitazone (PIO). Transcriptional activity was seen in the cells treated with the combination of 9-cis retinoic acid, 8-Br-cAMP, and PIO and containing PGC-1 alone, cells containing PPARγ/RXRα, and cells containing PPARγ/RXRα/PGC-1. Maximum activity was seen in cells treated with the combination of 9-cis retinoic acid, 8-Br-cAMP, and PIO and containing PPARγ/RXRα/PGC-1. These results indicate that PGC-1 acts as a positive transcriptional coactivator of PPARγ/RXRα.

To determine which inducers were involved in the transcriptional activation of PGC-1, the cells were treated individually (PIO, the synthetic PPARγ ligand troglitazone (TRO), 9-cis retinoic acid, 8-Br cAMP) and in combination (9-cis retinoic acid in combination with 8-Br cAMP) with different inducers. With regard to the cells treated with the individual inducers, it was found that the potency of the inducers was as follows (from highest to lowest): 9-cis retinoic acid, 8-Br cAMP, TRO, and then PIO. The combination of 9-cis retinoic acid and 8-Br cAMP was more potent in enhancing transcriptional activity than any of the individual inducers.

Similarly, TRβ/RXRα combination alone induced very little transcriptional activity, even when stimulated with a ligand cocktail including $T_3$ (1 µM). However, the combination of PGC-1 with the TRβ/RXRα pair induced powerful transactivation, again in a ligand-dependent manner. These results clearly indicate that PGC-1 can function as a potent transcriptional coactivator for PPARγ and the TR. It is interesting that the optimal transcriptional response is seen with PPARγ ligand is added, despite the fact that the binding of PGC-1 and PPARγ is not ligand dependent. It is likely that this results from simultaneous, ligand-dependent docking of another coactivator, such as SRC-1, CBP, or others.

The role of different hormones and ligands used to achieve maximal transcriptional activation with PPARγ and PGC-1 is dissected in FIG. 3A. The individual components -troglitazone (trog.), 9 cis-retinoic acid (9cRA), and 8-bromo cyclic AMP (cAMP) -each stimulate a 2-to 4-fold increase in transcriptional activity. The fold activation was compared to the value observed in cells transfected with the same vectors but not treated with ligand. However, the most robust responses are seen when they are used in combination. The synergistic effect of 9-cis retinoic acid and 8-bromo cyclic AMP is particularly striking (14-fold), while all three agents together cause an 18-fold increase above the untreated control.

The above-described transcriptional assay represents a useful assay for screening compounds or agents which can modulate, e.g., stimulate or inhibit, the function of PGC-1 alone and/or PGC-1 in combination with PPARγ/RXRα. Based on the results reported in this Example, agents which likely modulate UCP expression and thus thermogenesis in BAT include PGC-1 molecules, PPARγ ligands (e.g., thiazolidinediones, e.g., PIO and TRO), retinoids, and adrenergic agonists.

Example VI

Identification of the Domains that Mediate the PGC-1-PPARγ Interaction

The interaction between nuclear receptors and certain coactivators such as SRC-1 or CBP is ligand dependent (Kamai et al. (1996) *Cell* 84:403–414) and involves an LXXLL (SEQ ID NO:3) motif in the coactivators and the C-terminal AF-2 domain in the receptors (Heery et al. (1997) *Nature* 387:733–736; Torchia et al. (1997) *Nature* 387:677–684). To identify the domains responsible for PGC-I-PPARγ interactions, different C-terminal deletions of PGC-1 were generated as reticulocyte translation products and mixed with a FST-PPARγ fusion protein. Deletions of PGC-1 were made using specific restriction sites in the PGC-1 were made using specific restriction sites in the PGC-1 cDNA closed in pBluescript. The following restriction enzymes were used for these deletions: full-length XhoI (aa-1–797), HaeII (aa 1–675) NcoI (aa 1–503), XbaI (aa 1–403), KpnI (aa 1–338), and StuI (aa 1–292). These were then translated into vitro with an [$^{35}$S]methionine-label. One microliter of each in vitro translation reaction was resolved by SDS-PAGE and autoradiographed.

Figure 4:
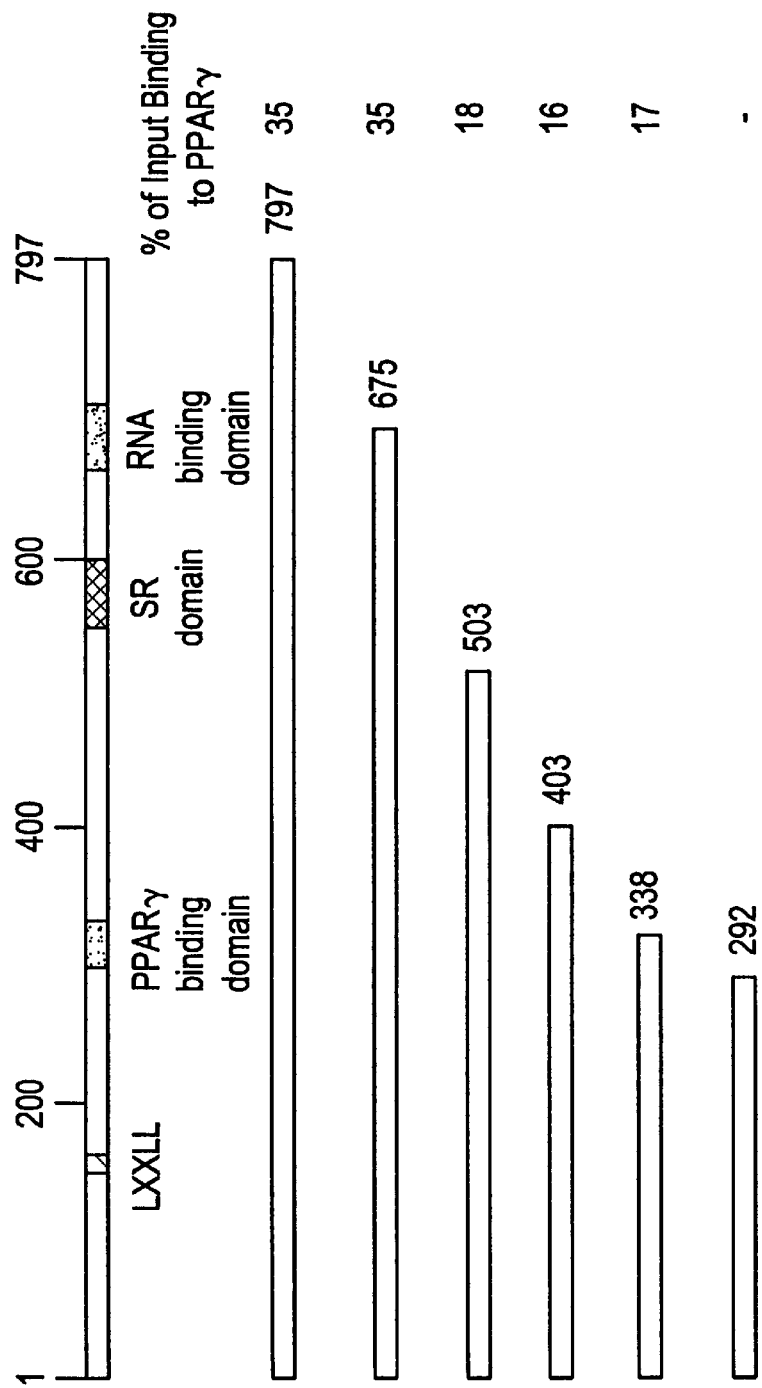
FIG. 4 is a diagram of different mouse PGC-1 deletions to identify the domain of PGC-1 which interacts with PPARγ. Indicated in the Figure are schematic representations of the PGC-1 deletions with the corresponding percentage of input material that bound to PPARγ. The LXXLL (SEQ ID NO:3) motif is located at amino acid residues 142–146. The black box corresponds to the PPARγ-binding domain of PGC-1 (amino acid 292–338).

FIG. 4 summarizes the input of both the full-length PGC-1 (1–797) and the 1–675 deletion which bind to the immobilized PPARγ. The binding of PGC-1 1–503, which lacks the SR and RNA-binding domains, is modestly decreased to 18%. A similar level of binding can be seen for PGC-1 1–403 and 1–338. However, PGC-11-292, which still contains the LXXLL (SEQ ID NO:3) motif, completely loses the ability to interact with PPARγ. As shown in FIG. 2A, residues 292–338 contain no distinct domains known to mediate protein-protein interaction, though it is very rich in proline residues.

Figure 5:
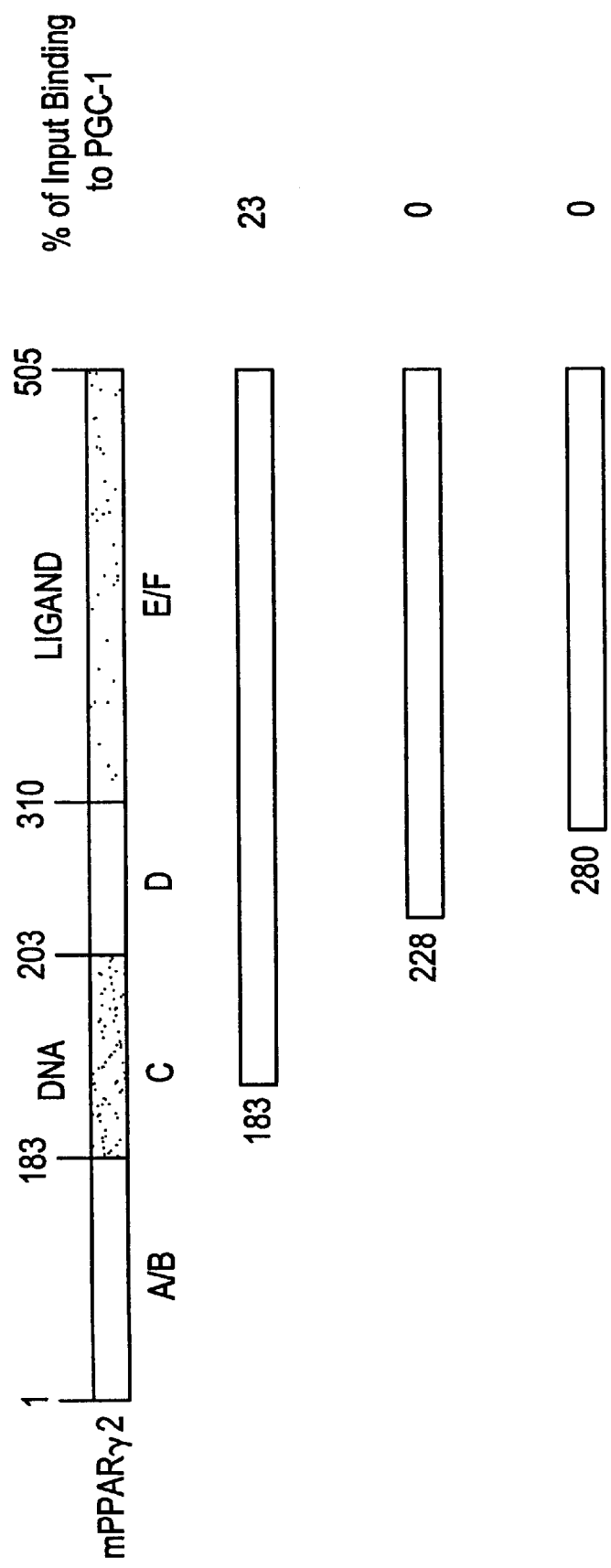
FIG. 5 is a diagram of different mouse PPARγ deletions to identify the domain of PPARγ which interacts with PGC-1. Indicated in the Figure are schematic representations of the PPARγ deletions with the corresponding percentage of input binding to PGC-1.

Most of the nuclear hormone receptor coactivators identified to date interact with the C-terminal AF-2 domain, which is responsible for ligand-dependent transcriptional activation. To determine if PGC-1 also interacts with this part of PPARγ, several deletions of PPARγ prepared as GST fusion proteins were used and combined with in vitro-translated PGC-1. FIG. 5 shows that amino acids 181–505 of PPARγ (the original fragment used in the yeast two-hybrid screen) interact strongly with PGC-1, pulling down 23% of the input. On the other hand, a further deletion of 45 amino acids (228–505) is not able to bind to full-length PGC-1. Both of these PPARγ deletions were able to bind SRC-1, indicating that they have not lost their general ability to interact with other proteins. These data demonstrate that PPARγ utilizes part of its DNA-binding and hinge domains to bind PGC-1. It apparently does not interact through the C-terminal AF-2 domain that docks other coactivators such as SRC-1 and CBP.

Example VII

Transcriptional Activity and Deletion Analysis of PGC-1

To address whether PGC-1 has its own transcriptional activation domain or contains some activity that might unmask or augment the transcriptional activator properties of the nuclear receptors, a number of fusion proteins between full length or portions of PGC-1 and the DNA-binding domain (DBD) of GAL4 were prepared and assayed transcription through a GAL4 DNA binding target sequence, the UAS. Transcription was assayed with a reporter plasmid containing five copies of the UAS linked to CAT. More specifically, transcriptional activation assays were performed as follows. An expression plasmid containing full-length PGC-1 was constructed by first ligating the entire 3 kb cDNA as a Small-XhoI fragment into Smal-SalI sites of pSV-SPORT (GIBCO-BRL). This was expressed in cells with -CMX vector, along with a control fusion between GAL4 DBD and full-length murine SRCl. The activity stimulated by 4.5 μg of the DBD-PGC-1 was set as 100%. The −3740/+110 bp UCP promoter was described previously (Kozak et al. (1994) *Mol. Cell. Biol.* 14:59–67). Rat1 IR fibroblasts were cultured in DMEM containing 10% cosmic calf serum and transfected at 80%–90% confluence by the calcium phosphate method. Ligands were dissolved in a vehicle containing 0.1 % DMSO (9-cis retinoic acid and troglitazone) or water (8-bromocAMP). Transfections were performed in duplicate and repeated at least three times. CAT activity was assayed as described in Kim and Spiegelman ((1996) *Genes Dev.* 10:1096–1107).

For GAL4 fusion constructs, full-length PGC-1 generated by PCR was cloned in-frame into the SalI-EcoRV sites of pCMX-GAL4 plasmid. Murine full-length SRC-1 was cloned into the SmaI site of RSV.GAL4.COS cells were transfected in the same way as Rat1 IR fibroblasts and the reporter was the 5xUASg-CAT.

As shown in FIG. 3B, PGC-1 can activate transcription readily when tethered to DNA by the GAL4 DBD. For comparison, the results obtained by fusion of the GAL4 DBD with another coactivator of nuclear receptors, SRC-1, is shown. Thus, PGC-1 does not absolutely require docking to a nuclear receptor to demonstrate transcriptional activation function; it is likely that its interaction with these receptors serves primarily to bring PGC-1 to appropriate DNA sites.

To further determine the location of the transcriptional activation domain of PGC-1, a number of deletion mutants fused to a GAL4 DNA binding domain were tested for the induction of a luciferase reporter gene as described above. The following constructs were tested: control GAL-4 alone, GAL4-PGC-1, GAL4-amino acids 1–65 of PGC-1, GAL4-amino acids 1–125 of PGC-1, GAL4-amino acids 1–170 of PGC-1, GAL4-amino acids 1–350 of PGC-1, GAL4-amino acids 1–550 of PGC-1, GAL4-amino acids 1–650 of PGC-1, GAL4-amino acids 1–650 of PGC-1, and GAL4-amino acids 170–797 of PGC-1. The results are summarized below in Table 1.

TABLE 1

Transcription Activity of PGC-1-GAL-4 constructs

| CONSTRUCT | LUCIFERASE UNITS |
| --- | --- |
| GAL 4 Alone | 4 |
| GAL4-PGC-1 | 700 |
| GAL4 1-65 | 4800 |
| GAL4 1-125 | 84,000 |
| GAL4 1-170 | 36,000 |
| GAL4 1-350 | 700 |
| GAL4 1-550 | 4,300 |
| GAL4 1-650 | 300 |
| GAL4 170-797 | 4 |

As shown in Table 1, GAL4-PGC-1 constructs containing the N-terminal region of the molecule ) show a higher transcriptional activity than the full length molecule. The construct GAL4 170–797 showed no detectable transcriptional activity. These results indicate that the transcriptional activation domain of PGC-1 is located at the N-terminal region of the molecule and in particular, at amino acids 1–1 70 of PGC-1. The decreased in transcriptional activity observed as C-terminal amino acid residues are included (e.g., compare the transcriptional activity of GAL4 1–125 and the full length molecule) suggests that these C-terminal residues may inhibit the transcriptional activity of the N-terminal domain by, e.g., masking this domain or by interacting with other proteins which may mask or otherwise antagonize the activity of this domain.

The above-described assay and constructs provide a useful assay for screening compounds or agents which can modulate, e.g., stimulate or inhibit, the function of PGC-1. Particularly, preferred compounds or agent include activators of PGC-1, e.g., agents that antagonize the inhibitory effect of the C-terminal portion of the molecule. These compounds or agents can be useful in modulating thermogenesis.

Example VIII

Role of Protein Kinase a in Modulating PGC-1 Activity

Expression of UCP genes is highly sensitive to cAMP. Analysis of the PGC-1 sequence revealed three consensus sites for phosphorylation by protein kinase A (FIG. 2A and 2B). This finding suggests a potential role of this kinase in regulating the activity of PGC-1, which in tun would modify UCP gene expression. To address this possibility, site directed mutagenesis can be performed to ablate these phosphorylation sites. For example, amino acids 373–376 of SEQ ID NO:2 can be mutated using standard protocols. The transcriptional activity of the resulting mutants can be tested in, e.g., COS cells or HeLa cells, carrying a reporter gene, e.g., a CAT gene, under the control of an UCP promoter.

Example IX

ECTOPIC EXPRESSION OF PGC-1 INDUCES MOLECULAR COMPONENTS OF ADAPTIVE THERMOGENESIS

To examine directly the ability of PGC-1 to regulate the genes of adaptive thermogenesis, retroviral vectors have been used to express this protein in white fat precursor cells, and 3T3-F442A preadipocytes were then stimulated to differentiate. Briefly, the PGC-1 viral expression vector (pBabe-PGC-1) was constructed by ligating the BamHI-XhoI fragment from pBluescript-PGC-1 plasmid into BamHI/SalI sites of pBabe-puro. Following drug selection, virally infected 3T3F442A-PGC-1 and 3T3F441-vector cells lines were grown to confluence in DMEM with 10% BCS. Differentiation of these cells was initiated by culturing them in DMEM insulin. Cells were refed every 2 days with this medium. Specific cells were grown in DMEM with 10% CCS to confluence. These cells were then treated with 1 µM dexamethasone, 0.5 mM of methyl-isobutyl-xanthine, 125 µM indomethacin, 17 nM insulin, and 1 nM $T_3$ for 48 hrs. to induce differentiation. Cells were subsequently maintained in DMEM containing 10% CCS, 17 nM insulin, and 1 nM $T_3$ and replenished every 2 days. After these treatments, total RNA was isolated and analyzed.

To induce UCP-1 expression, 1 µM 8-bromo-cAMP and 1 mM 9-cis-retinoic acid were added to the medium, and total RNA was extracted from the cells 6 hr later. Northern blot analysis with a PGC-1 probe revealed that PGC-1 mRNA was barely detectable in these white fat cells infected with empty vectors but was more highly expressed in cells infected with the viruses containing the PGC-1 cDNA. The expression of this mRNA in the cultured cells was approximately 6% of that seen in the brown fat of cold exposed mice. mRNA for UCP-1, the classic marker of brown fat cells that is encoded in the cell nucleus, is barely detectable in the control 3T3-F442A cells but is significantly induced in the cells expressing PGC-1. mRNA for ATP synthetase, a key mitochondrial protein involved in oxidative phosphorylation that is also encoded in the nucleus, is likewise increased in the cells expressing PGC-1. The mitochondrial respiratory enzyme cytochrome c-oxidase subunits COX II and IV are encoded in the mitochondrial and nuclear genome, respectively. Both of these mRNAs increase 2-to 3-fold in the cells ectopically expressing PGC-1. Expression of aP2, a white and brown fat cell gene not linked to thermogenesis, and 36B4, a ribosomal protein are shown as a loading control. These results demonstrate that PGC-1 can stimulate the expression of several key genes of mitochondrial function and adaptive thermogenesis, even when expressed at levels far below those seen in cold-exposed animals.

The ability of PGC-1 to affect the expression of mRNA for a protein (COX-II) encoded in the mitochondrial genome suggests that PGC-1 could affect the biogenesis of mitochondria per se. Changes in the cellular content of mitochondrial DNA have been used as a simple biochemical assay for mitochondrial proliferation (Martin et al. (1995) *Biochem. J.* 308:749–752; Klingenspor et al. (1996) *Biochem. J.* 316:607–613). To address this possibility, Southern blot analysis of mitochondrial DNA was performed. 3T3-F442A Southern blots were carried out by isolating and processing genomic DNA as described in Maniatis et al. (1989) *Molecular Cloning: A Laboratory Manual,* 2nd Ed. (Cold Spring Harbor, N.Y.: Cold Spring Harbor Laboratory Press)). 3T3-F442A cells were differentiated as described above. Total cellular DNA was isolated and was digested with NCo I. Ten micrograms of DNA were electrophoresed, and the Southern blot was hybridized using COX-II cDNA as a probe for mitochondrial DNA.

Southern blot analysis of mitochondrial genome DNA revealed that cells expressing PGC-1 have twice the mitochondrial DNA content compared to control cells. The sane blots were also probed with cDNA for 36B4, a ribosomal protein encoded in the nucleus. The blot was then stripped and hybridized with the nuclear gene 3664. These results show that ectopic PGC-1 expression can stimulate an increase in mitochondrial DNA, indicating an increased biogenesis of mitochondria.

Example X

Chronic Treatment of PGC-1 Infected Cells Increasing Oxygen Consumption

To determine a physiological role for PGC-1 in mediating thermogenesis, oxygen consumption assays were performed using 3T3-F442A preadipocytes infected with PGC-1-expressing retroviral vectors as described above. The efficiency of infection is estimated to be 25%–30% of the cells. Oxygen consumption assays were performed as described in Ludwik, J. et al. (1981) *J. Biochemistry* 256(24): 12840–12848 and Hermesh, O. (1998) *J. Biochemistry* 273(7): 3937–3942. Treatment of these cells with 1 $\mu$M 8-bromo-cAMP and 1 mM 9-cis-retinoic acid for 6 hours resulted in a 100% increase in oxygen consumption by these cells (FIG. 6). The increase in oxygen consumption detected in these cells is likely to be caused by an increase in the activity and/or expression of mitochondrial uncoupling proteins (UCPs) or similar proteins which may facilitate proton transport.

These experiments demonstrate that PGC-1 is capable of mediating a thermogenic response in vivo, thus linking directly the induction of mitochondrial DNA and gene expression to a physiological response. The physiological function of PGC-1 can be further characterized in tissues known to expressed high levels of this molecule, such as muscle. For example, mouse myoblast cells which can be induced to differentiate into myotube such as C2–C 12 cells, can be infected with a retrovirus expressing PGC-1 and tested under the conditions described above.

Example XI

PGC-1 is a Unique Nuclear Receptor Coactivator

The results presented herein show that PGC-1 is unusual among known nuclear receptor coactivators in that its expression is dramatically regulated with respect to both tissue selectivity and the physiological state of the animal. The expression of PGC-1 in BAT but not WAT distinguishes it from most known transcriptional components in these tissues and its induction by cold is even more dramatic than that observed for UCP-1. PGC-1 is also distinct from the known coactivators in that it appears to use different sequence motifs for protein-protein docking, on both sides of the receptor-coactivator pair. Nearly all of the known coactivators and corepressors utilize LXXLL (SEQ ID NO:3) sequences to bind at the ligand-regulated helix 12 in the carboxy terminal AF-2 domain (Heery et al. (1997) *Nature* 387:733–736; Torchia et al. (1997) *Nature* 387:677–684. In contrast, PGC-1 utilizes a domain rich in proline residues to bind to a region that overlaps the DNA binding and hinge region of PPAR$\gamma$. For PPAR$\gamma$, this opens the possibility that PGC-1 is not an alternative coactivator to one or more of the ligand-controlled coactivators but, rather, may bind in concert with these proteins to give a larger macromolecular complex. On the other hand, ligand-dependent docking is seen with some other receptors such as the retinoic acid receptor, the estrogen receptor, and to a certain degree, the thyroid receptor. Since PGC-1 has one LXXLL (SEQ ID NO:3) sequence, a motif shown in several contexts to be both necessary and sufficient for ligand-dependent receptor docking, it is entirely possible that the binding of PGC-1 to those receptors will depend on this sequence and the receptor AF-2 domains.

It is now appreciated that most of the coactivators or corepressors that bind to receptors at AF-2 domains carry either histone acetyltransferase or histone deacetylase activities (Pazin and Kadonaga (1997) *Cell* 89:325–328). These activities may be intrinsic to certain coactivators such as CBP and SRC-1 (Bannister and Kouzarides, (1996) *Nature* 384:641–643; Spencer et al. (1997) *Nature* 389:194–198) or reside in proteins that form complexes with corepressors, as illustrated by the complex between SMRT and mammalian histone deacetylase (Nagy et al. (1997) *Cell* 89:373–380; Torchia et al. (1997) *Nature* 387:677–684. Based on primary sequence data, PGC-1 does not contain any motifs that would be suggestive of histone acetylase or deacetylase activity. It also has no significant sequence homologies with any of the known nuclear receptor coactivators or corepressors. It may be noteworthy that PGC-1 has paired SR and RNA-binding domains that have been identified in a number of proteins, including several that bind to the regulatory carboxy terminal domain (CTD) of RNA polymerase II (Yuryev et al. (1996) *Proc. Natl. Acad. Sci. USA* 93:6975–6980. The findings presented herein could also be explained by PGC-1 relieving a gene repression mechanism. The hinge region of at least one nuclear receptor (TR) has been shown to be involved in binding a corepressor (N-CoR; Horlein et al. (1995) *Nature* 377:397–404. Hence, PGC-1's action may be to derepress transcription by interfering with corepressor binding.

Example XII role of PGC-1 In Adaptive Thermogenesis

Adaptive thermogenesis refers to a component of energy expenditure, which is separate from physical activity and which can be elevated in response to changing environmental conditions, most notably cold exposure and overfeeding (Himms-Hagen (1989) *Proc. Soc. Exp. Biol. Med.* 208:159–169). There is considerable interest in this subject because of its potential roles in both the pathogenesis and therapy of human obesity.

A role for PGC-1 in adaptive thermogenesis is indicated first by its connection to the key tissues and hormones implicated in this process. The results shown herein suggest an especially important role for skeletal muscle and brown fat. PGC-1 is induced by cold exposure in both muscle and brown fat but not in other tissues. The thermogenic and antiobesity properties of brown fat are conclusively established in rodents (Himms-Hagen (1995) *Proc. Soc. exp. Biol. Med.* 208:159–169), but the role of BAT is less clear in humans due to the fact that adult humans and other large mammals do not have well-defined brown fat depots. The expression of UCP-1 in the white fat depots of adults suggests that brown adipocytes may be incorporated into depots that appear white and can be recruited upon adrenergic stimulation (Garruti and Ricquier, (1992) *Int. J. Obes. Relat. Metab. Disord.* 16:383–390).

With regard to hormones, thyroid hormone and 0-adrenergic agonists appear to play the most important roles in both cold and diet-induced thermogenesis in muscle and brown fat (Himms-Hagen (1989) *Proc. Soc. Exp. Biol. Med.* 208:259–269; Cannon and Nedergaard (1996) *Biochem. Soc. Trans.* 24:407–412). $\beta$-adrenergic agonists appear to affect PGC-1 function in at least two distinct ways. First, they can induce PGC-1 expression. Second, cyclic AMP (the intracellular mediator of β-adrenergic receptor activity) increases the transcriptional activity mediated by PGC-1 when expression is driven ectopically, as shown in FIG. 3B. While the molecular basis of this is not known, the presence of three consensus phosphorylation sites for protein kinase A suggests that the protein may be posttranslationally activated by this pathway. The thermogenic effects of thyroid hormone and its receptors are well known. One of the clearest effects of increasing thyroid hormone levels is the stimulation of mitochondrial respiration rates in skeletal muscle, brown fat, heart, and kidney. Abnormally low respiration rates, characteristic of a hypothyroid state, can be increased by raising thyroid hormone levels (Pillar and Seitz (1997) Eur. J. Endocrinol. 135:231–239). Based on the tissues where it is expressed and its ability to coactivate the TR, PGC-1 appears to be a very good candidate to mediate some of these effects.

Recent evidence has also suggested interesting effects of the TZDs in thermogenesis. These PPARγ ligands can increase energy expenditure when given systematically to rodents, perhaps due to increased formation of brown fat and an increase in Ucp-1 gene expression. These effects have also been seen in cultured cells (Foellmi-Adams et al. (1996) Biochem. Pharmacol. 52:693–701; Tai et al., J. Biol. Chem. 271:29909–29914 (1996). The ability of PGC-1 to coactivate the function of PPARγ on the UCP-1 promoter, and presumably other promoters in thermogenic pathways, may provide some explanation for these effects.

In addition to these associations described above, ectopic expression experiments presented here show more directly that PGC-1 can regulate components of thermogenesis. At a cellular and molecular level, adaptive thermogenesis consists of at least three separable processes: the biogenesis of mitochondria, the expression of the mitochondrial enzymes of the respiratory chain, and the expression of specific uncoupling proteins. There are now three known members of the UCP gene family; UCP-1, expressed exclusively in brown fat; Ucp-2, expressed widely, and Ucp-3, expressed primarily in skeletal muscle and brown fat. Depending on the length of time and severity of a given physiological challenge, one or more of these aspects of thermogenesis may be affected in muscle, BAT, or other tissues.

The retroviral expression of PGC-1 described herein have used white fat cells. This cell type was chosen because it has little endogenous PGC-1 expression and is known to have relatively low numbers of mitochondria and little expression of UCP-1 or UCP-3. Although we were only able to get a relatively low level of PGC-1 mRNA expression (6% of that seen in cold-induced BAT), it is clear that several molecular components of the adaptive thermogenesis system are altered. First, expression of the Ucp-1 gene is turned on from the almost undetectable level that is characteristic of these white cells. Second, several mitochondrial genes of the respiratory chain that are ordinarily expressed in these cells, such as ATP synthetase, Cox-II and Cox-IV, are significantly increased. Finally, mitochondrial content is doubled, as evidenced by the increase in mitochondrial DNA per unit of total cellular DNA.

The mechanism by which PGC-1 may regulate mitochondrial processes linked to adaptive thermogenesis can be as follows. For genes such as UCP-1 that are encoded in the nucleus and are responsive to PPAR, TR, or other nuclear receptors, PGC-1 could act directly as a coactivator to increase transcription rates. For genes that are encoded in the mitochondrial genome (such as Cox-II), PGC-1 could be acting directly or indirectly. Certain genes within the mitochondria have been shown to have functional thyroid response elements (TREs; Pillar and Seitz (1997) Eur. J Endocrinol. 135:231–239). While PGC-1 is observed mainly in the nucleus, a small percentage of the TR and PGC-1 are transported into the mitochondria and function directly at these sites. Similarly, with regard to mitochondrial DNA replication, the D loop of the mitochondrial genome is a site of heavy strand replication and contains a TRE-DR2 sequence (Wrutniak et al., (1995) J. Biol. Chem. 270:16347–16354), suggesting that the TR and PGC-1 could act here directly. On the other hand, PGC-1 and nuclear receptors could regulate the expression of other nuclear factors, such as NRF or mitochondrial factor A, that have been shown to function in the mitochondria to stimulate gene transcription and/or DNA replication (Pillar and Seitz, (1997) Eur. J Endocrinol. 135:231–239).

The contents of all cited references (including literature references, issued patents, published patent applications, and co-pending patent applications) cited throughout this application (including the Background Section) are hereby expressly incorporated by reference. The entire contents of Appendix A (including the Figures depicted therein) entitled "A Cold-Inducible Coactivator of Nuclear Receptors Linked to Adaptive Thermogenesis" is also incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated antibody that specifically binds PGC-1.

2. A method for detecting the presence of PGC-1 in a biological sample comprising contacting a biological sample with an agent capable of detecting PGC-1 protein or mRNA.

3. A kit for detecting the presence of PGC-1 in a biological sample comprising a labeled or labelable agent capable of detecting PGC-1 protein or mRNA in a biological sample; means for determining the amount of PGC-1 in the sample; and means for comparing the amount of PGC-1 in the sample with a standard.

4. A method for identifying a compound capable of treating a disorder characterized by aberrant PGC-1 nucleic acid expression or PGC-1 protein activity comprising assaying the ability of the compound or agent to modulate the expression of PGC-1 nucleic acid or the activity of the PGC-1 protein thereby identifying a compound capable of treating a disorder characterized by aberrant PGC-1 nucleic acid expression or PGC-1 protein activity.

5. A method for identifying a compound which binds to PGC-1 protein comprising contacting the PGC-1 protein with the compound under conditions which allow binding of the compound to the PGC-1 protein to form a complex; and detecting the formation of a complex of the PGC-1 protein and the compound in which the ability of the compound to bind to the PGC-1 protein is indicated by the presence of the compound in the complex.

6. A method for identifying a compound which inhibits the interaction of the PGC-1 protein with a target molecule comprising contacting, in the presence of the compound, the PGC-1 protein and the target molecule under conditions which allow binding of the target molecule to the PGC-1 protein to form a complex; and detecting the formation of a complex of the PGC-1 protein and the target molecule in which the ability of the compound to inhibit interaction between the PGC-1 protein and the target molecule is indicated by a decrease in complex formation as compared to the amount of complex formed in the absence of the compound.

* * * * *

SEQUENCE LISTING

<160> NUMBER OF SEQ ID NOS: 6

<210> SEQ ID NO 1
<211> LENGTH: 3066
<212> TYPE: DNA
<213> ORGANISM: Mus musculus
<220> FEATURE:
<221> NAME/KEY: CDS
<222> LOCATION: (92)..(2482)

<400> SEQUENCE: 1
aattcggcac gaggttgcct gcatgagtgt gtgctgtgtg tcagagtgga ttggagttga      60

-continued

```
aaaagcttga ctggcgtcat tcgggagctg g atg gct tgg gac atg tgc agc          112
                                  Met Ala Trp Asp Met Cys Ser
                                   1               5 caa gac tct gta tgg agt gac ata gag tgt gct gct ctg gtt ggt gag         160
Gln Asp Ser Val Trp Ser Asp Ile Glu Cys Ala Ala Leu Val Gly Glu
         10                  15                  20 gac cag cct ctt tgc cca gat ctt cct gaa ctt gac ctt tct gaa ctt         208
Asp Gln Pro Leu Cys Pro Asp Leu Pro Glu Leu Asp Leu Ser Glu Leu
     25                  30                  35 gat gtg aat gac ttg gat aca gac agc ttt ctg ggt gga ttg aag tgg         256
Asp Val Asn Asp Leu Asp Thr Asp Ser Phe Leu Gly Gly Leu Lys Trp
 40                  45                  50                  55 tgt agc gac caa tcg gaa atc ata tcc aac cag tac aac aat gag cct         304
Cys Ser Asp Gln Ser Glu Ile Ile Ser Asn Gln Tyr Asn Asn Glu Pro
                 60                  65                  70 gcg aac ata ttt gag aag ata gat gaa gag aat gag gca aac ttg cta         352
Ala Asn Ile Phe Glu Lys Ile Asp Glu Glu Asn Glu Ala Asn Leu Leu
             75                  80                  85 gcg gtc ctc aca gag aca ctg gac agt ctc ccc gtg gat gaa gac gga         400
Ala Val Leu Thr Glu Thr Leu Asp Ser Leu Pro Val Asp Glu Asp Gly
         90                  95                 100 ttg ccc tca ttt gat gca ctg aca gat gga gcc gtg acc act gac aac         448
Leu Pro Ser Phe Asp Ala Leu Thr Asp Gly Ala Val Thr Thr Asp Asn
    105                 110                 115 gag gcc agt cct tcc tcc atg cct gac ggc acc cct ccc cct cag gag         496
Glu Ala Ser Pro Ser Ser Met Pro Asp Gly Thr Pro Pro Pro Gln Glu
120                 125                 130                 135 gca gaa gag ccg tct cta ctt aag aag ctc tta ctg gca cca gcc aac         544
Ala Glu Glu Pro Ser Leu Leu Lys Lys Leu Leu Leu Ala Pro Ala Asn
                140                 145                 150 act cag ctc agc tac aat gaa tgc agc ggt ctt agc act cag aac cat         592
Thr Gln Leu Ser Tyr Asn Glu Cys Ser Gly Leu Ser Thr Gln Asn His
            155                 160                 165 gca gca aac cac acc cac agg atc aga aca aac cct gcc att gtt aag         640
Ala Ala Asn His Thr His Arg Ile Arg Thr Asn Pro Ala Ile Val Lys
        170                 175                 180 acc gag aat tca tgg agc aat aaa gcg aag agc att tgt caa cag caa         688
Thr Glu Asn Ser Trp Ser Asn Lys Ala Lys Ser Ile Cys Gln Gln Gln
    185                 190                 195 aag cca caa aga cgt ccc tgc tca gag ctt ctc aag tat ctg acc aca         736
Lys Pro Gln Arg Arg Pro Cys Ser Glu Leu Leu Lys Tyr Leu Thr Thr
200                 205                 210                 215 aac gat gac cct cct cac acc aaa ccc aca gaa aac agg aac agc agc         784
Asn Asp Asp Pro Pro His Thr Lys Pro Thr Glu Asn Arg Asn Ser Ser
                220                 225                 230 aga gac aaa tgt gct tcc aaa aag aag tcc cat aca caa ccg cag tcg         832
Arg Asp Lys Cys Ala Ser Lys Lys Lys Ser His Thr Gln Pro Gln Ser
            235                 240                 245 caa cat gct caa gcc aaa cca aca act tta tct ctt cct ctg acc cca         880
Gln His Ala Gln Ala Lys Pro Thr Thr Leu Ser Leu Pro Leu Thr Pro
        250                 255                 260 gag tca cca aat gac ccc aag ggt tcc cca ttt gag aac aag act att         928
Glu Ser Pro Asn Asp Pro Lys Gly Ser Pro Phe Glu Asn Lys Thr Ile
    265                 270                 275 gag cga acc tta agt gtg gaa ctc tct gga act gca ggc cta act cct         976
Glu Arg Thr Leu Ser Val Glu Leu Ser Gly Thr Ala Gly Leu Thr Pro
280                 285                 290                 295 ccc aca act cct cct cat aaa gcc aac caa gat aac cct ttc aag gct        1024
Pro Thr Thr Pro Pro His Lys Ala Asn Gln Asp Asn Pro Phe Lys Ala
```

-continued

```
                    300                 305                 310
tcg cca aag ctg aag ccc tct tgc aag acc gtg gtg cca ccg cca acc    1072
Ser Pro Lys Leu Lys Pro Ser Cys Lys Thr Val Val Pro Pro Pro Thr
            315                 320                 325 aag agg gcc cgg tac agt gag tgt tct ggt acc caa ggc agc cac tcc    1120
Lys Arg Ala Arg Tyr Ser Glu Cys Ser Gly Thr Gln Gly Ser His Ser
        330                 335                 340 acc aag aaa ggg ccc gag caa tct gag ttg tac gca caa ctc agc aag    1168
Thr Lys Lys Gly Pro Glu Gln Ser Glu Leu Tyr Ala Gln Leu Ser Lys
    345                 350                 355 tcc tca ggg ctc agc cga gga cac gag gaa agg aag act aaa cgg ccc    1216
Ser Ser Gly Leu Ser Arg Gly His Glu Glu Arg Lys Thr Lys Arg Pro
360                 365                 370                 375 agt ctc cgg ctg ttt ggt gac cat gac tac tgt cag tca ctc aat tcc    1264
Ser Leu Arg Leu Phe Gly Asp His Asp Tyr Cys Gln Ser Leu Asn Ser
                380                 385                 390 aaa acg gat ata ctc att aac ata tca cag gag ctc caa gac tct aga    1312
Lys Thr Asp Ile Leu Ile Asn Ile Ser Gln Glu Leu Gln Asp Ser Arg
            395                 400                 405 caa cta gac ttc aaa gat gcc tcc tgt gac tgg cag ggg cac atc tgt    1360
Gln Leu Asp Phe Lys Asp Ala Ser Cys Asp Trp Gln Gly His Ile Cys
        410                 415                 420 tct tcc aca gat tca ggc cag tgc tac ctg aga gag act ttg gag gcc    1408
Ser Ser Thr Asp Ser Gly Gln Cys Tyr Leu Arg Glu Thr Leu Glu Ala
    425                 430                 435 agc aag cag gtc tct cct tgc agc acc aga aaa cag ctc caa gac cag    1456
Ser Lys Gln Val Ser Pro Cys Ser Thr Arg Lys Gln Leu Gln Asp Gln
440                 445                 450                 455 gaa atc cga gcg gag ctg aac aag cac ttc ggt cat ccc tgt caa gct    1504
Glu Ile Arg Ala Glu Leu Asn Lys His Phe Gly His Pro Cys Gln Ala
                460                 465                 470 gtg ttt gac gac aaa tca gac aag acc agt gaa cta agg gat ggc gac    1552
Val Phe Asp Asp Lys Ser Asp Lys Thr Ser Glu Leu Arg Asp Gly Asp
            475                 480                 485 ttc agt aat gaa caa ttc tcc aaa cta cct gtg ttt ata aat tca gga    1600
Phe Ser Asn Glu Gln Phe Ser Lys Leu Pro Val Phe Ile Asn Ser Gly
        490                 495                 500 cta gcc atg gat ggc cta ttt gat gac agt gaa gat gaa agt gat aaa    1648
Leu Ala Met Asp Gly Leu Phe Asp Asp Ser Glu Asp Glu Ser Asp Lys
    505                 510                 515 ctg agc tac cct tgg gat ggc acg cag ccc tat tca ttg ttc gat gtg    1696
Leu Ser Tyr Pro Trp Asp Gly Thr Gln Pro Tyr Ser Leu Phe Asp Val
520                 525                 530                 535 tcg cct tct tgc tct tcc ttt aac tct ccg tgt cga gac tca gtg tca    1744
Ser Pro Ser Cys Ser Ser Phe Asn Ser Pro Cys Arg Asp Ser Val Ser
                540                 545                 550 cca ccg aaa tcc tta ttt tct caa aga ccc caa agg atg cgc tct cgt    1792
Pro Pro Lys Ser Leu Phe Ser Gln Arg Pro Gln Arg Met Arg Ser Arg
            555                 560                 565 tca aga tcc ttt tct cga cac agg tcg tgt tcc cga tca cca tat tcc    1840
Ser Arg Ser Phe Ser Arg His Arg Ser Cys Ser Arg Ser Pro Tyr Ser
        570                 575                 580 agg tca aga tca agg tcc cca ggc agt aga tcc tct tca aga tcc tgt    1888
Arg Ser Arg Ser Arg Ser Pro Gly Ser Arg Ser Ser Ser Arg Ser Cys
    585                 590                 595 tac tac tat gaa tca agc cac tac aga cac cgc aca cac cgc aat tct    1936
Tyr Tyr Tyr Glu Ser Ser His Tyr Arg His Arg Thr His Arg Asn Ser
600                 605                 610                 615 ccc ttg tat gtg aga tca cgt tca agg tca ccc tac agc cgt agg ccc    1984
Pro Leu Tyr Val Arg Ser Arg Ser Arg Ser Pro Tyr Ser Arg Arg Pro
```

```
Pro Leu Tyr Val Arg Ser Arg Ser Arg Ser Pro Tyr Ser Arg Arg Pro
            620                 625                 630 agg tac gac agc tat gaa gcc tat gag cac gaa agg ctc aag agg gat    2032
Arg Tyr Asp Ser Tyr Glu Ala Tyr Glu His Glu Arg Leu Lys Arg Asp
                635                 640                 645 gaa tac cgc aaa gag cac gag aag cgg gag tct gaa agg gcc aaa cag    2080
Glu Tyr Arg Lys Glu His Glu Lys Arg Glu Ser Glu Arg Ala Lys Gln
        650                 655                 660 aga gag agg cag aag cag aaa gca att gaa gag cgc cgt gtg att tac    2128
Arg Glu Arg Gln Lys Gln Lys Ala Ile Glu Glu Arg Arg Val Ile Tyr
    665                 670                 675 gtt ggt aaa atc aga cct gac aca acg cgg aca gaa ttg aga gac cgc    2176
Val Gly Lys Ile Arg Pro Asp Thr Thr Arg Thr Glu Leu Arg Asp Arg
680                 685                 690                 695 ttt gaa gtt ttt ggt gaa att gag gaa tgc acc gta aat ctg cgg gat    2224
Phe Glu Val Phe Gly Glu Ile Glu Glu Cys Thr Val Asn Leu Arg Asp
                700                 705                 710 gat gga gac agc tat ggt ttc atc acc tac cgt tac acc tgt gac gct    2272
Asp Gly Asp Ser Tyr Gly Phe Ile Thr Tyr Arg Tyr Thr Cys Asp Ala
            715                 720                 725 ttc gct gct ctt gag aat gga tat act tta cgc agg tcg aac gaa act    2320
Phe Ala Ala Leu Glu Asn Gly Tyr Thr Leu Arg Arg Ser Asn Glu Thr
        730                 735                 740 gac ttc gag ctg tac ttt tgt gga cgg aag caa ttt ttc aag tct aac    2368
Asp Phe Glu Leu Tyr Phe Cys Gly Arg Lys Gln Phe Phe Lys Ser Asn
    745                 750                 755 tat gca gac cta gat acc aac tca gac gat ttt gac cct gct tcc acc    2416
Tyr Ala Asp Leu Asp Thr Asn Ser Asp Asp Phe Asp Pro Ala Ser Thr
760                 765                 770                 775 aag agc aag tat gac tct ctg gat ttt gat agt tta ctg aag gaa gct    2464
Lys Ser Lys Tyr Asp Ser Leu Asp Phe Asp Ser Leu Leu Lys Glu Ala
                780                 785                 790 cag aga agc ttg cgc agg taacgtgttc ccaggctgag gaatgacaga           2512
Gln Arg Ser Leu Arg Arg
            795 gagatggtca atacctcatg ggacagcgtg tcctttccca agactcttgc aagtcatact  2572 taggaatttc tcctacttta cactctctgt acaaaaataa acaaaacaa aacaacaata   2632 acaacaacaa caacaacaat aacaacaaca accataccag aacaagaaca acggtttaca  2692 tgaacacagc tgctgaagag gcaagagaca gaatgataat ccagtaagca cacgtttatt  2752 cacgggtgtc agctttgctt tccctggagg ctcttggtga cagtgtgtgt gcgtgtgtgt  2812 gtgtgggtgt gcgtgtgtgt atgtgtgtgt gtgtacttgt ttggaaagta catatgtaca  2872 catgtgagga cttgggggca cctgaacaga acgaacaagg gcgacccctt caaatggcag  2932 catttccatg aagacacact taaaacctac aacttcaaaa tgttcgtatt ctatacaaaa  2992 ggaaaataaa taaatataaa aaaaaaaaaa aaaaactcg agagatctat gaatcgtaga   3052 tactgaaaaa cccc                                                    3066

<210> SEQ ID NO 2
<211> LENGTH: 797
<212> TYPE: PRT
<213> ORGANISM: Mus musculus

<400> SEQUENCE: 2

Met Ala Trp Asp Met Cys Ser Gln Asp Ser Val Trp Ser Asp Ile Glu
 1               5                  10                  15

Cys Ala Ala Leu Val Gly Glu Asp Gln Pro Leu Cys Pro Asp Leu Pro
```

-continued

```
                  20                  25                  30
Glu Leu Asp Leu Ser Glu Leu Asp Val Asn Asp Leu Asp Thr Asp Ser
             35                  40                  45

Phe Leu Gly Gly Leu Lys Trp Cys Ser Asp Gln Ser Glu Ile Ile Ser
 50                  55                  60

Asn Gln Tyr Asn Asn Glu Pro Ala Asn Ile Phe Glu Lys Ile Asp Glu
 65                  70                  75                  80

Glu Asn Glu Ala Asn Leu Leu Ala Val Leu Thr Glu Thr Leu Asp Ser
                 85                  90                  95

Leu Pro Val Asp Glu Asp Gly Leu Pro Ser Phe Asp Ala Leu Thr Asp
                100                 105                 110

Gly Ala Val Thr Thr Asp Asn Glu Ala Ser Pro Ser Met Pro Asp
            115                 120                 125

Gly Thr Pro Pro Gln Glu Ala Glu Pro Ser Leu Leu Lys Lys
            130                 135                 140

Leu Leu Leu Ala Pro Ala Asn Thr Gln Leu Ser Tyr Asn Glu Cys Ser
145                 150                 155                 160

Gly Leu Ser Thr Gln Asn His Ala Ala Asn His Thr His Arg Ile Arg
                165                 170                 175

Thr Asn Pro Ala Ile Val Lys Thr Glu Asn Ser Trp Ser Asn Lys Ala
                180                 185                 190

Lys Ser Ile Cys Gln Gln Lys Pro Gln Arg Arg Pro Cys Ser Glu
            195                 200                 205

Leu Leu Lys Tyr Leu Thr Thr Asn Asp Pro Pro His Thr Lys Pro
            210                 215                 220

Thr Glu Asn Arg Asn Ser Ser Arg Asp Lys Cys Ala Ser Lys Lys
225                 230                 235                 240

Ser His Thr Gln Pro Gln Ser Gln His Ala Gln Ala Lys Pro Thr Thr
                245                 250                 255

Leu Ser Leu Pro Leu Thr Pro Glu Ser Pro Asn Asp Pro Lys Gly Ser
            260                 265                 270

Pro Phe Glu Asn Lys Thr Ile Glu Arg Thr Leu Ser Val Glu Leu Ser
            275                 280                 285

Gly Thr Ala Gly Leu Thr Pro Pro Thr Thr Pro Pro His Lys Ala Asn
290                 295                 300

Gln Asp Asn Pro Phe Lys Ala Ser Pro Lys Leu Lys Pro Ser Cys Lys
305                 310                 315                 320

Thr Val Val Pro Pro Thr Lys Arg Ala Arg Tyr Ser Glu Cys Ser
            325                 330                 335

Gly Thr Gln Gly Ser His Ser Thr Lys Lys Gly Pro Glu Gln Ser Glu
            340                 345                 350

Leu Tyr Ala Gln Leu Ser Lys Ser Ser Gly Leu Ser Arg Gly His Glu
            355                 360                 365

Glu Arg Lys Thr Lys Arg Pro Ser Leu Arg Leu Phe Gly Asp His Asp
            370                 375                 380

Tyr Cys Gln Ser Leu Asn Ser Lys Thr Asp Ile Leu Ile Asn Ile Ser
385                 390                 395                 400

Gln Glu Leu Gln Asp Ser Arg Gln Leu Asp Phe Lys Asp Ala Ser Cys
                405                 410                 415

Asp Trp Gln Gly His Ile Cys Ser Ser Thr Asp Ser Gly Gln Cys Tyr
            420                 425                 430

Leu Arg Glu Thr Leu Glu Ala Ser Lys Gln Val Ser Pro Cys Ser Thr
            435                 440                 445
```

-continued

```
Arg Lys Gln Leu Gln Asp Gln Glu Ile Arg Ala Glu Leu Asn Lys His
    450                 455                 460

Phe Gly His Pro Cys Gln Ala Val Phe Asp Asp Lys Ser Asp Lys Thr
465                 470                 475                 480

Ser Glu Leu Arg Asp Gly Asp Phe Ser Asn Glu Gln Phe Ser Lys Leu
                485                 490                 495

Pro Val Phe Ile Asn Ser Gly Leu Ala Met Asp Gly Leu Phe Asp Asp
            500                 505                 510

Ser Glu Asp Glu Ser Asp Lys Leu Ser Tyr Pro Trp Asp Gly Thr Gln
        515                 520                 525

Pro Tyr Ser Leu Phe Asp Val Ser Pro Ser Cys Ser Ser Phe Asn Ser
    530                 535                 540

Pro Cys Arg Asp Ser Val Ser Pro Pro Lys Ser Leu Phe Ser Gln Arg
545                 550                 555                 560

Pro Gln Arg Met Arg Ser Arg Ser Arg Ser Phe Ser Arg His Arg Ser
                565                 570                 575

Cys Ser Arg Ser Pro Tyr Ser Arg Ser Arg Ser Arg Ser Pro Gly Ser
            580                 585                 590

Arg Ser Ser Arg Ser Cys Tyr Tyr Tyr Glu Ser Ser His Tyr Arg
        595                 600                 605

His Arg Thr His Arg Asn Ser Pro Leu Tyr Val Arg Ser Arg Ser Arg
    610                 615                 620

Ser Pro Tyr Ser Arg Arg Pro Arg Tyr Asp Ser Tyr Glu Ala Tyr Glu
625                 630                 635                 640

His Glu Arg Leu Lys Arg Asp Glu Tyr Arg Lys Glu His Glu Lys Arg
                645                 650                 655

Glu Ser Glu Arg Ala Lys Gln Arg Glu Arg Gln Lys Gln Lys Ala Ile
            660                 665                 670

Glu Glu Arg Arg Val Ile Tyr Val Gly Lys Ile Arg Pro Asp Thr Thr
        675                 680                 685

Arg Thr Glu Leu Arg Asp Arg Phe Glu Val Phe Gly Glu Ile Glu Glu
    690                 695                 700

Cys Thr Val Asn Leu Arg Asp Asp Gly Asp Ser Tyr Gly Phe Ile Thr
705                 710                 715                 720

Tyr Arg Tyr Thr Cys Asp Ala Phe Ala Ala Leu Glu Asn Gly Tyr Thr
                725                 730                 735

Leu Arg Arg Ser Asn Glu Thr Asp Phe Glu Leu Tyr Phe Cys Gly Arg
            740                 745                 750

Lys Gln Phe Phe Lys Ser Asn Tyr Ala Asp Leu Asp Thr Asn Ser Asp
        755                 760                 765

Asp Phe Asp Pro Ala Ser Thr Lys Ser Lys Tyr Asp Ser Leu Asp Phe
    770                 775                 780

Asp Ser Leu Leu Lys Glu Ala Gln Arg Ser Leu Arg Arg
785                 790                 795

<210> SEQ ID NO 3
<211> LENGTH: 5
<212> TYPE: PRT
<213> ORGANISM: Mus musculus
<220> FEATURE:
<223> OTHER INFORMATION: Xaas at postions 2 and 3 may be any amino acid

<400> SEQUENCE: 3

Leu Xaa Xaa Leu Leu
  1               5
```

<210> SEQ ID NO 4
<211> LENGTH: 3023
<212> TYPE: DNA
<213> ORGANISM: Homo sapiens
<220> FEATURE:
<221> NAME/KEY: CDS
<222> LOCATION: (89)..(2482)

<400> SEQUENCE: 4

| | |
|---|---|
| caggtggctg gttgcctgca tgagtgtgtg ctctgtgtca ctgtggattg gagttgaaaa | 60 |

| | | | | | | | | | | | | | | | | |
|---|---|---|---|---|---|---|---|---|---|---|---|---|---|---|---|---|
| agcttgactg cgtcattca ggagctgg | atg | gcg | tgg | gac | atg | tgc | aac | cag | | | | | | | | 112 |
| | | Met | Ala | Trp | Asp | Met | Cys | Asn | Gln | | | | | | | |
| | | 1 | | | 5 | | | | | | | | | | | |
| gac | tct | gag | tct | gta | tgg | agt | gac | atc | gag | tgt | gct | gct | ctg | gtt | ggt | 160 |
| Asp | Ser | Glu | Ser | Val | Trp | Ser | Asp | Ile | Glu | Cys | Ala | Ala | Leu | Val | Gly | |
| 10 | | | | 15 | | | | | 20 | | | | | | | |
| gaa | gac | cag | cct | ctt | tgc | cca | gat | ctt | cct | gaa | ctt | gat | ctt | tct | gaa | 208 |
| Glu | Asp | Gln | Pro | Leu | Cys | Pro | Asp | Leu | Pro | Glu | Leu | Asp | Leu | Ser | Glu | |
| 25 | | | | 30 | | | | | 35 | | | | | 40 | | |
| cta | gat | gtg | aac | gac | ttg | gat | aca | gac | agc | ttt | ctg | ggt | gga | ctc | aag | 256 |
| Leu | Asp | Val | Asn | Asp | Leu | Asp | Thr | Asp | Ser | Phe | Leu | Gly | Gly | Leu | Lys | |
| | | | | 45 | | | | | 50 | | | | | 55 | | |
| tgg | tgc | agt | gac | caa | tca | gaa | ata | ata | tcc | aat | cag | tac | aac | aat | gag | 304 |
| Trp | Cys | Ser | Asp | Gln | Ser | Glu | Ile | Ile | Ser | Asn | Gln | Tyr | Asn | Asn | Glu | |
| | | | 60 | | | | | 65 | | | | | 70 | | | |
| cct | tca | aac | ata | ttt | gag | aag | ata | gat | gaa | gag | aat | gag | gca | aac | ttg | 352 |
| Pro | Ser | Asn | Ile | Phe | Glu | Lys | Ile | Asp | Glu | Glu | Asn | Glu | Ala | Asn | Leu | |
| | | 75 | | | | | 80 | | | | | 85 | | | | |
| cta | gca | gtc | ctc | aca | gag | aca | cta | gac | agt | ctc | cct | gtg | gat | gaa | gac | 400 |
| Leu | Ala | Val | Leu | Thr | Glu | Thr | Leu | Asp | Ser | Leu | Pro | Val | Asp | Glu | Asp | |
| | 90 | | | | | 95 | | | | | 100 | | | | | |
| gga | ttg | ccc | tca | ttt | gat | gcg | ctg | aca | gat | gga | gac | gtg | acc | act | gac | 448 |
| Gly | Leu | Pro | Ser | Phe | Asp | Ala | Leu | Thr | Asp | Gly | Asp | Val | Thr | Thr | Asp | |
| 105 | | | | | 110 | | | | | 115 | | | | | 120 | |
| aat | gag | gct | agt | cct | tcc | tcc | atg | cct | gac | ggc | acc | cct | cca | ccc | cag | 496 |
| Asn | Glu | Ala | Ser | Pro | Ser | Ser | Met | Pro | Asp | Gly | Thr | Pro | Pro | Pro | Gln | |
| | | | | 125 | | | | | 130 | | | | | 135 | | |
| gag | gca | gaa | gag | ccg | tct | cta | ctt | aag | aag | ctc | tta | ctg | gca | cca | gcc | 544 |
| Glu | Ala | Glu | Glu | Pro | Ser | Leu | Leu | Lys | Lys | Leu | Leu | Leu | Ala | Pro | Ala | |
| | | | 140 | | | | | 145 | | | | | 150 | | | |
| aac | act | cag | cta | agt | tat | aat | gaa | tgc | agt | ggt | ctc | agt | acc | cag | aac | 592 |
| Asn | Thr | Gln | Leu | Ser | Tyr | Asn | Glu | Cys | Ser | Gly | Leu | Ser | Thr | Gln | Asn | |
| | | 155 | | | | | 160 | | | | | 165 | | | | |
| cat | gca | aat | cac | aat | cac | agg | atc | aga | aca | aac | cct | gca | att | gtt | aag | 640 |
| His | Ala | Asn | His | Asn | His | Arg | Ile | Arg | Thr | Asn | Pro | Ala | Ile | Val | Lys | |
| | 170 | | | | | 175 | | | | | 180 | | | | | |
| act | gag | aat | tca | tgg | agc | aat | aaa | gcg | aag | agt | att | tgt | caa | cag | caa | 688 |
| Thr | Glu | Asn | Ser | Trp | Ser | Asn | Lys | Ala | Lys | Ser | Ile | Cys | Gln | Gln | Gln | |
| 185 | | | | | 190 | | | | | 195 | | | | | 200 | |
| aag | cca | caa | aga | cgt | ccc | tgc | tcg | gag | ctt | ctc | aaa | tat | ctg | acc | aca | 736 |
| Lys | Pro | Gln | Arg | Arg | Pro | Cys | Ser | Glu | Leu | Leu | Lys | Tyr | Leu | Thr | Thr | |
| | | | | 205 | | | | | 210 | | | | | 215 | | |
| aac | gat | gac | cct | cct | cac | acc | aaa | ccc | aca | gag | aac | aga | aac | agc | agc | 784 |
| Asn | Asp | Asp | Pro | Pro | His | Thr | Lys | Pro | Thr | Glu | Asn | Arg | Asn | Ser | Ser | |
| | | | 220 | | | | | 225 | | | | | 230 | | | |
| aga | gac | aaa | tgc | acc | tcc | aaa | aag | aag | tcc | cac | aca | cag | tcg | cag | tca | 832 |
| Arg | Asp | Lys | Cys | Thr | Ser | Lys | Lys | Lys | Ser | His | Thr | Gln | Ser | Gln | Ser | |
| | | 235 | | | | | 240 | | | | | 245 | | | | |
| caa | cac | tta | caa | gcc | aaa | cca | aca | act | tta | tct | ctt | cct | ctg | acc | cca | 880 |

```
          Gln His Leu Gln Ala Lys Pro Thr Thr Leu Ser Leu Pro Leu Thr Pro
              250                 255                 260 gag tca cca aat gac ccc aag ggt tcc cca ttt gag aac aag act att          928
Glu Ser Pro Asn Asp Pro Lys Gly Ser Pro Phe Glu Asn Lys Thr Ile
265                 270                 275                 280 gaa cgc acc tta agt gtg gaa ctc tct gga act gca ggc cta act cca          976
Glu Arg Thr Leu Ser Val Glu Leu Ser Gly Thr Ala Gly Leu Thr Pro
              285                 290                 295 ccc acc act cct cct cat aaa gcc aac caa gat aac cct ttt agg gct         1024
Pro Thr Thr Pro Pro His Lys Ala Asn Gln Asp Asn Pro Phe Arg Ala
                  300                 305                 310 tct cca aag ctg aag tcc tct tgc aag act gtg gtg cca cca cca tca         1072
Ser Pro Lys Leu Lys Ser Ser Cys Lys Thr Val Val Pro Pro Pro Ser
              315                 320                 325 aag aag ccc agg tac agt gag tct tct ggt aca caa ggc aat aac tcc         1120
Lys Lys Pro Arg Tyr Ser Glu Ser Ser Gly Thr Gln Gly Asn Asn Ser
          330                 335                 340 acc aag aaa ggg ccg gag caa tcc gag ttg tat gca caa ctc agc aag         1168
Thr Lys Lys Gly Pro Glu Gln Ser Glu Leu Tyr Ala Gln Leu Ser Lys
345                 350                 355                 360 tcc tca gtc ctc act ggt gga cac gag gaa agg aag acc aag cgg ccc         1216
Ser Ser Val Leu Thr Gly Gly His Glu Glu Arg Lys Thr Lys Arg Pro
              365                 370                 375 agt ctg cgg ctg ttt ggt gac cat gac tat tgc cag tca att aat tcc         1264
Ser Leu Arg Leu Phe Gly Asp His Asp Tyr Cys Gln Ser Ile Asn Ser
                  380                 385                 390 aaa acg gaa ata ctc att aat ata tca cag gag ctc caa gac tct aga         1312
Lys Thr Glu Ile Leu Ile Asn Ile Ser Gln Glu Leu Gln Asp Ser Arg
              395                 400                 405 caa cta gaa aat aaa gat gtc tcc tct gat tgg cag ggg cag att tgt         1360
Gln Leu Glu Asn Lys Asp Val Ser Ser Asp Trp Gln Gly Gln Ile Cys
          410                 415                 420 tct tcc aca gat tca gac cag tgc tac ctg aga gag act ttg gag gca         1408
Ser Ser Thr Asp Ser Asp Gln Cys Tyr Leu Arg Glu Thr Leu Glu Ala
425                 430                 435                 440 agc aag cag gtc tct cct tgc agc aca aga aaa cag ctc caa gac cag         1456
Ser Lys Gln Val Ser Pro Cys Ser Thr Arg Lys Gln Leu Gln Asp Gln
              445                 450                 455 gaa atc cga gcc gag ctg aac aag cac ttc ggt cat ccc agt caa gct         1504
Glu Ile Arg Ala Glu Leu Asn Lys His Phe Gly His Pro Ser Gln Ala
                  460                 465                 470 gtt ttt gac gac gaa gca gac aag acc ggt gaa ctg agg gac agt gat         1552
Val Phe Asp Asp Glu Ala Asp Lys Thr Gly Glu Leu Arg Asp Ser Asp
              475                 480                 485 ttc agt aat gaa caa ttc tcc aaa cta cct atg ttt ata aat tca gga         1600
Phe Ser Asn Glu Gln Phe Ser Lys Leu Pro Met Phe Ile Asn Ser Gly
          490                 495                 500 cta gcc atg gat ggc ctg ttt gat gac agc gaa gat aaa agt gat aaa         1648
Leu Ala Met Asp Gly Leu Phe Asp Asp Ser Glu Asp Lys Ser Asp Lys
505                 510                 515                 520 ctg agc tac cct tgg gat ggc acg caa tcc tat tca ttg ttc aat gtg         1696
Leu Ser Tyr Pro Trp Asp Gly Thr Gln Ser Tyr Ser Leu Phe Asn Val
              525                 530                 535 tct cct tct tgt tct tct ttt aac tct cca tgt aga gat tct gtg tca         1744
Ser Pro Ser Cys Ser Ser Phe Asn Ser Pro Cys Arg Asp Ser Val Ser
                  540                 545                 550 cca ccc aaa tcc tta ttt tct caa aga ccc caa agg atg cgc tct cgt         1792
Pro Pro Lys Ser Leu Phe Ser Gln Arg Pro Gln Arg Met Arg Ser Arg
              555                 560                 565
```

```
tca agg tcc ttt tct cga cac agg tcg tgt tcc cga tca cca tat tcc      1840
Ser Arg Ser Phe Ser Arg His Arg Ser Cys Ser Arg Ser Pro Tyr Ser
    570             575                 580 agg tca aga tca agg tct cca ggc agt aga tcc tct tca aga tcc tgc      1888
Arg Ser Arg Ser Arg Ser Pro Gly Ser Arg Ser Ser Arg Ser Cys
585             590                 595                 600 tat tac tat gag tca agc cac tac aga cac cgc acg cac cga aat tct      1936
Tyr Tyr Tyr Glu Ser Ser His Tyr Arg His Arg Thr His Arg Asn Ser
                605                 610                 615 ccc ttg tat gtg aga tca cgt tca aga tcg ccc tac agc cgt cgg ccc      1984
Pro Leu Tyr Val Arg Ser Arg Ser Arg Ser Pro Tyr Ser Arg Arg Pro
            620                 625                 630 agg tat gac agc tac gag gaa tat cag cac gag agg ctg aag agg gaa      2032
Arg Tyr Asp Ser Tyr Glu Glu Tyr Gln His Glu Arg Leu Lys Arg Glu
        635                 640                 645 gaa tat cgc aga gag tat gag aag cga gag tct gag agg gcc aag caa      2080
Glu Tyr Arg Arg Glu Tyr Glu Lys Arg Glu Ser Glu Arg Ala Lys Gln
650                 655                 660 agg gag agg cag agg cag aag gca att gaa gag cgc cgt gtg att tat      2128
Arg Glu Arg Gln Arg Gln Lys Ala Ile Glu Glu Arg Arg Val Ile Tyr
665                 670                 675                 680 gtc ggt aaa atc aga cct gac aca aca cgg aca gaa ctg agg gac cgt      2176
Val Gly Lys Ile Arg Pro Asp Thr Thr Arg Thr Glu Leu Arg Asp Arg
                685                 690                 695 ttt gaa gtt ttt ggt gaa att gag gag tgc aca gta aat ctg cgg gat      2224
Phe Glu Val Phe Gly Glu Ile Glu Glu Cys Thr Val Asn Leu Arg Asp
            700                 705                 710 gat gga gac agc tat ggt ttc att acc tac cgt tat acc tgt gat gct      2272
Asp Gly Asp Ser Tyr Gly Phe Ile Thr Tyr Arg Tyr Thr Cys Asp Ala
        715                 720                 725 ttt gct gct ctt gaa aat gga tac act ttg cgc agg tca aac gaa act      2320
Phe Ala Ala Leu Glu Asn Gly Tyr Thr Leu Arg Arg Ser Asn Glu Thr
730                 735                 740 gac ttt gag ctg tac ttt tgt gga cgc aag caa ttt ttc aag tct aac      2368
Asp Phe Glu Leu Tyr Phe Cys Gly Arg Lys Gln Phe Phe Lys Ser Asn
745                 750                 755                 760 tat gca gac cta gat tca aac tca gat gac ttt gac cct gct tcc acc      2416
Tyr Ala Asp Leu Asp Ser Asn Ser Asp Asp Phe Asp Pro Ala Ser Thr
                765                 770                 775 aag agc aag tat gac tct ctg gat ttt gat agt tta ctg aaa gaa gct      2464
Lys Ser Lys Tyr Asp Ser Leu Asp Phe Asp Ser Leu Leu Lys Glu Ala
            780                 785                 790 cag aga agc ttg cgc agg taacatgttc cctagctgag gatgacagag             2512
Gln Arg Ser Leu Arg Arg
            795 ggatggcgaa tacctcatgg gacagcgcgt ccttccctaa agactattgc aagtcatact    2572 taggaatttc tcctacttta cactctctgt acaaaaacaa aacaaaacaa caacaataca    2632 acaagaacaa caacaacaat aacaacaatg gtttacatga acacagctgc tgaagaggca    2692 agagacagaa tgatatccag taagcacatg tttattcatg ggtgtcagct ttgcttttcc    2752 tggagtctct tggtgatgga gtgtgcgtgt gtgcatgtat gtgtgtgtgt atgtatgtgt    2812 gtggtgtgtg tgcttggttt aggggaagta tgtgtgggta catgtgagga ctgggggcac    2872 ctgaccagaa tgcgcaaggg caaaccattt caaatggcag cagttccatg aagacacact    2932 taaaacctag aacttcaaaa tgttcgtatt ctattcaaaa ggaaaaatat atatatatat    2992 atatatatat aaattaaaaa aaaaaaaaaa a                                   3023
```

<210> SEQ ID NO 5
<211> LENGTH: 798
<212> TYPE: PRT
<213> ORGANISM: Homo sapiens

<400> SEQUENCE: 5

```
Met Ala Trp Asp Met Cys Asn Gln Asp Ser Glu Val Trp Ser Asp
 1               5                  10                  15

Ile Glu Cys Ala Ala Leu Val Gly Glu Asp Gln Pro Leu Cys Pro Asp
                20                  25                  30

Leu Pro Glu Leu Asp Leu Ser Glu Leu Asp Val Asn Asp Leu Asp Thr
            35                  40                  45

Asp Ser Phe Leu Gly Gly Leu Lys Trp Cys Ser Asp Gln Ser Glu Ile
        50                  55                  60

Ile Ser Asn Gln Tyr Asn Asn Glu Pro Ser Asn Ile Phe Glu Lys Ile
 65                 70                  75                  80

Asp Glu Glu Asn Glu Ala Asn Leu Leu Ala Val Leu Thr Glu Thr Leu
                85                  90                  95

Asp Ser Leu Pro Val Asp Glu Asp Gly Leu Pro Ser Phe Asp Ala Leu
            100                 105                 110

Thr Asp Gly Asp Val Thr Thr Asp Asn Glu Ala Ser Pro Ser Ser Met
        115                 120                 125

Pro Asp Gly Thr Pro Pro Gln Glu Ala Glu Pro Ser Leu Leu
130                 135                 140

Lys Lys Leu Leu Leu Ala Pro Ala Asn Thr Gln Leu Ser Tyr Asn Glu
145                 150                 155                 160

Cys Ser Gly Leu Ser Thr Gln Asn His Ala Asn His Asn His Arg Ile
                165                 170                 175

Arg Thr Asn Pro Ala Ile Val Lys Thr Glu Asn Ser Trp Ser Asn Lys
            180                 185                 190

Ala Lys Ser Ile Cys Gln Gln Gln Lys Pro Gln Arg Arg Pro Cys Ser
        195                 200                 205

Glu Leu Leu Lys Tyr Leu Thr Thr Asn Asp Asp Pro Pro His Thr Lys
210                 215                 220

Pro Thr Glu Asn Arg Asn Ser Ser Arg Asp Lys Cys Thr Ser Lys Lys
225                 230                 235                 240

Lys Ser His Thr Gln Ser Gln Ser Gln His Leu Gln Ala Lys Pro Thr
                245                 250                 255

Thr Leu Ser Leu Pro Leu Thr Pro Glu Ser Pro Asn Asp Pro Lys Gly
            260                 265                 270

Ser Pro Phe Glu Asn Lys Thr Ile Glu Arg Thr Leu Ser Val Glu Leu
        275                 280                 285

Ser Gly Thr Ala Gly Leu Thr Pro Pro Thr Thr Pro Pro His Lys Ala
290                 295                 300

Asn Gln Asp Asn Pro Phe Arg Ala Ser Pro Lys Leu Lys Ser Ser Cys
305                 310                 315                 320

Lys Thr Val Val Pro Pro Pro Ser Lys Lys Pro Arg Tyr Ser Glu Ser
                325                 330                 335

Ser Gly Thr Gln Gly Asn Asn Ser Thr Lys Lys Gly Pro Glu Gln Ser
            340                 345                 350

Glu Leu Tyr Ala Gln Leu Ser Lys Ser Ser Val Leu Thr Gly Gly His
        355                 360                 365

Glu Glu Arg Lys Thr Lys Arg Pro Ser Leu Arg Leu Phe Gly Asp His
370                 375                 380
```

```
Asp Tyr Cys Gln Ser Ile Asn Ser Lys Thr Glu Ile Leu Ile Asn Ile
385                 390                 395                 400

Ser Gln Glu Leu Gln Asp Ser Arg Gln Leu Glu Asn Lys Asp Val Ser
            405                 410                 415

Ser Asp Trp Gln Gly Gln Ile Cys Ser Ser Thr Asp Ser Asp Gln Cys
            420                 425                 430

Tyr Leu Arg Glu Thr Leu Glu Ala Ser Lys Gln Val Ser Pro Cys Ser
            435                 440                 445

Thr Arg Lys Gln Leu Gln Asp Gln Glu Ile Arg Ala Glu Leu Asn Lys
            450                 455                 460

His Phe Gly His Pro Ser Gln Ala Val Phe Asp Glu Ala Asp Lys
465                 470                 475                 480

Thr Gly Glu Leu Arg Asp Ser Asp Phe Ser Asn Glu Gln Phe Ser Lys
            485                 490                 495

Leu Pro Met Phe Ile Asn Ser Gly Leu Ala Met Asp Gly Leu Phe Asp
            500                 505                 510

Asp Ser Glu Asp Lys Ser Asp Lys Leu Ser Tyr Pro Trp Asp Gly Thr
            515                 520                 525

Gln Ser Tyr Ser Leu Phe Asn Val Ser Pro Ser Cys Ser Ser Phe Asn
530                 535                 540

Ser Pro Cys Arg Asp Ser Val Ser Pro Pro Lys Ser Leu Phe Ser Gln
545                 550                 555                 560

Arg Pro Gln Arg Met Arg Ser Arg Ser Arg Ser Phe Ser Arg His Arg
            565                 570                 575

Ser Cys Ser Arg Ser Pro Tyr Ser Arg Ser Arg Ser Arg Ser Pro Gly
            580                 585                 590

Ser Arg Ser Ser Ser Arg Ser Cys Tyr Tyr Tyr Glu Ser Ser His Tyr
            595                 600                 605

Arg His Arg Thr His Arg Asn Ser Pro Leu Tyr Val Arg Ser Arg Ser
            610                 615                 620

Arg Ser Pro Tyr Ser Arg Arg Pro Arg Tyr Asp Ser Tyr Glu Glu Tyr
625                 630                 635                 640

Gln His Glu Arg Leu Lys Arg Glu Glu Tyr Arg Arg Glu Tyr Glu Lys
            645                 650                 655

Arg Glu Ser Glu Arg Ala Lys Gln Arg Glu Arg Gln Arg Gln Lys Ala
            660                 665                 670

Ile Glu Glu Arg Arg Val Ile Tyr Val Gly Lys Ile Arg Pro Asp Thr
            675                 680                 685

Thr Arg Thr Glu Leu Arg Asp Arg Phe Glu Val Phe Gly Glu Ile Glu
            690                 695                 700

Glu Cys Thr Val Asn Leu Arg Asp Asp Gly Asp Ser Tyr Gly Phe Ile
705                 710                 715                 720

Thr Tyr Arg Tyr Thr Cys Asp Ala Phe Ala Ala Leu Glu Asn Gly Tyr
            725                 730                 735

Thr Leu Arg Arg Ser Asn Glu Thr Asp Phe Glu Leu Tyr Phe Cys Gly
            740                 745                 750

Arg Lys Gln Phe Phe Lys Ser Asn Tyr Ala Asp Leu Asp Ser Asn Ser
            755                 760                 765

Asp Asp Phe Asp Pro Ala Ser Thr Lys Ser Lys Tyr Asp Ser Leu Asp
770                 775                 780

Phe Asp Ser Leu Leu Lys Glu Ala Gln Arg Ser Leu Arg Arg
785                 790                 795
```

```
<210> SEQ ID NO 6
<211> LENGTH: 27
<212> TYPE: DNA
<213> ORGANISM: Homo sapiens

<400> SEQUENCE: 6
atcttcgctg tcatcaaaca ggccatc                                              27
```